US012611463B2

(12) United States Patent
Wei et al.

(10) Patent No.: US 12,611,463 B2
(45) Date of Patent: Apr. 28, 2026

(54) METHODS AND IMMUNOGENIC COMPOSITIONS RELATING TO HER2 WITH SELECTIVE SEQUENCE MODIFICATIONS

(71) Applicant: Wayne State University, Detroit, MI (US)

(72) Inventors: Wei-Zen Wei, Grosse Pointe Farms, MI (US); Richard F. Jones, Fayetteville, NY (US); Joyce Reyes, Rochester Hills, MI (US); Heather Gibson, Madison Heights, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 18/528,165

(22) Filed: Dec. 4, 2023

(65) Prior Publication Data

US 2024/0252659 A1     Aug. 1, 2024

Related U.S. Application Data

(63) Continuation of application No. 16/704,679, filed on Dec. 5, 2019, now abandoned.

(60) Provisional application No. 62/775,613, filed on Dec. 5, 2018.

(51) Int. Cl.

| | |
|---|---|
| *A61K 47/58* | (2017.01) |
| *A61K 31/337* | (2006.01) |
| *A61K 35/76* | (2015.01) |
| *A61K 38/28* | (2006.01) |
| *A61K 39/00* | (2006.01) |
| *A61K 39/39* | (2006.01) |
| *A61K 47/54* | (2017.01) |
| *A61K 47/69* | (2017.01) |
| *C07C 227/16* | (2006.01) |
| *C07C 229/22* | (2006.01) |
| *C07K 16/28* | (2006.01) |
| *C08F 120/36* | (2006.01) |
| *C08G 81/02* | (2006.01) |
| *C12N 15/86* | (2006.01) |

(52) U.S. Cl.
CPC ............ *A61K 47/58* (2017.08); *A61K 31/337* (2013.01); *A61K 35/76* (2013.01); *A61K 38/28* (2013.01); *A61K 39/001106* (2018.08); *A61K 39/39* (2013.01); *A61K 47/543* (2017.08); *A61K 47/544* (2017.08); *A61K 47/6909* (2017.08); *A61K 47/6915* (2017.08); *A61K 47/6921* (2017.08); *C07C 227/16* (2013.01); *C07C 229/22* (2013.01); *C08F 120/36* (2013.01); *C08G 81/027* (2013.01); *A61K 39/001104* (2018.08); *A61K 2039/585* (2013.01); *C07K 16/2863* (2013.01); *C12N 15/86* (2013.01)

(58) Field of Classification Search
None
See application file for complete search history.

(56) References Cited

U.S. PATENT DOCUMENTS

| | | | |
|---|---|---|---|
| 7,282,365 B2 | 10/2007 | Monaci et al. | |
| 8,895,017 B2 | 11/2014 | Cho | |
| 9,913,884 B2 | 3/2018 | Fikes et al. | |
| 10,179,820 B2 | 1/2019 | Chen et al. | |
| 10,434,152 B2 | 10/2019 | Wei et al. | |
| 10,859,566 B2 | 12/2020 | Flechtner et al. | |
| 2011/0086055 A1 | 4/2011 | Kaumaya | |
| 2017/0112909 A1* | 4/2017 | Wei ............... | A61K 39/001106 |

FOREIGN PATENT DOCUMENTS

| | | |
|---|---|---|
| WO | 2008/119565 A2 | 10/2008 |
| WO | 2008119567 A2 | 10/2008 |

OTHER PUBLICATIONS

Herold et al (Sci Rep. Sep. 25, 2017;7(1):12276 (Year: 2017).*
Rudikoff et al (Proc Natl Acad Sci U S A. Mar. 1982;79(6):1979-83) (Year: 1982).*
Wada R., et al., mRNA expression of delta-HER2 and itsclinicopathological correlation in HER2-overexpressing breast cancer. Mol Med Rep., Dec. 2016; 14(6):5104-5110. Epub Oct. 26, 2016.

* cited by examiner

*Primary Examiner* — Zachariah Lucas
*Assistant Examiner* — Sarah A Alsomairy
(74) *Attorney, Agent, or Firm* — Julie K. Staple; Fishman Stewart PLLC

(57) ABSTRACT

Only limited success has been previously achieved from cancer vaccines targeting unmodified tumor-associated self-antigens and new compositions and methods are needed. Immunogenic compositions and methods of use thereof are provided according to the present disclosure which include a protein effective to stimulate immune activity against a tumor-associated self-antigen, or a variant thereof which is a tumor-associated self-antigen.

7 Claims, 18 Drawing Sheets

Specification includes a Sequence Listing.

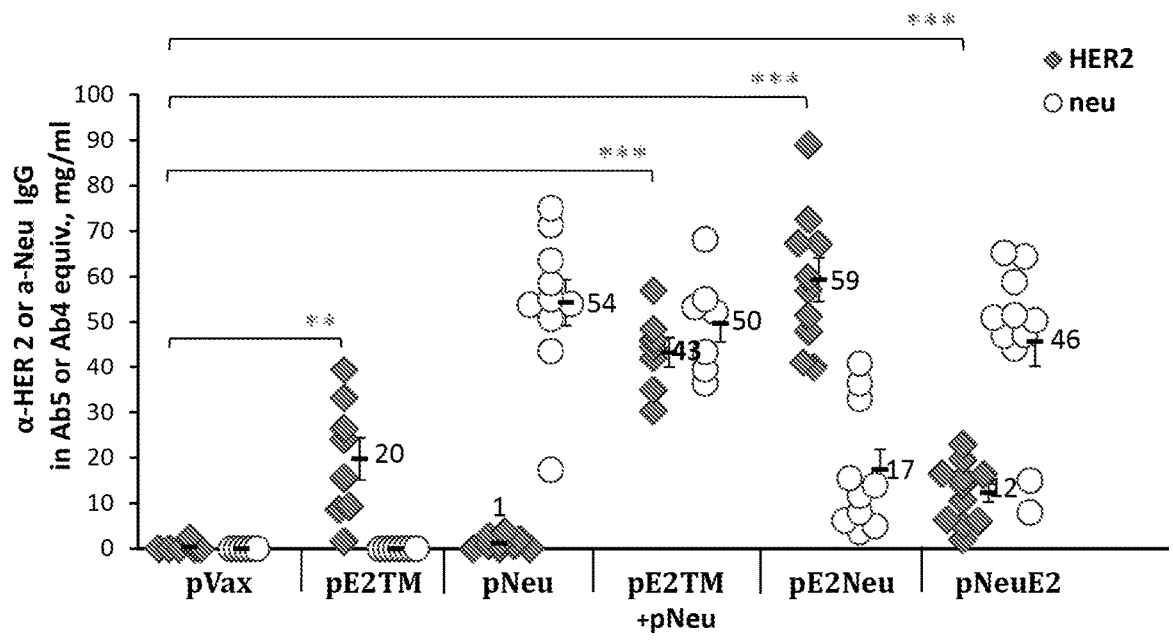
FIG. 1C
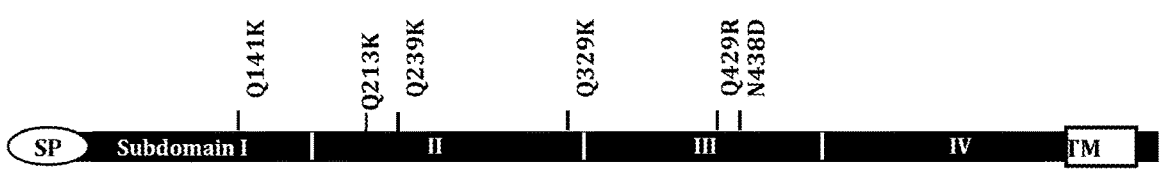
FIG. 2Ai
FIG. 2Aii
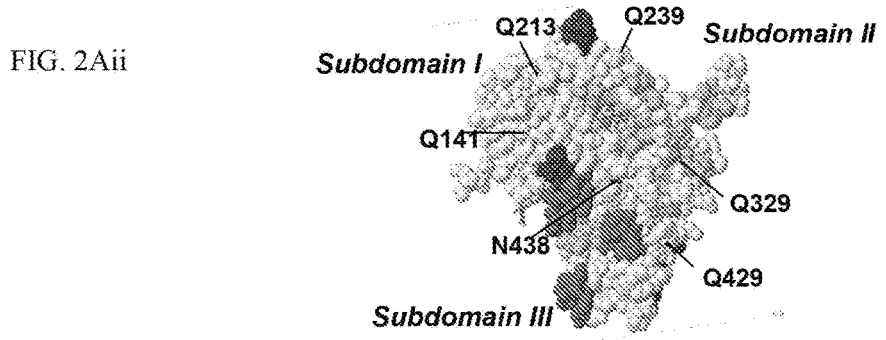

(d)

(e)

pE2TM mAb:

(d)

(e)

(a)     BALB HER2Tg

(b)     B6 HER2Tg

(c)

(d)

(b)

Vaccine h(es)E2TM    $_{355}$LPESFDGDPASNTAP$_{369}$

Vaccine E2Neu    $_{355}$LPESFDGDPASNTAP$_{372}$

AEF

(b)    D2F2/E2t tumor growth in BALB HER2 Tg mice

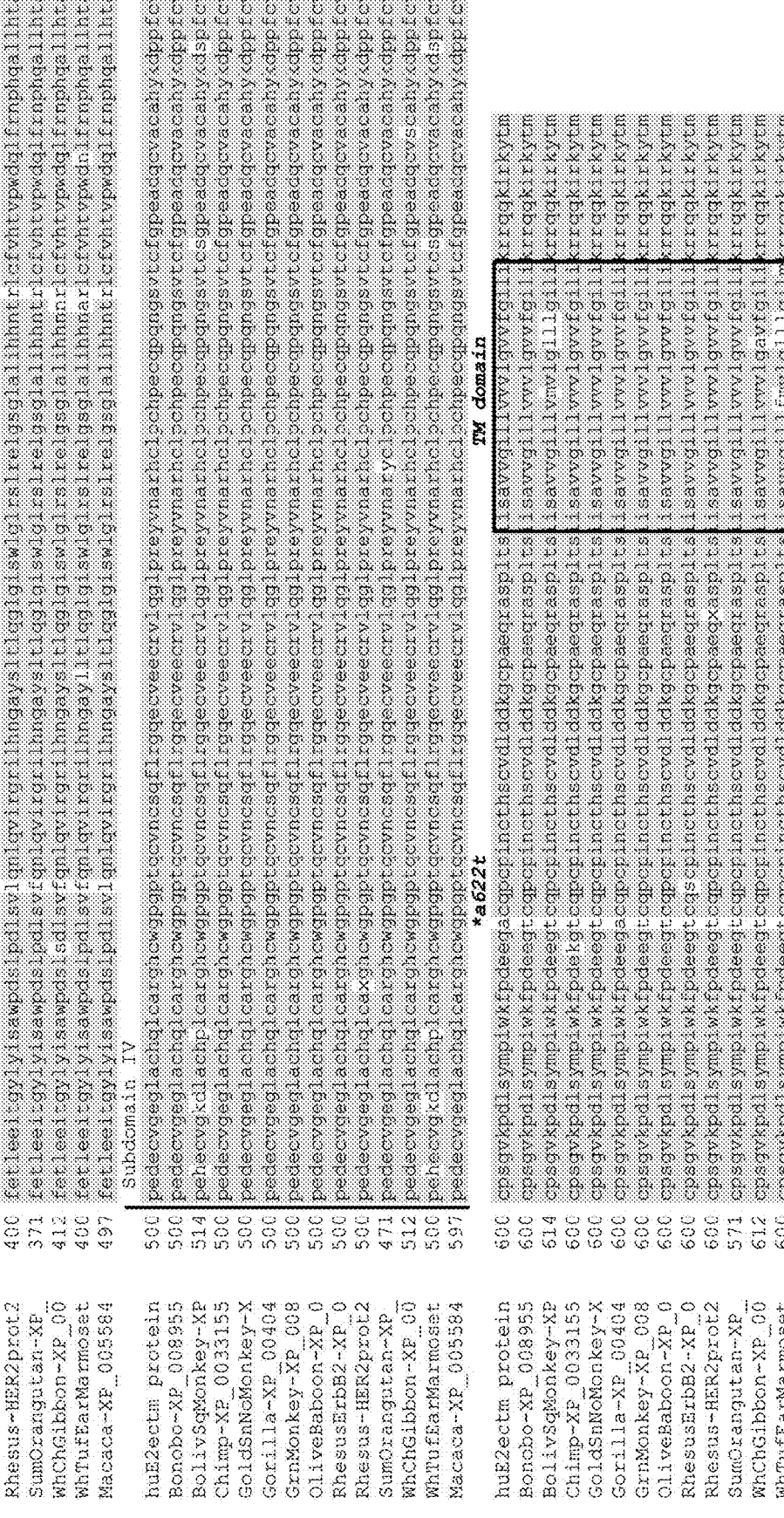
FIGURE 8 - CONTINUED

METHODS AND IMMUNOGENIC COMPOSITIONS RELATING TO HER2 WITH SELECTIVE SEQUENCE MODIFICATIONS

REFERENCE TO RELATED APPLICATIONS

This application is a continuation of U.S. patent application Ser. No. 16/704,679, filed Dec. 5, 2019, which claims priority to U.S. Provisional Patent Application Ser. No. 62/775,613, filed Dec. 5, 2018, the entire content of each application is incorporated herein by reference.

GRANT REFERENCE

This invention was made with government support under Grant No. RO1 CA076340, awarded by the National Institutes of Health. The Government has certain rights in the invention.

SEQUENCE LISTING

The instant application contains a Sequence Listing which has been submitted electronically as a file in XML format and is hereby incorporated by reference in its entirety. Said XML format file, created on Apr. 17, 2024 is named Updated seq list 47WAY13703NA.xml and is 84,707 bytes in size.

FIELD OF THE INVENTION

According to general aspects, the present invention relates to methods for generating immunogenic compositions to treat a disorder in a subject. In specific aspects, the present invention relates to immunogenic compositions which stimulate immune activity against a tumor-associated self-antigen, overcoming self-tolerance, and yet which substantially maintain the native structure of the tumor-associated self-antigen.

BACKGROUND OF THE INVENTION

Increasingly, cancers are found to express proteins which have a non-oncogenic function in normal cells but which play a role in the development of a cancer, typically when overexpressed by the cancer cells.

Clinical successes of checkpoint inhibitors have demonstrated that endogenous immunity can destroy tumors. Although some tumor infiltrating lymphocytes (TIL) recognize neoantigens, the majority of TIL clones recognized tumor-associated self-antigens (TAA). Additionally, active vaccination targeting known TAA may create a favorable tumor microenvironment for neoantigen priming to enhance immune protection. Only limited success, however, has been achieved from cancer vaccines targeting unmodified TAA, specifically, the greatest challenge remains in the balance between self-tolerance and tumor immunity.

HER2 is a member of the epidermal growth factor receptor family described in detail in Harari D, et al., Oncogene, 2001, 19:6102-14. HER2 is overexpressed in breast, ovarian, non-small cell lung, endometrial, gastric and other cancers, stimulating cancer cell growth, see Harari D, et al., Oncogene, 2001, 19:6102-14. Some patients have pre-existing endogenous HER2 immunity, supporting the immunogenic nature of this non-mutated tumor-associated self-antigen (TAA), see Taylor C, et al., Clin. Cancer Res., 2007, 13:5133-43; and Moasser M M, Oncogene, 2007, 26:6469-87.

Both humoral and cellular HER2 immunity contribute to tumor growth inhibition, whether by direct killing through antibodies or T cells, or by Ab-dependent cell-mediated cytotoxicity, culminating in a comprehensive, multi-effector anti-tumor response.

There is a continuing need for compositions and methods for prevention and inhibition of cancer cells. In particular, there is a continuing need for compositions and methods relating to immunogenic compositions which stimulate immune activity against tumor-associated self-antigens. Further, there is a continuing need for methods of generating an immunogenic composition which stimulates immune activity against tumor-associated self-antigens, overcomes self-tolerance, yet substantially maintains the native structure of the tumor-associated self-antigen.

SUMMARY OF THE INVENTION

Immunogenic compositions are provided according to the present invention which include a protein effective to stimulate immune activity against a tumor-associated self-antigen, or a variant thereof which is a tumor-associated self-antigen.

Immunogenic compositions are provided according to the present invention which include a protein effective to stimulate immune activity against HER2, a tumor-associated self-antigen, or a variant thereof which is a tumor-associated self-antigen.

Immunogenic compositions are provided according to the present invention which include a protein effective to stimulate immune activity against human HER2, a tumor-associated self-antigen, or a variant thereof which is a tumor-associated self-antigen.

According to aspects of the present invention, immunogenic compositions are provided which include a protein effective to stimulate immune activity against human HER2 of SEQ ID NO:1, a tumor-associated self-antigen.

According to aspects of the present invention, immunogenic compositions are provided which include a protein effective to stimulate immune activity against a variant of human HER2 of SEQ ID NO:1, a tumor-associated self-antigen.

According to aspects of the present invention, immunogenic compositions are provided which include a protein effective to stimulate immune activity against human HER2 of SEQ ID NO:16, a tumor-associated self-antigen.

According to aspects of the present invention, immunogenic compositions are provided which include a protein effective to stimulate immune activity against a variant human HER2 of SEQ ID NO:16, a tumor-associated self-antigen.

According to aspects of the present invention, immunogenic compositions are provided which include an immunogenic tumor-associated self-antigen characterized by one or more of: 1) effectiveness to stimulate immune activity against a specified tumor-associated self-antigen in a subject, 2) effectiveness to overcome self-tolerance of the specified tumor-associated self-antigen, and 3) substantial similarity to the native three dimensional structure of the specified tumor-associated self-antigen.

According to aspects of the present invention, immunogenic compositions are provided which include an immunogenic HER2 characterized by one or more of: 1) effectiveness to stimulate immune activity against HER2 in a subject, 2) effectiveness to overcome self-tolerance of HER2, and 3) substantial similarity to the native three-dimensional structure of HER2.

According to aspects of the present invention, immunogenic compositions are provided which include an immunogenic human HER2 characterized by one or more of: 1) effectiveness to stimulate immune activity against human HER2 in a subject, 2) effectiveness to overcome self-tolerance of human HER2, and 3) substantial similarity to the native three-dimensional structure of human HER2.

According to aspects of the present invention, immunogenic compositions are provided which include an immunogenic human HER2 of SEQ ID NO:1 characterized by one or more of: 1) effectiveness to stimulate immune activity against human HER2 of SEQ ID NO:1 in a subject, 2) effectiveness to overcome self-tolerance of human HER2 of SEQ ID NO:1, and 3) substantial similarity to the native three dimensional structure of human HER2 of SEQ ID NO:1.

According to aspects of the present invention, immunogenic compositions are provided which include an immunogenic variant of the human HER2 of SEQ ID NO:1 characterized by one or more of: 1) effectiveness to stimulate immune activity against the variant of human HER2 of SEQ ID NO:1 in a subject, 2) effectiveness to overcome self-tolerance of the variant of the human HER2 of SEQ ID NO:1, and 3) substantial similarity to the native three-dimensional structure of the variant of the human HER2 of SEQ ID NO:1.

According to aspects of the present invention, immunogenic compositions are provided which include an immunogenic human HER2 of SEQ ID NO:17 characterized by one or more of: 1) effectiveness to stimulate immune activity against human HER2 of SEQ ID NO:16 in a subject, 2) effectiveness to overcome self-tolerance of the human HER2 of SEQ ID NO:16, and 3) substantial similarity to the native three-dimensional structure of the human HER2 of SEQ ID NO:16.

According to aspects of the present invention, immunogenic compositions are provided which include an immunogenic variant of human HER2 of SEQ ID NO:17 characterized by one or more of: 1) effectiveness to stimulate immune activity against the variant of human HER2 of SEQ ID NO:16 in a subject, 2) effectiveness to overcome self-tolerance of the variant of the human HER2 of SEQ ID NO:16, and 3) substantial similarity to the native three-dimensional structure of the variant of the human HER2 of SEQ ID NO:16.

The term "substantial similarity" used herein in reference to a "native three-dimensional structure" of a protein indicates that the protein included in the immunogenic composition has at least some of the three-dimensional structural characteristics of the corresponding native protein such as, but not limited to, structural similarity evidenced by one or more of: 1) immunoassays using antibodies which recognize both the native protein structure and the protein of the immunogenic composition, 2) structural similarity evidenced by a percent amino acid sequence identity over the full-length of the native protein structure and the protein of the immunogenic composition, wherein the percent amino acid sequence identity is at least 90%, at least 91%, at least 92%, at least 93%, at least 94%, at least 95%, at least 96%, at least 97%, at least 908%, at least 99%, or greater, 3) structural similarity evidenced by NMR spectroscopy, 4) structural similarity evidenced by X-ray crystallography, and 5) structural similarity evidenced by functional assay.

According to aspects of the present invention, immunogenic compositions are provided which include a protein which has, or includes, the amino acid sequence of SEQ ID NO:2.

According to aspects of the present invention, immunogenic compositions are provided which include a protein which has, or includes, the amino acid sequence of SEQ ID NO:2, and wherein the composition includes a pharmaceutically acceptable carrier.

According to aspects of the present invention, immunogenic compositions are provided which include a protein which has, or includes, the amino acid sequence of SEQ ID NO:2, and wherein the composition includes an adjuvant.

According to aspects of the present invention, immunogenic compositions are provided which include a protein which has, or includes, the amino acid sequence of SEQ ID NO:2, and wherein the composition includes an immunostimulating adjuvant.

Recombinant expression constructs are provided according to aspects of the present invention which include a nucleic acid encoding an immunogenic composition, wherein the immunogenic composition includes a protein which has, or includes, the amino acid sequence of SEQ ID NO:2, and wherein the nucleic acid encoding the immunogenic composition is operably linked to a heterologous regulatory nucleic acid sequence.

Recombinant expression constructs are provided according to aspects of the present invention which include a nucleic acid encoding an immunogenic composition, wherein the immunogenic composition includes a protein which has, or includes, the amino acid sequence of SEQ ID NO:2, wherein the nucleic acid encoding the immunogenic composition is operably linked to a heterologous regulatory nucleic acid sequence, and wherein the heterologous regulatory nucleic acid sequence includes a promoter.

Host cells are provided according to aspects of the present invention which include a recombinant expression construct, wherein the recombinant expression construct includes a nucleic acid encoding an immunogenic composition, wherein the immunogenic composition includes a protein which protein has, or includes, the amino acid sequence of SEQ ID NO:2, and wherein the nucleic acid encoding the immunogenic composition is operably linked to a heterologous regulatory nucleic acid sequence.

Host cells are provided according to aspects of the present invention which include a recombinant expression construct, wherein the recombinant expression construct includes a nucleic acid encoding an immunogenic composition, wherein the immunogenic composition includes a protein which has, or includes, the amino acid sequence of SEQ ID NO:2, wherein the nucleic acid encoding the immunogenic composition is operably linked to a heterologous regulatory nucleic acid sequence, and wherein the heterologous regulatory nucleic acid sequence includes a promoter.

Host cells are provided according to aspects of the present invention which include a recombinant expression construct in an expression vector, wherein the recombinant expression construct includes a nucleic acid encoding an immunogenic composition, wherein the immunogenic composition includes a protein which has, or includes, the amino acid sequence of SEQ ID NO:2, and wherein the nucleic acid encoding the immunogenic composition is operably linked to a heterologous regulatory nucleic acid sequence.

Host cells are provided according to aspects of the present invention which include a recombinant expression construct in an expression vector, wherein the recombinant expression construct includes a nucleic acid encoding an immunogenic composition, wherein the immunogenic composition includes a protein which has, or includes, the amino acid sequence of SEQ ID NO:2, wherein the nucleic acid encoding the immunogenic composition is operably linked to a heterologous regulatory nucleic acid sequence, and wherein the heterologous regulatory nucleic acid sequence includes a promoter.

Methods of treatment or prevention of a HER2+ cancer in a subject are provided according to aspects of the present invention which include administering a therapeutically effective amount of an immunogenic composition to the subject, wherein the immunogenic composition includes a protein which has, or includes, the amino acid sequence of SEQ ID NO:2.

Methods of treatment or prevention of a HER2+ cancer in a subject are provided according to aspects of the present invention which include administering a therapeutically effective amount of an immunogenic composition to the subject, wherein the immunogenic composition includes a protein which has, or includes, the amino acid sequence of SEQ ID NO:2, and wherein the composition includes a pharmaceutically acceptable carrier.

Methods of treatment or prevention of a HER2+ cancer in a subject are provided according to aspects of the present invention which include administering a therapeutically effective amount of an immunogenic composition to the subject, wherein the immunogenic composition includes a protein which has, or includes, the amino acid sequence of SEQ ID NO:2, and wherein the composition includes an adjuvant.

Methods of treatment or prevention of a HER2+ cancer in a subject are provided according to aspects of the present invention which include administering a therapeutically effective amount of an immunogenic composition to the subject, wherein the immunogenic composition includes a protein a protein which has, or includes, the amino acid sequence of SEQ ID NO:2, and wherein the composition includes an immunostimulating adjuvant.

Methods of treatment or prevention of a HER2+ cancer in a subject are provided according to aspects of the present invention which include administering a therapeutically effective amount of an immunogenic composition to the subject, wherein the immunogenic composition includes an expression construct encoding a protein which has, or includes, the amino acid sequence of SEQ ID NO:2. According to aspects of the present invention, the expression construct includes a nucleic acid encoding the amino acid sequence of SEQ ID NO:2 operably linked to a heterologous regulatory nucleic acid sequence.

Methods of treatment or prevention of a HER2+ cancer in a subject are provided according to aspects of the present invention which include administering a therapeutically effective amount of an immunogenic composition to the subject, wherein the immunogenic composition includes an expression construct encoding a protein which has, or includes, the amino acid sequence of SEQ ID NO:2. According to aspects of the present invention, the expression construct includes a nucleic acid encoding the amino acid sequence of SEQ ID NO:2 operably linked to a heterologous regulatory nucleic acid sequence, wherein the heterologous regulatory nucleic acid sequence is a promoter.

Methods of treatment or prevention of a HER2+ cancer in a subject are provided according to aspects of the present invention which include administering a therapeutically effective amount of an immunogenic composition to the subject, wherein the immunogenic composition includes an expression vector including an expression construct, the expression construct encoding a protein which has, or includes, the amino acid sequence of SEQ ID NO:2

Methods of treatment or prevention of a HER2+ cancer in a subject are provided according to aspects of the present invention which include administering a therapeutically effective amount of an immunogenic composition to the subject, wherein the immunogenic composition includes an expression vector, wherein the expression vector includes an expression construct encoding a protein which has, or includes, the amino acid sequence of SEQ ID NO:2. According to aspects of the present invention, the expression construct includes a nucleic acid encoding the amino acid sequence of SEQ ID NO:2 operably linked to a heterologous regulatory nucleic acid sequence.

Methods of treatment or prevention of a HER2+ cancer in a subject are provided according to aspects of the present invention which include administering a therapeutically effective amount of an immunogenic composition to the subject, wherein the immunogenic composition includes an expression vector, wherein the expression vector includes an expression construct encoding a protein which has, or includes, the amino acid sequence of SEQ ID NO:2. According to aspects of the present invention, the expression construct includes a nucleic acid encoding the amino acid sequence of SEQ ID NO:2 operably linked to a heterologous regulatory nucleic acid sequence, wherein the heterologous regulatory nucleic acid sequence is a promoter.

Methods of generating an immunogenic composition effective to stimulate immune activity against a tumor-associated self-antigen are provided according to aspects of the present invention which include: identifying a reference sequence; identifying at least a first amino acid sequence homologous to the reference sequence, wherein the reference sequence and the first amino acid sequence homologous to the reference sequence are not identical; comparing the homologous amino acid sequence and the reference sequence to identify at least a first difference between the homologous amino acid sequence and the reference sequence at a first position in the reference sequence and a corresponding first position in the homologous amino acid sequence; assigning a BLOSUM62 score to the first difference between the homologous amino acid sequence and the reference sequence, wherein the score represents a probability of substitution of an amino acid at the first position of the reference sequence with the amino acid at the corresponding first position in the homologous sequence, wherein the score falls within a numerical probability range of −4 to +3, where −4 is a number which indicates an extremely non-conservative substitution of the amino acid at the first position of the reference sequence with the amino acid at the corresponding first position of the homologous sequence such that the occurrence of substitution of the extremely non-conservative substitution is relatively rare or unlikely, where +3 is a number which indicates an extremely conservative substitution of the amino acid at the first position of the reference sequence with the amino acid at the corresponding first position of the homologous sequence such that the occurrence of substitution of the extremely non-conservative substitution is relatively frequent or likely, where a BLOSUM score of 0 indicates neutrality such that the occurrence of substitution has an equal probability; and synthesizing a new amino acid sequence identical to the reference amino acid sequence with the proviso that that the new amino acid sequence has at least one substitution at the first position with an amino acid present at the corresponding first position in the homologous amino acid sequence where the score assigned to the first difference is in the range of 0 to 1 and indicates neutrality such that the occurrence of substitution has an equal probability, thereby generating an immunogenic composition.

Methods of generating an immunogenic composition effective to stimulate immune activity against a tumor-associated self-antigen are provided according to aspects of the present invention which include: identifying a reference sequence; identifying at least 2, at least 3, at least 4, at least 5, at least 6, at least 7, at least 8, at least 9, at least 10, at least 11, at least 12, at least 13, at least 14, or at least 15, amino acid sequences homologous to the reference sequence and comparing them with the reference amino acid sequence, wherein the reference sequence and the sequences homologous to the reference sequence are not identical; comparing the homologous amino acid sequences and the reference sequence to identify at least a first difference between at least two or more of the homologous amino acid sequences and the reference sequence at a first position in the reference sequence and a corresponding first position in the homologous amino acid sequences; assigning a BLOSUM62 score to the first difference between the homologous amino acid sequences and the reference sequence, wherein the score represents a probability of substitution of an amino acid at the first position of the reference sequences with the amino acid at the corresponding first position in the homologous sequence, wherein the score falls within a numerical probability range of −4 to +3, where −4 is a number which indicates an extremely non-conservative substitution of the amino acid at the first position of the reference sequence with the amino acid at the corresponding first position of the homologous sequences such that the occurrence of substitution of the extremely non-conservative substitution is relatively rare or unlikely, where +3 is a number which indicates an extremely conservative substitution of the amino acid at the first position of the reference sequence with the amino acid at the corresponding first position of the homologous sequences such that the occurrence of substitution of the extremely non-conservative substitution is relatively frequent or likely, where a BLOSUM score of 0 indicates neutrality such that the occurrence of substitution has an equal probability; and synthesizing a new amino acid sequence identical to the reference amino acid sequence with the proviso that that the new amino acid sequence has at least one substitution at the first position with an amino acid present at the corresponding first position in the homologous amino acid sequences where the score assigned to the first difference is in the range of 0 to 1 and indicates neutrality such that the occurrence of substitution has an equal probability, thereby generating an immunogenic composition.

Methods of generating an immunogenic composition effective to stimulate immune activity against a tumor-associated self-antigen are provided according to aspects of the present invention which include: identifying a reference sequence; identifying at least a first amino acid sequence homologous to the reference sequence, wherein the reference sequence and the first amino acid sequence homologous to the reference sequence are not identical; comparing the homologous amino acid sequence and the reference sequence to identify at least 2, at least 3, at least 4, at least 5, at least 6, at least 7, at least 8, at least 9, at least 10, at least 11, at least 12, at least 13, at least 14, at least 15, or more, differences between the homologous amino acid sequence and the reference sequence at corresponding 2nd, 3rd, 4th, 5th, 6th, 7th, 8th, 9th, 10th, 11th, 12th, 13th, 14th, 15th or more, positions in the reference sequence and corresponding positions in the homologous amino acid sequence, assigning a BLOSUM score to the at least 2, at least 3, at least 4, at least 5, at least 6, at least 7, at least 8, at least 9, at least 10, at least 11, at least 12, at least 13, at least 14, at least 15, or more, differences between the homologous amino acid sequence and the reference sequence at corresponding 2nd, 3rd, 4th, 5th, 6th, 7th, 8th, 9th, 10th, 11th, 12th, 13th, 14th, 15th or more, positions in the reference sequence and corresponding positions in the homologous amino acid, wherein the BLOSUM score represents a probability of substitution of an amino acid at the 2nd, 3rd, 4th, 5th, 6th, 7th, 8th, 9th, 10th, 11th, 12th, 13th, 14th, 15th or more, positions of the reference sequence with the amino acid at the corresponding 2nd, 3rd, 4th, 5th, 6th, 7th, 8th, 9th, 10th, 11th, 12th, 13th, 14th, 15th or more, positions in the homologous sequence, wherein the score falls within a numerical probability range of −4 to +3, where −4 is a number which indicates an extremely non-conservative substitution of the amino acid at the 2nd, 3rd, 4th, 5th, 6th, 7th, 8th, 9th, 10th, 11th, 12th, 13th, 14th, 15th or more, positions of the reference sequence with the amino acid at the corresponding 2nd, 3rd, 4th, 5th, 6th, 7th, 8th, 9th, 10th, 11th, 12th, 13th, 14th, 15th or more, positions of the homologous sequence such that the occurrence of substitution of the extremely non-conservative substitution is relatively rare or unlikely, where +3 is a number which indicates an extremely conservative substitution of the amino acid at the 2nd, 3rd, 4th, 5th, 6th, 7th, 8th, 9th, 10th, 11th, 12th, 13th, 14th, 15th or more, positions of the reference sequence with the amino acid at the corresponding 2nd, 3rd, 4th, 5th, 6th, 7th, 8th, 9th, 10th, 11th, 12th, 13th, 14th, 15th or more, positions of the homologous sequence such that the occurrence of substitution of the extremely non-conservative substitution is relatively frequent or likely, where a BLOSUM score of 0 indicates neutrality such that the occurrence of substitution has an equal probability; and synthesizing a new amino acid sequence identical to the reference amino acid sequence with the proviso that that the new amino acid sequence has at least one substitution at the 2nd, 3rd, 4th, 5th, 6th, 7th, 8th, 9th, 10th, 11th, 12th, 13th, 14th, 15th or more, positions with an amino acid present at the corresponding 2nd, 3rd, 4th, 5th, 6th, 7th, 8th, 9th, 10th, 11th, 12th, 13th, 14th, 15th or more, positions in the homologous amino acid sequence where the score assigned to the 2nd, 3rd, 4th, 5th, 6th, 7th, 8th, 9th, 10th, 11th, 12th, 13th, 14th, 15th or more, positions is in the range of 0 to 1 and indicates neutrality such that the occurrence of substitution has an equal probability, thereby generating an immunogenic composition effective to stimulate immune activity against a tumor-associated self-antigen, effective to overcome self-tolerance of the tumor-associated self-antigen, and characterized by substantial similarity to the native three dimensional structure of the tumor-associated self-antigen.

According to aspects of the present invention, at least 2, at least 3, at least 4, at least 5, at least 6, at least 7, at least 8, at least 9, at least 10, at least 11, at least 12, at least 13, at least 14, or at least 15, substitutions are made in the reference amino acid sequence at 2nd, 3rd, 4th, 5th, 6th, 7th, 8th, 9th, 10th, 11th, 12th, 13th, 14th, 15th or more, positions in the reference sequence with an amino acid present at the corresponding 2nd, 3rd, 4th, 5th, 6th, 7th, 8th, 9th, 10th, 11th, 12th, 13th, 14th, 15th or more, positions in the homologous amino acid sequence where the BLOSUM score assigned to the differences identified at the 2nd, 3rd, 4th, 5th, 6th, 7th, 8th, 9th, 10th, 11th, 12th, 13th, 14th, 15th or more, positions is in the range of 0 to 1.

Methods of generating an immunogenic composition effective to stimulate immune activity against a tumor-associated self-antigen are provided by the present invention which include identifying a reference sequence; identifying at least a first amino acid sequence homologous to the reference sequence, wherein the reference sequence and the first amino acid sequence homologous to the reference sequence are not identical; comparing the homologous amino acid sequence and the reference sequence to identify at least a first difference between the homologous amino acid sequence and the reference sequence at a first position in the reference sequence and a corresponding first position in the homologous amino acid sequence; assigning a score to the first difference between the homologous amino acid sequence and the reference sequence, wherein the score represents a probability of substitution of an amino acid at the first position of the reference sequence with the amino acid at the corresponding first position in the homologous sequence, wherein the score falls within a numerical probability range of x to y, where x is a number which indicates an extremely non-conservative substitution of the amino acid at the first position of the reference sequence with the amino acid at the corresponding first position of the homologous sequence such that the occurrence of substitution of the extremely non-conservative substitution is relatively rare or unlikely, where y is a number which indicates an extremely conservative substitution of the amino acid at the first position of the reference sequence with the amino acid at the corresponding first position of the homologous sequence such that the occurrence of substitution of the extremely non-conservative substitution is relatively frequent or likely, where a number intermediate between x and y indicates neutrality such that the occurrence of substitution has an equal probability; synthesizing a new amino acid sequence identical to the reference amino acid sequence with the proviso that that the new amino acid sequence has at least one substitution at the first position with an amino acid present at the corresponding first position in the homologous amino acid sequence where the score assigned to the first difference is intermediate between x and y indicates neutrality such that the occurrence of substitution has an equal probability, thereby generating an immunogenic composition.

According to aspects of inventive methods, at least 2, at least 3, at least 4, at least 5, at least 6, at least 7, at least 8, at least 9, at least 10, at least 11, at least 12, at least 13, at least 14, or at least 15, amino acid sequences homologous to the reference sequence are identified and compared with the reference amino acid sequence.

According to aspects of inventive methods, at least 2, at least 3, at least 4, at least 5, at least 6, at least 7, at least 8, at least 9, at least 10, at least 11, at least 12, at least 13, at least 14, at least 15, or more, differences between the homologous amino acid sequence and the reference sequence at corresponding $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$ or more, positions in the reference sequence and a corresponding position in the homologous amino acid sequence are identified and assigned a score.

According to aspects of inventive methods, at least 2, at least 3, at least 4, at least 5, at least 6, at least 7, at least 8, at least 9, at least 10, at least 11, at least 12, at least 13, at least 14, or at least 15, substitutions are made in the reference amino acid sequence at $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$ or more, positions in the reference sequence with an amino acid present at the corresponding $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$ or more, positions in the homologous amino acid sequence where the score assigned to the differences identified at the $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$ or more, positions is intermediate between x and y indicating that the occurrence of substitution has an equal probability.

BRIEF DESCRIPTION OF THE DRAWINGS

FIG. 1A is a schematic diagram showing HER2 ECD subdomains I-IV and mAbs reactive to each subdomain. Signal peptide (SP) and transmembrane domain (TM), are indicated.

FIG. 1B shows graphs of BLOSUM62 scores plotted for amino acid residues of indicated HER2 vaccines; for amino acid substitutions, BLOSUM scores are calculated relative to human HER2 (top row). pE2TM is wt HER2 (amino acid residues 1-687). pE2Neu contains wt HER2 SP and subdomains I & II (residues 1-390), fused to rat Neu (residues 394-691), with AEF inserted into subdomain III. pNeuE2 is the converse of pE2Neu, containing Neu SP and subdomains I & II, fused to HER2 (residues 391-687).

FIG. 1C is a graph showing results in BALB HER2 Tg mice which received three DNA electrovaccinations with pE2TM, pNeu, the hybrid vaccines pE2Neu, pNeuE2, or admixed pE2TM and pNeu. The levels of anti-Neu or anti-HER2 Ab in the immune sera were measured by flow cytometry. There were 6-9 mice per group.

FIGS. 2Ai, 2Aii, 2B, 2C, 2D, 2E, 2F, and 2G generally show human HER2 point mutants: stability and immunogenicity in vitro and in vivo.

FIG. 2Ai is an image showing single residue substitutions depicted on the DNA scheme of human HER2.

FIG. 2Aii is an image showing single residue substitutions depicted on the space-filling model (RCSB 2A91, JSmol viewer) of human HER2.

FIG. 2D shows results obtained when mice were electrovaccinated twice with pE2TM, pE2Neu, pE2TM-Q141K, or pE2TM-Q429R. In BALB HER-2 Tg mice, HER2 antibody levels were measured by flow cytometry following each vaccination and IFN-γ producing SC were measured after two vaccinations using 3T3/EKB cells as the APC (with 3T3/KB as controls). There were 4-6 mice per group. *$p<0.05$ FIG. 2E shows results obtained when mice were electrovaccinated twice with pE2TM, pE2Neu, pE2TM-Q141K, or pE2TM-Q429R. In B6 HER-2 Tg mice, Treg were depleted 10 days prior to vaccination. HER2 Ab levels were measured by flow cytometry while IFNγ-producing SC were measured with the APC TC-1/E2, with TC-1 as controls. There were 4-6 mice per group. *$p<0.05$ FIG. 2F shows results obtained when mice were electrovaccinated twice with pE2TM, pE2Neu, pE2TM-Q141K, or pE2TM-Q429R. In BALB HER-2 Tg mice, HER2 antibody levels were measured by flow cytometry following each vaccination and IFN-γ producing SC were measured after two vaccinations using 3T3/EKB cells as the APC (with 3T3/KB as controls). There were 4-6 mice per group. *$p<0.05$ FIG. 2G shows results obtained when mice were electrovaccinated twice with pE2TM, pE2Neu, pE2TM-Q141K, or pE2TM-Q429R. In B6 HER-2 Tg mice, Treg were depleted 10 days prior to vaccination. HER2 Ab levels were measured by flow cytometry while IFNγ-producing SC were measured with the APC TC-1/E2, with TC-1 as controls. There were 4-6 mice per group. *p<0.05

FIGS. 3A and 3B are schematic diagrams in which positions of amino acid (AA) substitutions are depicted. Shaded substitutions are unique to rhesus monkey (XP_001090430). pE2TM is human HER2; ph(es)E2TM is pE2TM with the indicated 5 AA substitutions; prmE2TM is rhesus monkey HER2.

FIG. 3C is a set of graphs showing expression of recombinant proteins. 3T3 cells were transfected with ph(es) E2TM or prmE2TM and analyzed by flow cytometry. pE2TM and pVax blank vector were controls; positive cells are gated.

FIGS. 3D and 3E are graphs showing induction of HER2 specific response by the test vaccine constructs. BALB HER2 Tg mice were electrovaccinated twice with pE2TM, ph(es)E2TM or prmE2TM. HER2 specific antibody (Ab) (FIG. 3D) and IFN-γ producing SC were measured after the last vaccination. There were 4 mice per group. *p<0.05

FIG. 5A shows the binding profile of immune sera from BALB HER2 and B6 HER2 Tg mice vaccinated with pVax, pE2TM, pE2Neu or ph(es)E2TM. $p95_{355}$LPESFDGDPASNTAP$_{369}$ (SEQ ID NO:40) was recognized most prominently by pE2Neu and ph(es)E2TM immune sera. Results for p93 (SEQ ID NO:41); p94 SEQ ID NO:42); p96 (SEQ ID NO:43); and p97 (SEQ ID NO:44); are shown.

FIG. 5B is an image showing position of cognate peptide domain p95 (SEQ ID NO:40) indicated in the ribbon model of human HER) (RCSB 2A91, JSmol viewer). Three extra residues AEF introduced during pE2Neu construction are located between residues 368-369 within p95 (SEQ ID NO:46).

FIG. 6A is a graph showing inhibition of SK-BR-3 tumor cell proliferation in vitro. Cells were incubated with increasing concentrations of HER2 binding Ab from vaccinated BALB HER2 Tg mice shown in FIG. 4. The negative control was pVax immune serum; and the positive control was Gefitinib. Cell viability was measured by Alamar Blue assay. Values are means±SE from three independent samples, each in triplicate, and normalized to untreated cells. Statistical significance was determined by Student's t test.

FIG. 6B is a graph of results of tumor growth inhibition after BALB HER2Tg mice were vaccinated twice either with pE2TM, pE2Neu or ph(es)E2TM, at 2 week intervals. D2F2/E2t cells were injected intra-fat pad and tumor growth was monitored twice weekly. *p<0.05, p<0.01, *p<0.0001

DETAILED DESCRIPTION OF THE INVENTION

Figures 1A, 1B:
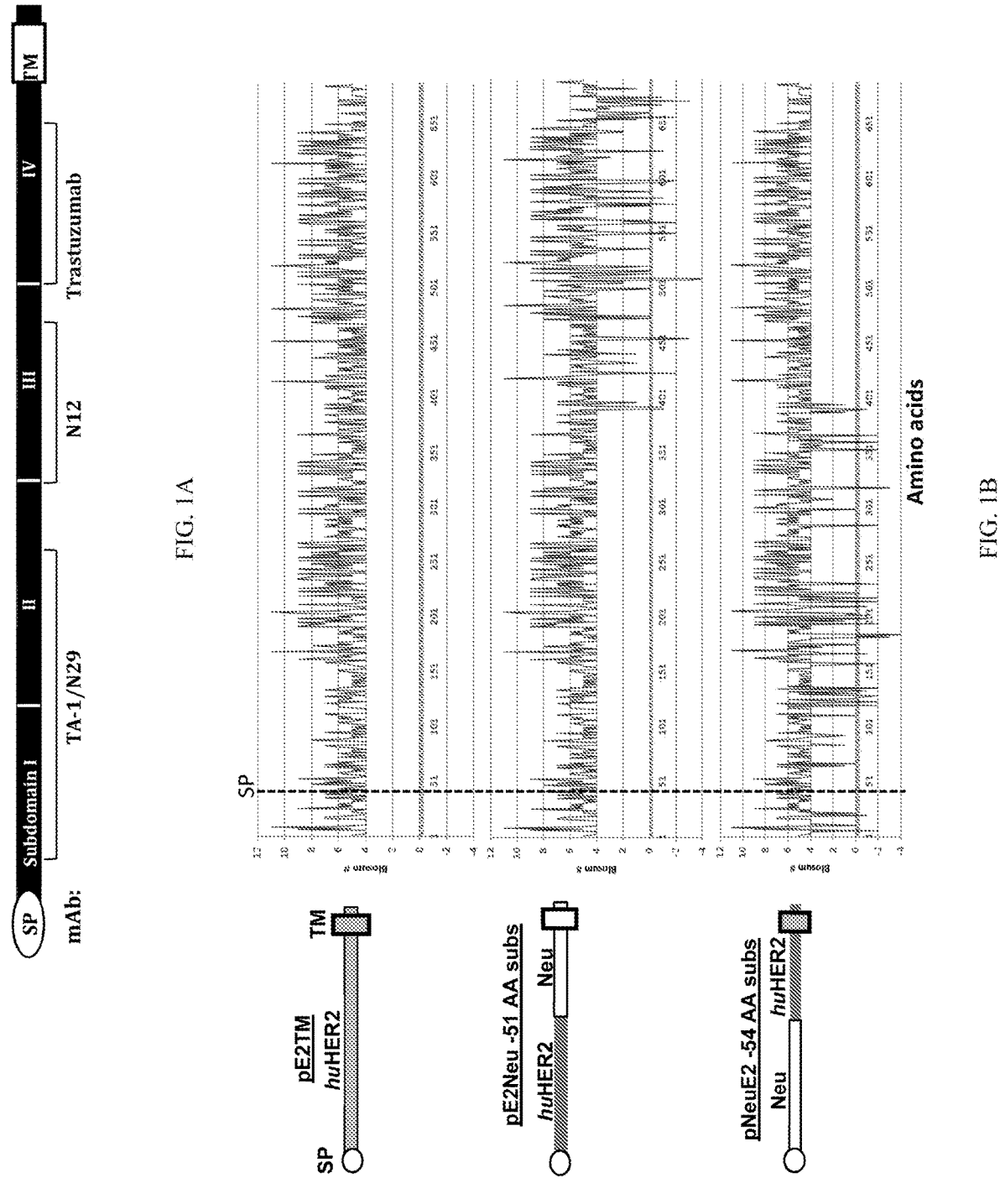
FIGS. 1A and 1B generally show aspects of HER2 vaccines and BLOSUM scores.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, PA, 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808; Chu, E. and Devita, V. T., Eds., Physicians' Cancer Chemotherapy Drug Manual, Jones & Bartlett Publishers, 2005; J. M. Kirkwood et al., Eds., Current Cancer Therapeutics, 4th Ed., Current Medicine Group, 2001; Remington: The Science and Practice of Pharmacy, Lippincott Williams & Wilkins, 21st Ed., 2005; L. V. Allen, Jr. et al., Ansel's Pharmaceutical Dosage Forms and Drug Delivery Systems, 8th Ed., Philadelphia, PA: Lippincott, Williams & Wilkins, 2004; and L. Brunton et al., Goodman & Gilman's The Pharmacological Basis of Therapeutics, McGraw-Hill Professional, 12th Ed., 2011.

The singular terms "a," "an," and "the" are not intended to be limiting and include plural referents unless explicitly stated otherwise or the context clearly indicates otherwise.

Immunogenic compositions are provided according to the present invention which include a protein effective to stimulate immune activity against HER2, human HER2, a tumor-associated self-antigen, or a variant of any thereof which is a tumor-associated self-antigen.

According to aspects of the present invention, immunogenic compositions are provided which include a protein effective to stimulate immune activity against human HER2 of SEQ ID NO:1, a tumor-associated self-antigen.

According to aspects of the present invention, immunogenic compositions are provided which include a protein effective to stimulate immune activity against a variant of human HER2 of SEQ ID NO:1 which is a tumor-associated self-antigen.

According to aspects of the present invention, immunogenic compositions are provided which include a protein effective to stimulate immune activity against human HER2 of SEQ ID NO:16, a tumor-associated self-antigen.

According to aspects of the present invention, immunogenic compositions are provided which include a protein effective to stimulate immune activity against a variant human HER2 of SEQ ID NO:16 which is a tumor-associated self-antigen.

Immunogenic compositions are provided according to aspects of the present invention which include a protein effective to stimulate immune activity against a non-human HER2 which is a tumor-associated self-antigen, such as a canine HER2 or feline HER2.

Immunogenic compositions are provided according to aspects of the present invention which include the protein of SEQ ID NO:2 which is characterized by 5 amino acid substitutions compared to the wild-type human HER2 protein of SEQ ID NO:1, namely, M198V, Q398R, F425L, H473R, and A622T. Optionally, one or more additional amino acids maybe added to the N-terminus, C-terminus, or both the N-terminus and C-terminus, such as 1, 2, 3, 4, 5, 6, 7, 8, 9, 10, 11, 12, 13, 14, 15, 16, 17, 18, 19, or 20 amino acids, with the proviso that the cytoplasmic domain of the wild-type HER2 is not present in an immunogenic composition of the present invention.

Immunogenic compositions are provided according to aspects of the present invention which include the protein of SEQ ID NO:17 which is characterized by 5 amino acid substitutions compared to the wild-type human HER2 protein of SEQ ID NO:1, namely, M198V, Q398R, F425L, H473R, and A622T. Optionally, one or more additional amino acids maybe added to the N-terminus, C-terminus, or both the N-terminus and C-terminus, such as 1, 2, 3, 4, 5, 6, 7, 8, 9, 10, 11, 12, 13, 14, 15, 16, 17, 18, 19, or 20 amino acids, with the proviso that the cytoplasmic domain of the wild-type HER2 is not present in an immunogenic composition of the present invention.

Immunogenic compositions are provided according to aspects of the present invention which include a protein having the amino acid sequence selected from the group consisting of: SEQ ID NO:2, SEQ ID NO:17, SEQ ID NO:19, and SEQ ID NO:22; or a variant of any thereof. Optionally, one or more additional amino acids maybe added to the N-terminus, C-terminus, or both the N-terminus and C-terminus, such as 1, 2, 3, 4, 5, 6, 7, 8, 9, 10, 11, 12, 13, 14, 15, 16, 17, 18, 19, or 20 amino acids, with the proviso that the cytoplasmic domain of the wild-type HER2 is not present in an immunogenic composition of the present invention.

According to aspects of the present invention, immunogenic compositions are provided which include an immunogenic tumor-associated self-antigen characterized by one or more of: 1) effectiveness to stimulate immune activity against a specified tumor-associated self-antigen in a subject, 2) effectiveness to overcome self-tolerance of the specified tumor-associated self-antigen, and 3) substantial similarity to the native three dimensional structure of the specified tumor-associated self-antigen.

According to aspects of the present invention, immunogenic compositions are provided which include an immunogenic HER2 characterized by one or more of: 1) effectiveness to stimulate immune activity against HER2 in a subject, 2) effectiveness to overcome self-tolerance of HER2, and 3) substantial similarity to the native three-dimensional structure of HER2.

According to aspects of the present invention, immunogenic compositions are provided which include an immunogenic human HER2 characterized by one or more of: 1) effectiveness to stimulate immune activity against human HER2 in a subject, 2) effectiveness to overcome self-tolerance of human HER2, and 3) substantial similarity to the native three-dimensional structure of human HER2.

According to aspects of the present invention, immunogenic compositions are provided which include an immunogenic human HER2 of SEQ ID NO:2 characterized by one or more of: 1) effectiveness to stimulate immune activity against human HER2 of SEQ ID NO:1 in a subject, 2) effectiveness to overcome self-tolerance of human HER2 of SEQ ID NO:1, and 3) substantial similarity to the native three dimensional structure of human HER2 of SEQ ID NO:1.

According to aspects of the present invention, immunogenic compositions are provided which include an immunogenic variant of the human HER2 of SEQ ID NO:2 characterized by one or more of: 1) effectiveness to stimulate immune activity against the variant of human HER2 of SEQ ID NO:1 in a subject, 2) effectiveness to overcome self-tolerance of the variant of the human HER2 of SEQ ID NO:1, and 3) substantial similarity to the native three-dimensional structure of the variant of the human HER2 of SEQ ID NO:1.

According to aspects of the present invention, immunogenic compositions are provided which include an immunogenic human HER2 of SEQ ID NO:17 characterized by one or more of: 1) effectiveness to stimulate immune activity against human HER2 of SEQ ID NO:16 in a subject, 2) effectiveness to overcome self-tolerance of the human HER2 of SEQ ID NO:16, and 3) substantial similarity to the native three-dimensional structure of the human HER2 of SEQ ID NO:16.

According to aspects of the present invention, immunogenic compositions are provided which include an immunogenic variant of human HER2 of SEQ ID NO:17 characterized by one or more of: 1) effectiveness to stimulate immune activity against the variant of human HER2 of SEQ ID NO:16 in a subject, 2) effectiveness to overcome self-tolerance of the variant of the human HER2 of SEQ ID NO:16, and 3) substantial similarity to the native three-dimensional structure of the variant of the human HER2 of SEQ ID NO:16.

As used herein, the term "variant" refers to a variation of a nucleic acid sequence, a variation of a nucleic acid sequence encoding a protein, or a variation of a protein in which one or more nucleotides or amino acid residues have been modified by nucleotide or amino acid substitution, addition, or deletion while retaining all, or at least some, of the function of the reference nucleic acid sequence or protein. Variants of a nucleic acid sequence or protein described herein are characterized by conserved functional properties compared to the corresponding nucleic acid sequence or protein.

Mutations can be introduced using standard molecular biology techniques, such as chemical synthesis, site-directed mutagenesis and PCR-mediated mutagenesis.

One of skill in the art will recognize that one or more amino acid mutations can be introduced without altering the functional properties of a desired protein. For example, one or more amino acid substitutions, additions, or deletions can be made without altering the functional properties of a desired protein.

Biological activity of a protein variant is readily determined by one of skill in the art, for instance using any of the functional assays described herein or other functional assays known in the art.

Variants of a protein described herein are characterized by conserved functional properties compared to the corresponding protein and have 75%, 80%, 85%, 90%, 95%, 96%, 97%, 98%, 99% or greater identity to the amino acid sequence of a reference protein.

Variants of SEQ ID NO:2 are provided according to aspects of the present invention in which M198 is substituted by any of: V, A, H, L, I, Q, or F; Q398 is substituted by any of: R, H, E, K, N, D, H, M, or S; F425 is substituted by any of: L, Y, W, I, or M; H473 is substituted by any of: R, Y, N, Q, or E; and A622 is substituted by any of: T, S, C, G, V, or M. Optionally, one or more additional amino acids maybe added to the N-terminus, C-terminus, or both the N-terminus and C-terminus, such as 1, 2, 3, 4, 5, 6, 7, 8, 9, 10, 11, 12, 13, 14, 15, 16, 17, 18, 19, or 20 amino acids, with the proviso that the cytoplasmic domain of the wild-type HER2 is not present in an immunogenic composition of the present invention.

Variants of SEQ ID NO:17 are provided according to aspects of the present invention in which M198 is substituted by any of: V, A, H, L, I, Q, or F; Q398 is substituted by any of: R, H, E, K, N, D, H, M, or S; F425 is substituted by any of: L, Y, W, I, or M; H473 is substituted by any of: R, Y, N, Q, or E; and A622 is substituted by any of: T, S, C, G, V, or M. Optionally, one or more additional amino acids maybe added to the N-terminus, C-terminus, or both the N-terminus and C-terminus, such as 1, 2, 3, 4, 5, 6, 7, 8, 9, 10, 11, 12, 13, 14, 15, 16, 17, 18, 19, or 20 amino acids, with the proviso that the cytoplasmic domain of the wild-type HER2 is not present in an immunogenic composition of the present invention.

A variant can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

An immunogenic composition of the present invention can be administered to a subject alone or as part of a pharmaceutical composition. Inventive compositions are suitable for administration to subjects by a variety of routes including systemic and local routes of administration. Inventive compositions are suitable for administration to subjects by a variety of routes illustratively including intravenous, oral, parenteral, intramuscular, subcutaneous and mucosal. Inventive compositions are suitable for administration to subjects by a variety of routes illustratively including but not limited to, oral, rectal, nasal, pulmonary, epidural, ocular, otic, intraarterial, intracardiac, intracerebroventricular, intradermal, intravenous, intramuscular, intraperitoneal, intraosseous, intrathecal, intravesical, subcutaneous, topical, transdermal, and transmucosal, such as by sublingual, buccal, vaginal, and inhalational, routes of administration.

Optionally, an immunogenic composition according to aspects of the present invention includes a pharmaceutically acceptable carrier.

Optionally, an immunogenic composition according to aspects of the present invention includes an adjuvant.

The term "pharmaceutically acceptable" refers to a material which can be administered to a subject along with an inventive immunogenic composition without causing significant undesirable biological effects and without interacting in a deleterious manner with any other component of the immunogenic composition. An immunogenic composition including a pharmaceutically acceptable carrier is also termed a "pharmaceutical composition" herein.

Pharmaceutical compositions suitable for administration illustratively include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers; diluents; solvents; or vehicles include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants.

Compositions suitable for injection optionally include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

Pharmaceutical compositions according to the present invention may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of an injectable pharmaceutical form can be brought about by the use of agents delaying absorption, for example, aluminum monostearate and gelatin.

Further exemplary adjuvants include immunostimulating adjuvants such as Freund's complete adjuvant; Freund's incomplete adjuvant; aluminum hydroxide such as commercially available as Alhydrogel, Accurate Chemical & Scientific Co, Westbury, New York; and Gerbu adjuvant, available from C-C Biotech, Poway, California.

Solid dosage forms for oral administration include capsules, tablets, pills, powders, and granules. In such solid dosage forms, an inventive conjugate is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alginates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Microencapsulated formulations of inventive immunogenic compositions are also contemplated.

Liquid dosage forms for oral administration include pharmaceutically acceptable emulsions, solutions, suspensions, syrups, and elixirs. In addition to a conjugate according to the present invention, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, a pharmaceutical composition according to the present invention can also include adjuvants, such as wetting agents, emulsifying and suspending agents, sweetening, flavoring, and perfuming agents.

Suspensions, in addition to an inventive conjugate, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Further specific details of pharmaceutical formulation can be found in Pharmaceutical Dosage Forms: Tablets, eds. H. A. Lieberman et al., New York: Marcel Dekker, Inc., 1989; L. V. Allen, Jr. et al., Ansel's Pharmaceutical Dosage Forms and Drug Delivery Systems, 8th Ed., Philadelphia, PA, Lippincott, Williams & Wilkins, 2004; and Remington, The Science and Practice of Pharmacy, $21^{st}$ ed., Lippincott, Williams & Wilkins, Philadelphia, PA, 2006.

An inventive immunogenic composition is optionally delivered in conjunction with an additional therapeutic agent according to aspects of the present invention. A therapeutic agent suitable in this regard illustratively includes an analgesic, an antibiotic, an anti-inflammatory, an anti-cancer agent, an antiviral, a gamma or beta radiation emitting species, an enzyme, and a hormone. In addition, two or more additional therapeutic agents may be administered to a subject.

Recombinant expression constructs are provided according to aspects of the present invention which include a nucleic acid encoding a protein effective to stimulate immune activity against tumor-associated self-antigen, operably linked to a heterologous regulatory nucleic acid sequence.

Recombinant expression constructs are provided according to aspects of the present invention which include a nucleic acid encoding a protein effective to stimulate immune activity against HER2, operably linked to a heterologous regulatory nucleic acid sequence.

Recombinant expression constructs are provided according to aspects of the present invention which include a nucleic acid encoding a protein effective to stimulate immune activity against human HER2, operably linked to a heterologous regulatory nucleic acid sequence.

Recombinant expression constructs are provided according to aspects of the present invention which include a nucleic acid encoding a protein including the amino acid sequence of SEQ ID NO:2, or a variant thereof, operably linked to a heterologous regulatory nucleic acid sequence. According to aspects of the present invention, a nucleic acid encoding a protein including the amino acid sequence of SEQ ID NO:2 is the nucleic acid of SEQ ID NO:25

It is appreciated that due to the degenerate nature of the genetic code, alternate nucleic acid sequences encode a specified protein, and that such alternate nucleic acids may be expressed to produce the desired protein. Thus, variants of SEQ ID NO:25 which encode SEQ ID NO:2 are provided according to aspects of the present invention.

Recombinant expression constructs are provided according to aspects of the present invention which include a nucleic acid encoding a protein including the amino acid sequence of SEQ ID NO:17, or a variant thereof, operably linked to a heterologous regulatory nucleic acid sequence. According to aspects of the present invention, a nucleic acid encoding a protein including the amino acid sequence of SEQ ID NO:17 is the nucleic acid of SEQ ID NO:27

It is appreciated that due to the degenerate nature of the genetic code, alternate nucleic acid sequences encode a specified protein, and that such alternate nucleic acids may be expressed to produce the desired protein. Thus, variants of SEQ ID NO:27 which encode SEQ ID NO:17 are provided according to aspects of the present invention.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide and is usually shown as the ordering of the sense strand.

The term "expression construct" is used herein to refer to a double-stranded recombinant DNA molecule containing a desired nucleic acid coding sequence for a protein to be expressed and containing one or more regulatory elements necessary or desirable for the expression of the operably linked coding sequence. The terms "expressed" and "expression" refer to transcription of a nucleic acid sequence to produce a corresponding mRNA and/or translation of the mRNA to produce the corresponding protein. Expression constructs can be generated recombinantly or by DNA synthesis using well-known methodology.

The term "recombinant" is used to indicate a nucleic acid construct in which two or more nucleic acids are linked and which are not found linked in nature.

The term "regulatory element" as used herein refers to a nucleotide sequence which controls some aspect of the expression of nucleic acid sequences. Exemplary regulatory elements illustratively include an enhancer, an internal ribosome entry site (IRES), an intron; an origin of replication, a polyadenylation signal (polyA), a promoter, a transcription termination sequence, and an upstream regulatory domain, which contribute to the replication, transcription, post-transcriptional processing of a nucleic acid sequence. Those of ordinary skill in the art are capable of selecting and using these and other regulatory elements in an expression construct with no more than routine experimentation.

Expression constructs operable to express a desired protein include, for example, in operable linkage: a promoter, a DNA sequence encoding a desired protein and a transcription termination site.

The term "operably linked" as used herein refers to a nucleic acid in functional relationship with a second nucleic acid.

A regulatory element included in an expression construct is a promoter in particular aspects.

The term "promoter" is well-known in the art and refers to one or more DNA sequences operably linked to a nucleic acid sequence to be transcribed and which bind an RNA polymerase and allow for initiation of transcription. A promoter is typically positioned upstream (5') of a nucleic acid encoding a peptide or protein to be expressed.

An mRNA polyadenylation (pA) sequence may be included such as, but not limited to SV40-pA, beta-globin-pA and SCF-pA.

An expression construct may include sequences necessary for amplification in bacterial cells, such as a selection marker (e.g. kanamycin or ampicillin resistance gene) and a replicon.

An internal ribosome entry site (IRES) is an optionally included nucleic acid sequence that permits translation initiation at an internal site in an mRNA. IRES are well-known in the art, for example as described in Pelletier, J. et al., Nature, 334:320-325, 1988; Vagner, S. et al., EMBO Rep., 2:893-898, 2001; and Hellen, C. U. et al, Genes Dev. 15:1593-1612, 2001.

The term "transcription termination site" refers to a DNA sequence operable to terminate transcription by an RNA polymerase. A transcription termination site is generally positioned downstream (3') of a nucleic acid encoding a peptide or protein to be expressed.

A leader sequence is optionally included in an expression construct.

An expression construct can be cloned into an expression vector for transformation into prokaryotic or eukaryotic cells and expression of the encoded peptides and/or protein(s). As used herein, "expression vectors" are defined as polynucleotides which, when introduced into an appropriate host cell or in a cell-free expression system, can be transcribed and translated, producing the encoded polypeptide(s).

Expression vectors are known in the art and include plasmids, cosmids, viruses and bacteriophages, for example. Expression vectors can be, without limitation, prokaryotic vectors, insect vectors, or eukaryotic vectors.

For example, an expression construct including, in operable linkage: a promoter, a DNA sequence encoding a desired protein and a transcription termination site, is included in a plasmid, cosmid, BAC, YAC, virus or bacteriophage expression vector. Particular viral vectors illustratively include those derived from adenovirus, adeno-associated virus and lentivirus.

Particular vectors are known in the art and one of skill in the art will recognize an appropriate vector for a specific purpose.

Host cells are provided according to aspects of the present invention which include a recombinant expression construct, wherein the recombinant expression construct includes a nucleic acid encoding an immunogenic composition, wherein the immunogenic composition includes an immunogenic tumor-associated self-antigen, and wherein the nucleic acid encoding the immunogenic composition is operably linked to a heterologous regulatory nucleic acid sequence.

Host cells are provided according to aspects of the present invention which include a recombinant expression construct, wherein the recombinant expression construct includes a nucleic acid encoding an immunogenic composition, wherein the immunogenic composition includes HER2, and wherein the nucleic acid encoding the immunogenic composition is operably linked to a heterologous regulatory nucleic acid sequence.

Host cells are provided according to aspects of the present invention which include a recombinant expression construct, wherein the recombinant expression construct includes a nucleic acid encoding an immunogenic composition, wherein the immunogenic composition includes human HER2, and wherein the nucleic acid encoding the immunogenic composition is operably linked to a heterologous regulatory nucleic acid sequence.

Host cells are provided according to aspects of the present invention which include a recombinant expression construct, wherein the recombinant expression construct includes a nucleic acid encoding an immunogenic composition, wherein the immunogenic composition includes the amino acid sequence of SEQ ID NO:2, or a variant thereof, and wherein the nucleic acid encoding the immunogenic composition is operably linked to a heterologous regulatory nucleic acid sequence.

Host cells are provided according to aspects of the present invention which include a recombinant expression construct, wherein the recombinant expression construct includes SEQ ID NO:25, or a variant thereof which encodes the amino acid sequence of SEQ ID NO:2, operably linked to a heterologous regulatory nucleic acid sequence.

Host cells are provided according to aspects of the present invention which include a recombinant expression construct, wherein the recombinant expression construct encodes the amino acid sequence of SEQ ID NO:17, or a variant thereof, operably linked to a heterologous regulatory nucleic acid sequence.

Host cells are provided according to aspects of the present invention which include a recombinant expression construct, wherein the recombinant expression construct includes SEQ ID NO:27, or a variant thereof which encodes the amino acid sequence of SEQ ID NO:17, operably linked to a heterologous regulatory nucleic acid sequence.

Any suitable expression vector/host cell system can be used for expression according to aspects of the present invention.

Expression of a desired protein using a recombinant expression vector is accomplished according to aspects of the present invention by introduction of the expression vector into a eukaryotic or prokaryotic host cell expression system such as an insect cell, mammalian cell, yeast cell, fungus, bird egg, bacterial cell or any other single or multicellular organism recognized in the art.

Host cells containing the recombinant expression vector are maintained under conditions wherein the desired protein is produced. Host cells may be cultured and maintained using known cell culture techniques such as described in Celis, Julio, ed., 1994, Cell Biology Laboratory Handbook, Academic Press, N.Y. Various culturing conditions for these cells, including media formulations with regard to specific nutrients, oxygen, tension, carbon dioxide and reduced serum levels, can be selected and optimized by one of skill in the art.

For expression in a host cell, any of the well-known procedures for introducing recombinant nucleic acids into host cells may be used, such as calcium phosphate transfection, polybrene, protoplast fusion, electroporation, sonoporation, liposomes and microinjection, examples of which are described in Sambrook et al., Molecular Cloning: A Laboratory Manual, Cold Spring Harbor Laboratory Press, 2001; and Ausubel, F. et al., (Eds.), Current Protocols in Molecular Biology, 2014.

The host cell may be in vivo or in vitro.

According to particular aspects, "naked" nucleic acid, such as DNA or mRNA, is introduced into a host cell in vivo for expression in the host. Introduction of a nucleic acid encoding the desired protein to a cell in vivo can be accomplished by a variety of techniques, including, but not limited to, electroporation, sonoporation, liposome administration, injection and microinjection.

According to particular aspects, the nucleic acid encoding the protein is present in an expression vector and the expression vector is introduced into a host cell in vivo for expression in the host. Introduction of an expression vector including a nucleic acid encoding the desired protein to a cell in vivo can be accomplished by a variety of techniques, including, but not limited to, electroporation, sonoporation, liposome administration, injection, and microinjection. According to particular aspects, the expression vector is a virus, including, but not limited to an adenovirus, an adeno-associated virus, and a lentivirus.

According to particular aspects, the expression vector is a virus, cells are infected with the virus, and the infected cells are administered to the subject, whereby the protein is expressed in the cells in vivo. According to particular aspects, the expression vector is a virus, white blood cells are infected with the virus, and the infected white blood cells are administered to the subject, whereby the protein is expressed in the white blood cells in vivo. Optionally, the cells are derived from the subject, infected with the virus, and then administered to the subject, whereby the protein is expressed in the white blood cells in vivo.

Optionally, the expressed protein is isolated from the host cell, or where the protein is produced by other methods, such as by chemical synthesis, the protein is isolated from reagents, such as chemical synthesis reagents. The term "isolated" in this context refers to removal of the protein from other components of a host cell, or from chemical synthetic reagents, such that the isolated protein includes at least 20% by weight of the protein, at least 25% by weight of the protein, at least 30% by weight of the protein, at least 35% by weight of the protein, at least 40% by weight of the protein, at least 45% by weight of the protein, at least 50% by weight of the protein, at least 55% by weight of the protein, at least 60% by weight of the protein, at least 65% by weight of the protein, at least 70% by weight of the protein, at least 75% by weight of the protein, at least 80% by weight of the protein, at least 85% by weight of the protein, at least 90% by weight of the protein, at least 91% by weight of the protein, at least 92% by weight of the protein, at least 93% by weight of the protein, at least 94% by weight of the protein, at least 95% by weight of the protein, at least 96% by weight of the protein, at least 97% by weight of the protein, at least 98% by weight of the protein, at least 99% by weight of the protein, or greater % by weight of the protein.

Methods of treatment or prevention of a HER2+ cancer in a subject are provided according to aspects of the present invention which include administering a therapeutically effective amount of an immunogenic composition. According to aspects of the present invention, an immunogenic composition is administered which includes an immunogenic tumor-associated self-antigen characterized by one or more of: 1) effectiveness to stimulate immune activity against a specified tumor-associated self-antigen in a subject, 2) effectiveness to overcome self-tolerance of the specified tumor-associated self-antigen, and 3) substantial similarity to the native three dimensional structure of the specified tumor-associated self-antigen.

Methods of treatment or prevention of a HER2+ cancer in a subject are provided according to aspects of the present invention which include administering a therapeutically effective amount of an immunogenic composition including a protein, wherein the protein has, or includes, the amino acid sequence of SEQ ID NO:2.

Optionally, the immunogenic composition is administered as a nucleic acid encoding a protein including the amino acid sequence of SEQ ID NO:2 operably linked to a heterologous regulatory nucleic acid sequence, such as in an expression construct, expression vector, or as "naked" DNA or mRNA to be expressed in vivo in the subject.

Methods of treatment or prevention of a HER2+ cancer in a subject are provided according to aspects of the present invention which include administering a therapeutically effective amount of an immunogenic composition including a protein, wherein the protein has, or includes, a variant of the amino acid sequence of SEQ ID NO:2.

Optionally, the immunogenic composition is administered as a nucleic acid encoding a protein including a variant of the amino acid sequence of SEQ ID NO:2 operably linked to a heterologous regulatory nucleic acid sequence, such as in an expression construct, expression vector, or as "naked" DNA or mRNA to be expressed in vivo in the subject.

Methods of treatment or prevention of a HER2+ cancer in a subject are provided according to aspects of the present invention which include administering a therapeutically effective amount of an immunogenic composition including a protein, wherein the protein has, or includes, the amino acid sequence of SEQ ID NO:17.

Optionally, the immunogenic composition is administered as a nucleic acid encoding a protein including the amino acid sequence of SEQ ID NO:17 operably linked to a heterologous regulatory nucleic acid sequence, such as in an expression construct, expression vector, or as "naked" DNA or mRNA to be expressed in vivo in the subject.

Methods of treatment or prevention of a HER2+ cancer in a subject are provided according to aspects of the present invention which include administering a therapeutically effective amount of an immunogenic composition including a protein, wherein the protein has, or includes, a variant of the amino acid sequence of SEQ ID NO:17.

Optionally, the immunogenic composition is administered as a nucleic acid encoding a protein including a variant of the amino acid sequence of SEQ ID NO:17 operably linked to a heterologous regulatory nucleic acid sequence, such as in an expression construct, expression vector, or as "naked" DNA or mRNA to be expressed in vivo in the subject.

Optionally, a method of treatment or prevention of a HER2+ cancer in a subject according to aspects of the present invention further includes administering an additional therapeutic agent or treatment to the subject.

HER2+ cancers include, but are not limited to breast, ovarian, non-small cell lung, and gastric cancers. The term "HER2+" is used interchangeably with "HER2-positive" and refers to cancers in which cancer cells have higher than normal levels of HER2, see, for example, Slamon D J, et al., 1989, 244:707-712, PMID: 2470152. Further, HER2 signaling is dysregulated in some cancers—thus differing from normal cells, see for example, Ménard S, et al., J. Cell Physiol., 2000, 281:150-162, PMID: 10623878.

The dosage of an inventive pharmaceutical composition administered to a subject will vary based on factors such as the route of administration; the age, health, and weight of the subject to whom the composition is to be administered; the nature and extent of the subject's symptoms, if any, and the effect desired. Usually a daily dosage of an immunogenic composition is in the range of about 0.001 to 100 milligrams per kilogram of a subject's body weight. A daily dose may be administered as two or more divided doses to obtain the desired effect. An inventive pharmaceutical composition may also be formulated for sustained release to obtain desired results.

A subject treated according to methods and using compositions of the present invention can be mammalian or non-mammalian. A mammalian subject can be any mammal including, but not limited to, a human; a non-human primate; a rodent such as a mouse, rat, or guinea pig: a domesticated pet such as a cat or dog; a horse, cow, pig, sheep, goat, or rabbit. A non-mammalian subject can be any non-mammal including, but not limited to, a bird such as a duck, goose, chicken, or turkey. Subjects can be either gender and can be any age. In aspects of methods including administration of an inventive composition to a subject, the subject is human.

As used herein, the terms "treatment" or "treating" are used to refer to administration of an immunogenic composition for obtaining beneficial or desired results including clinically beneficial or desired results which include, but are not limited to, one or more of the following: alleviating one or more symptoms resulting from the disease, diminishing the extent of the disease, stabilizing the disease (e.g., preventing or delaying the worsening of the disease), preventing or delaying the spread of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. The term "treatment" encompasses prophylactic treatment. As used herein, the term "prevent" refers to the reduction in the risk of acquiring or developing a given condition, or the reduction or inhibition of the recurrence or said condition in a subject.

Methods of generating an immunogenic composition are provided according to aspects of the present invention which include: identifying a reference sequence; identifying at least a first amino acid sequence homologous to the reference sequence, wherein the reference sequence and the first amino acid sequence homologous to the reference sequence are not identical; comparing the homologous amino acid sequence and the reference sequence to identify at least a first difference between the homologous amino acid sequence and the reference sequence at a first position in the reference sequence and a corresponding first position in the homologous amino acid sequence; assigning a BLOSUM62 score to the first difference between the homologous amino acid sequence and the reference sequence, wherein the score represents a probability of substitution of an amino acid at the first position of the reference sequence with the amino acid at the corresponding first position in the homologous sequence, wherein the score falls within a numerical probability range of −4 to +3, where −4 is a number which indicates an extremely non-conservative substitution of the amino acid at the first position of the reference sequence with the amino acid at the corresponding first position of the homologous sequence such that the occurrence of substitution of the extremely non-conservative substitution is relatively rare or unlikely, where +3 is a number which indicates an extremely conservative substitution of the amino acid at the first position of the reference sequence with the amino acid at the corresponding first position of the homologous sequence such that the occurrence of substitution of the extremely non-conservative substitution is relatively frequent or likely, where a BLOSUM score of 0 indicates neutrality such that the occurrence of substitution has an equal probability; and synthesizing a new amino acid sequence identical to the reference amino acid sequence with the proviso that that the new amino acid sequence has at least one substitution at the first position with an amino acid present at the corresponding first position in the homologous amino acid sequence where the score assigned to the first difference is in the range of 0 to 1 and indicates neutrality such that the occurrence of substitution has an equal probability, thereby generating an immunogenic composition. According to aspects, at least 2, at least 3, at least 4, at least 5, at least 6, at least 7, at least 8, at least 9, at least 10, at least 11, at least 12, at least 13, at least 14, or at least 15, amino acid sequences homologous to the reference sequence are identified and compared with the reference amino acid sequence. According to aspects, at least 2, at least 3, at least 4, at least 5, at least 6, at least 7, at least 8, at least 9, at least 10, at least 11, at least 12, at least 13, at least 14, at least 15, or more, differences between the homologous amino acid sequence and the reference sequence at corresponding $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$ or more, positions in the reference sequence and a corresponding position in the homologous amino acid sequence are identified and assigned a BLOSUM score. According to aspects, at least 2, at least 3, at least 4, at least 5, at least 6, at least 7, at least 8, at least 9, at least 10, at least 11, at least 12, at least 13, at least 14, or at least 15, substitutions are made in the reference amino acid sequence at $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$ or more, positions in the reference sequence with an amino acid present at the corresponding $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$ or more, positions in the homologous amino acid sequence where the BLOSUM score assigned to the differences identified at the $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$ or more, positions is in the range of 0 to 1.

Methods of generating an immunogenic composition according to aspects of the present invention include: identifying a reference sequence; identifying at least a first amino acid sequence homologous to the reference sequence, wherein the reference sequence and the first amino acid sequence homologous to the reference sequence are not identical; comparing the homologous amino acid sequence and the reference sequence to identify at least a first difference between the homologous amino acid sequence and the reference sequence at a first position in the reference sequence and a corresponding first position in the homologous amino acid sequence; assigning a score to the first difference between the homologous amino acid sequence and the reference sequence, wherein the score represents a probability of substitution of an amino acid at the first position of the reference sequence with the amino acid at the corresponding first position in the homologous sequence, wherein the score falls within a numerical probability range of x to y, where x is a number which indicates an extremely non-conservative substitution of the amino acid at the first position of the reference sequence with the amino acid at the corresponding first position of the homologous sequence such that the occurrence of substitution of the extremely non-conservative substitution is relatively rare or unlikely, where y is a number which indicates an extremely conservative substitution of the amino acid at the first position of the reference sequence with the amino acid at the corresponding first position of the homologous sequence such that the occurrence of substitution of the extremely non-conservative substitution is relatively frequent or likely, where a number intermediate between x and y indicates neutrality such that the occurrence of substitution has an equal probability; and synthesizing a new amino acid sequence identical to the reference amino acid sequence with the proviso that that the new amino acid sequence has at least one substitution at the first position with an amino acid present at the corresponding first position in the homologous amino acid sequence where the score assigned to the first difference is intermediate between x and y indicates neutrality such that the occurrence of substitution has an equal probability, thereby generating an immunogenic composition. According to aspects, at least 2, at least 3, at least 4, at least 5, at least 6, at least 7, at least 8, at least 9, at least 10, at least 11, at least 12, at least 13, at least 14, or at least 15, amino acid sequences homologous to the reference sequence are identified and compared with the reference amino acid sequence. According to aspects, at least 2, at least 3, at least 4, at least 5, at least 6, at least 7, at least 8, at least 9, at least 10, at least 11, at least 12, at least 13, at least 14, at least 15, or more, differences between the homologous amino acid sequence and the reference sequence at corresponding $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$ or more, positions in the reference sequence and a corresponding position in the homologous amino acid sequence are identified and assigned a score. According to aspects, at least 2, at least 3, at least 4, at least 5, at least 6, at least 7, at least 8, at least 9, at least 10, at least 11, at least 12, at least 13, at least 14, or at least 15, substitutions are made in the reference amino acid sequence at $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$ or more, positions in the reference sequence with an amino acid present at the corresponding $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$ or more, positions in the homologous amino acid sequence where the score assigned to the differences identified at the $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$ or more, positions is intermediate between x and y indicating that the occurrence of substitution has an equal probability.

Methods of generating an immunogenic composition according to aspects of the present invention, also referred to herein as "evolution selection" were used to design minimally modified antigens effective to stimulate immune activity against a tumor-associated self-antigen, effective to overcome self-tolerance of the tumor-associated self-antigen. Methods of generating an immunogenic composition described herein are grounded on principles of protein evolution and based on the premise that amino acids that tend to be frequently substituted with particular residues across the proteins of closely related animal species, such as, but not limited to, HER proteins, are not likely to alter the structure and function of the proteins. Amino acids at these commonly substituted positions are therefore good candidates for substitutions aimed at increasing the "foreignness" of the protein without altering the target epitopes. The degrees of conservatism at the commonly substituted positions can be analyzed by BLOSUM62 scoring or another suitable bioinformatic sequence alignment procedure. The substitutions are tested for immunogenicity and therapeutic effect in various in vitro and in vivo assays.

Methods of generating an immunogenic composition according to aspects of the present invention produce an immunogenic protein effective to stimulate immune activity against a tumor-associated self-antigen in a subject, administration of which is effective to overcome self-tolerance of the tumor-associated self-antigen, and which is characterized by substantial similarity to the native three dimensional structure of the tumor-associated self-antigen.

Methods of generating an immunogenic composition according to aspects of the present invention produce an immunogenic protein characterized by one or more of: 1) effectiveness to stimulate immune activity against a specified tumor-associated self-antigen in a subject, 2) effectiveness to overcome self-tolerance of the specified tumor-associated self-antigen, and 3) substantial similarity to the native three dimensional structure of the specified tumor-associated self-antigen.

Methods of generating an immunogenic composition according to aspects of the present invention produce an immunogenic protein characterized by one or more of: 1) effectiveness to stimulate immune activity against HER2 in a subject, 2) effectiveness to overcome self-tolerance of HER2, and 3) substantial similarity to the native three dimensional structure of HER2.

Methods of generating an immunogenic composition according to aspects of the present invention produce an immunogenic protein characterized by one or more of: 1) effectiveness to stimulate immune activity against human HER2 in a subject, 2) effectiveness to overcome self-tolerance of human HER2, and 3) substantial similarity to the native three dimensional structure of human HER2.

Methods of generating an immunogenic composition according to aspects of the present invention produce an immunogenic protein characterized by one or more of: 1) effectiveness to stimulate immune activity against human HER2 of SEQ ID NO:1 in a subject, 2) effectiveness to overcome self-tolerance of human HER2 of SEQ ID NO:1, and 3) substantial similarity to the native three dimensional structure of human HER2 of SEQ ID NO:1.

Methods of generating an immunogenic composition according to aspects of the present invention produce an immunogenic protein characterized by one or more of: 1) effectiveness to stimulate immune activity against a variant of human HER2 of SEQ ID NO:1 in a subject, 2) effectiveness to overcome self-tolerance of a variant of the human HER2 of SEQ ID NO:1, and 3) substantial similarity to the native three dimensional structure of a variant of the human HER2 of SEQ ID NO:1.

Methods of generating an immunogenic composition according to aspects of the present invention produce an immunogenic protein characterized by one or more of: 1) effectiveness to stimulate immune activity against human HER2 of SEQ ID NO:16 in a subject, 2) effectiveness to overcome self-tolerance of the human HER2 of SEQ ID NO:16, and 3) substantial similarity to the native three dimensional structure of the human HER2 of SEQ ID NO:16.

Methods of generating an immunogenic composition according to aspects of the present invention produce an immunogenic protein characterized by one or more of: 1) effectiveness to stimulate immune activity against a variant of human HER2 of SEQ ID NO:16 in a subject, 2) effectiveness to overcome self-tolerance of a variant of the human HER2 of SEQ ID NO:16, and 3) substantial similarity to the native three dimensional structure of a variant of the human HER2 of SEQ ID NO:16.

Methods of generating an immunogenic composition according to aspects of the present invention are useful to generate immunogenic compositions against any tumor-associated self-antigen where self-tolerance of the tumor-associated self-antigen must be overcome in order to treat and/or prevent cancer, including, but not limited to, HER2, HER1 (EGFR), and HER3.

Accordingly, a method according to aspects of the present invention for generating a minimally modified immunogenic polypeptide for breaking tolerance to a host's target HER family antigen begins with the step of comparing the amino acid sequence of the target HER family receptor to those of homologous HER family receptors of several species closely related to the host. One or more residues found frequently to be substituted by common residues in these related species are then substituted with the common residues into the host's target HER family receptor, to create at least one candidate antigen. Finally, it is determined whether the candidate antigen is capable of breaking tolerance to the target HER family antigen.

In exemplary embodiments of the invention, the target is human HER2; the homologous receptors are non-human primateHER2; and BLOSUM62 scoring is the means of evaluating the sites of substitution and the conservativeness of possible substitutions. The invention also includes designer antigens designed by the process of evolution selection, and vaccines including those antigens.

In vivo testing of one of the resulting designer HER2 vaccines (i.e. immunogenic compositions according to aspects of the present invention), which contains 5 substitutions in the extracellular domain (ECD), showed it induces elevated humoral and cellular immunity to HER2 and reduces tumor growth. The vaccine antigen h(es)E2ectm includes SEQ ID NO:2 in the sequence list found below. For reference, the wild type antigen includes the SEQ ID NO:1.

It has recently been determined that the delta 16 splice variant of HER2, which lacks exon 16, spontaneously dimerizes to cause constitutive stimulation and proliferation of epithelial cells (Wada R, et al., Mol. Med. Rep., 2016, 14(6):5104-5110. doi: 10.3892/mmr.2016.5892). For human HER2, the sequence of this splice variant is given as SEQ ID NO:16. The invention includes evolution selected variants of the delta 16 splice variant, such as human vaccine antigen Human (es)E2ectm-delta 16, SEQ ID NO:17.

The invention is not limited to human HER family vaccines. In fact, commercialization may be accomplished most rapidly for vaccines against cancers of domestic animals that are prone to breast cancer, such as cats and dogs. There are too few feline or canine ERBB2 sequences available for an analogous approach to designing (es) ERBB2 vaccines for those species, so the positions and patterns of aa substitutions from the human/primate alignment analysis were superimposed, as indicated in the headings for the feline vaccine antigen sequence (SEQ ID NO:19) (Feline (es)E2ectm), and the canine vaccine antigen sequence (SEQ ID NO:22) (Dog (es)E2ectm). The delta 16 variants of these antigens are given as SEQ ID NO:20 and SEQ ID NO:23, respectively. For reference, the wild type sequences are SEQ ID NO:18 and SEQ ID NO:21.

Exemplary cDNA sequences are also provided in the sequence list, for above-mentioned vaccine antigens, and for their wild type counterparts (SEQ ID NOs: 24-33). It will be understood that any DNA sequence that encodes the disclosed peptides of the vaccine antigens is encompassed by the present inventions.

Also provided in the sequence list, as SEQ ID NOs:34-39, are PCR primers for construction of human ERBB2-delta16, feline ERBB2-delta16 and canine ERBB2-delta16 and derivatives thereof. They can be used, for example, with New England Biolab's Q5 Site-Directed Mutagenesis procedure (NEB E0554) when cloned into circular expression vector (e.g., pVAX1).

The designer antigens of the present invention can be deployed in any conceivable vaccine composition. In exemplary embodiments, the antigens are encoded in naked DNA plasmids for expression in vivo. The antigens can alternatively be incorporated into an unlimited range of expression constructs, and delivered in an unlimited range of vectors. The antigens should also be effective as recombinant proteins, if introduced by an effective delivery system. The vaccines are contemplated at present as preventative therapeutic vaccines, and are also useful in a therapeutic setting, against existing tumors.

Embodiments of inventive compositions and methods are illustrated in the following examples. These examples are provided for illustrative purposes and are not considered limitations on the scope of inventive compositions and methods.

Examples

Materials and Methods

Mice

Wild type C57BL/6 and BALB/c mice are purchased from Charles River Laboratory (Frederick, MD, US). Heterozygous C57BL/6 HER-2 Tg mice (B6 HER-2 Tg), which express the full-length, wild type human HER-2 under the whey acidic protein (WAP) promoter were generated as described in detail in Piechocki et al., J. Immunol. 2003, 171(11):5787-94 and maintained by mating with wild type B6 mice as described in detail in Piechocki et al., J. Immunol. 2003, 171(11):5787-94.

BALB/c HER-2 Tg (BALB HER-2 Tg) mice were generated by back-crossing B6 HER-2 Tg mice with wild type BALB/c mice (described in detail in Yong C S, et al., 2015, PLoS One. 10: e0136817. doi: 10.1371/journal-.pone.0136817) and are maintained by mating with BALB/c mice. Transgene positive mice were identified by PCR as described in detail in Radkevich-Brown O, et al., 2009, Cancer Res. 69: 212-8. doi: 10.1158/0008-5472.CAN-083092. B6 HER2 Tg mice have been deposited at Jackson lab repository (B6.Cg-Tg(Wap-ERBB2)229Wzw/J).

Construction and Validation of DNA Constructs pVAX1 (Thermo Fisher Scientific) was used for constructing ion of each of the following genetic vaccines. pE2TM contains codons 1-687 of human variant 1 ErbB2 cDNA (NM-004448) and the transgene was inserted between HindIII and XbaI within the multiple cloning site(12). pNeu contains codons 1-692 of the rat neu oncogene cDNA (X03362). pE2neu contains codons 1-390 of NM-004448, a GAATTCGCT bridge, then codons 395-692 of X03362 (12, 13, 21). prmE2TM contains codons 1-687 of Rhesus (*Macaca mulata*) variant. X1 ErbB2 (XM_001090430)(GenScript) and was inserted between the NheI and XbaI sites in pVAX1. ph(es)E2TM is pE2TM with 5 codon substitutions (M198V, Q398R, F425L, H473R and A622T) and was inserted utilizing the Nhei and XbaI sites. Candidate DNA constructs were validated by transient transfection into NIH 3T3 cells using LipofectAMINE (Invitrogen, Carlsbad CA), following the manufacturer's instructions. Monoclonal antibodies TA-1 (Ab5; Calbiochem, San Diego, CA), N12, N29 (see Bacus S S, et al., 1992, Cancer Res. 52: 2580-9; and Stancovski I, et al., 1991, Proc Natl Acad Sci USA, 88: 8691-5; both hybridomas provided by Dr. Yosef Yarden, Weissman Inst) and trastuzumab (see Cho H S, et al., 2003, Nature, 421: 756-60. doi: 10.1038/nature01392) (Genentech) are used to characterize HER-2 epitopes. mAb 7.16.4 (Ab4, Calbiochem, San Diego, CA) was used to detect rat Neu epitope (Heeney J L, et al., Science, 2006, 313:462-6). PE-goat-anti-mouse IgG or PE-mouse-anti-human IgG were the secondary antibodies. Samples are analyzed on a BD FACScanto II and with FlowJo software (TreeStar, Ashland OR).

Cell Lines and Reagents.

All tissue culture reagents were purchased from Invitrogen. Cell lines were cultured as described in detail in Jacob J B, et al., 2010, Cancer Res., 70: 119-28. doi: 10.1158/0008-5472.CAN-09-2554 and antigen-presenting cells (APC) 3T3/KB and 3T3/NKB generated as described in detail in Wei W Z, et al., 2005, Cancer Res. 65: 8471-8. doi: 10.1158/0008-5472.CAN-05-0934. Briefly, BALB/c NIH 3T3 fibroblasts were transfected with $K^d$ and B7.1 (CD80) to generate 3T3/KB, or with the addition of HER2 for 3T3/EKB. 3T3/NKB similarly generated to express Neu was used for measuring anti-Neu Ab levels in the immune serum. The expression of the transgenes is validated by flow cytometry using mAb to Kd (SF1-1.1, Biolegend), B7.1 (CD80,), HER2 (TA-1/Ab5, Calbiochem) and Neu (Ab4). C57BL/6 lung epithelial cell line TC-1 expressing Kb and B7.1 was a gift from Dr. T. C. Wu (The Johns Hopkins University, Baltimore, MD). TC-1/E2 cells were transfected with wt HER-2 as previously described (Radkevich-Brown O. et al., (2010). Cancer Immunol Immunother. 59: 409-17. doi: 10.1007/s00262-009-0760-. TC-1 and TC-1/E2 cells are validated by tumor growth in C57BL/6 mice and by their expression of Kb as detected by mAb Af6-88.5.5.3 (eBioscience). Stable clones were maintained in G418 and puromycin medium (3T3/KB) or zeocin (3T3/NKB). SKOV3 cells were purchased from the American Type Culture Collection. D2F2 is a mouse mammary tumor that arose in a BALB/c hyperplastic alveolar nodule line, D2 described in Piechocki M P, et al., 2001, J. Immunol., 167: 3367-74; Medina D, et al., 1970, J. Natl. Cancer Inst., 45: 353-63; and Wei W Z, et al., 1986, Cancer Res. 46: 2680-5. D2F2 cells were co-transfected with pRSV/neo and pCMV/Neu, which encodes wild-type rat Neu to establish D2F2/Neu, as described in Jacob J, et al., 2006, Cell Immunol., 240: 96-106. doi: 10.1016/j.cellimm.2006.07.002. D2F2/E2 cells were generated by co-transfection with a HinDIII WAP-HER-2 expression cassette (6.9-kb) and linearized pRSV/neo as detailed in Piechocki M P, et al., 2001, J. Immunol., 167: 3367-74. D2F2/E2t cells were selected from D2F2/E2 cells by serial passage in BALB/c mice. D2F2 cells and derivatives are validated by tumor growth in BALB/c mice and by their expression of Kd as detected by mAb SF1-1.1. Expression of HER2 in D2F2/E2 and D2F2/E2t is verified by mAb Ab5, using flow cytometry. SK-BR-3 and SKOV3 cells were purchased from the American Type Culture Collection. Authentication of SKBR-3 and SKOV3 cells by short tandem repeat (STR) profiling was carried out with Promega's Cell ID System. Transfected cells were maintained in medium with 0.8 mg/mL G418 (Geneticin; Invitrogen) puromycin or zeocin.

Derivation of D2F2/E2t

D2F2/E2 cells ($2 \times 10^5$ cells) were inoculated into the mammary fat pads of female BALB/c mice and the outgrowth was serially transplanted into naïve female BALB/c mammary fat pads for a total of 7 times. HER2 expression was evaluated after each passage by flow cytometry. Tumor cells were dissociated after the 7th transplantation and cloned. The cell D2F2/E2 clone cells maintaining with the highest HER2 expression were selected and designated D2F2/E2t. D2F2/E2t is maintained in medium containing 0.6 mg/ml G418.

Validation of Cell Lines

Validation of cell lines by short tandem repeat (STR) profiling was carried out with Promega's Cell ID System as described by the supplier. BALB/c origin of D2F2 and derivatives was validated by tumor growth in BALB/c mice.

DNA Electrovaccination pcDNA/Neu encoding the extracellular and transmembrane domains of rat Neu was described in detail in Rovero S, et al., J. Immunol., 2000, 165:5133-42. pEF-Bos/granulocyte macrophage colony-stimulating factor (pGM-CSF) encoding murine GM-CSF was provided by Dr. N. Nishisaka at Osaka University, Osaka, Japan. Mice were electrovaccinated as described in detail in Wei W Z, et al., Int. J. Cancer, 1999, 81:748-54. Mice are anesthetized and 50 micrograms of test DNA construct admixed with 20 micrograms pGM-CSF in 50 µL PBS is injected intramuscularly (i.m.) in the quadriceps. Immediately following injection, square wave electroporation is applied over the injection site as described in Wei W Z, et al., Int. J. Cancer, 1999, 81:748-54 using a BTX830 (BTX Harvard Apparatus) or NEPA21 super electroporator (Nepa Gene) as described in detail in Roque-Afonso A M, et al., Antivir. Ther., 2007, 12:1255-63. The pulses at 100V with 20 msec duration are delivered 8 times in two opposite orientations. Mice were electrovaccinated one to three times at 2 wk intervals as described in the Results.

Regulatory T Cell Depletion

In B6 HER-2 Tg mice, regulatory T cells (Treg) were depleted 10 days prior to vaccination by injecting i.p. 0.25 mg anti-CD25 mAb PC61.

Immune Monitoring

Sera, peripheral blood lymphocytes (PBL) and(or) splenocytes (SC) were collected 2 wks following the last electrovaccination. Anti-HER-2 antibodies were measured by binding to HER-2 overexpressing SKOV3 cells using flow cytometry and antibody concentrations were calculated by regression analysis using mAb TA-1 as the standard as described in detail in Piechocki M P, et al, 2002, J. Immunol. Methods, 259: 33-42. Normal mouse serum or isotype matched mAb was the control. Anti-Neu antibodies were measured with 3T3/NKB cells and the standard curve is generated using mAb 7.16.4 (Ab4). Differences in antibody concentration are analyzed by the Student's t test.

ELISpot reagents were purchased from BD Biosciences. HER-2 reactive T cells were enumerated by IFN-γ ELISpot assay as described in detail in Jacob J B, et al., Cancer Res., 2010, 70:119-28; and Radkevich-Brown O, et al., Cancer Immunol. Immunother., 2010, 59:409-17. Peripheral blood (PBL) or spleen cells (SC) were incubated for 48 hours with the antigen presenting cells (APC) 3T3/EKB or TC-1/E2 (3T3/KB and TC-1 were negative controls) at an APC: lymphocyte ratio of 1:10 or recombinant HER2 or Neu protein (ecd-Fc fusion; SinoBiological). The results were expressed as number of cytokine-producing cells per $10^6$ SC. Data are analyzed using Student's t-test.

BLOSUM Scores

To quantify the biochemical alteration from amino acid substitutions in cancer vaccines, the Blocks Substitutions Matrix (BLOSUM) score, see Henikoff S, et al., 1992, Proc Natl Acad Sci USA., 89: 10915-9; and Pertsemlidis A, et al., 2001, Genome Biol., 2: REVIEWS2002, was utilized.

Blocks Substitutions Matrix (BLOSUM) scores (described in detail in Styczynski M P, et al., 2008, Nat. Biotechnol., 26: 274-5. doi: 10.1038/nbt0308-274) are log of odds calculated from the frequency of amino acid substitutions in closely related protein sequences. BLOSUM62 was established by comparing protein blocks containing >62% sequence identity, see Styczynski M P, et al., 2008, Nat. Biotechnol., 26: 274-5. doi: 10.1038/nbt0308-274.

Each of the 20 amino acids is assigned a log odds score of +4 to +11. Higher values indicate the invariant nature of those residues. For the 190 possible amino acid substitutions, each is assigned a BLOSUM score of +3 to −4, with 0 indicating a substitution with a "neutral" probability", i.e., equal probability of the alternative or original amino acid residues occurring.

Positive BLOSUM scores indicate conservative substitution with little impact on the protein. Very negative scores such as −4 indicate extremely rare substitution, which have 10,000 fold greater chance than the score of 0 for protein alterations.

Peptide Binding Profiling

Peptide binding analysis was performed with a microarray that displays a library of 168 HER2 ECD 15-mer peptides with 11-mer overlap (JPT Peptide Technologies, Germany). The peptides were covalently immobilized on glass slides (PepStar Peptide Microarrays, JPT). Immune serum samples diluted 1:200 were incubated on the array for 1 hr at 30° C. Bound Ab was visualized with a fluorescently labeled anti-mouse IgG.

After washing and drying, the slides were scanned at 635 nm to obtain fluorescence intensity profiles. The images were quantified to generate a mean pixel value for each peptide. A color-coded heat map was computed to show relative fluorescence intensities.

Inhibition of Tumor Cell Proliferation

Inhibition of tumor cell proliferation was measured by incubating human breast cancer cell line SK-BR-3 with HER2 immune serum in flat bottom 96 well plates. Serum from mice receiving blank pVax was the negative control. Gefitinib was used as a positive control. Cell survival was measured by Alamar Blue assay after 48 hours of incubation. Statistical significance was determined by Student's t test.

Inhibition of Tumor Growth In Vivo

BALB HER2Tg mice were electrovaccinated twice with pE2Neu or ph(es)E2TM, at 2 week intervals. At 2 weeks after the second vaccination, D2F2/E2t cells were implanted into the #4 mammary fat pad and tumor growth was monitored by palpation twice per week. The tumor size was measured with a caliper and calculated by $XY^2/2$ where X represents the longer axis and Y is the short axis.

Results

Hybrid HER2 Vaccine Constructs

The amino acid BLOSUM scores were evaluated in three existing HER2 vaccines FIG. 1A/B): pE2TM encoding native HER2 ECD and TM domains and a 12 AA fragment of the ICD; and the hybrid constructs pE2Neu and pNeuE2, each containing distinct AA substitutions. FIG. 1B shows BLOSUM scores for the 687 residues in pE2TM (top row), ranging from +4 to +11. Relative to pE2TM, pE2Neu contains 51 substitutions in ECD subdomains III/IV and 3 extra residues (AEF) in ECD subdomain III, following codon #389, due to DNA cloning methodology. Thirty-two of the 51 substitutions were conservative, with BLOSUM scores=0. The other 19 scored −1 to −4. The reverse construct, pNeuE2, harbors 54 Neu-derived AA substitutions in subdomains I/II with 25 non-conservative changes scoring at −1 to −4.

Potency of these vaccines were compared in BALB/c (BALB) HER2 Tg mice (Styczynski M P, et al., 2008, Nat. Biotechnol., 26: 274-5. doi: 10.1038/nbt0308-274) after 3× electrovaccination at 2 wk intervals as described herein and antibody levels were measured 2 weeks following each vaccination. Vaccination controls were pVax, pNeu encoding rat Neu, and admixed pE2TM and pNeu. FIG. 1C shows HER2 binding Ab (shaded diamonds) induced by DNA electrovaccination. Compared to pE2TM, pE2Neu and admixed pE2TM+pNeu induced 2-3 fold elevation of IgG (59±15 or 43±9 vs 20±13 μg/ml), implicating heterologous Neu epitopes in promoting HER2 self-reactivity (FIG. 1C). The reverse hybrid, pNeuE2, did not enhance HER2 Ab even though anti-Neu Ab level was high (46±18 μg/ml), see Jacob J B, et al., 2010, Cancer Res., 70: 119-28. doi: 10.1158/0008-5472.CAN-09-2554.

HER2 Vaccines with Single Amino Acid Substitutions

The increased antibody response in pE2Neu vaccinated HER2 Tg mice indicates pE2Neu as an effective vaccine. However, the structural, biochemical and immunological impact of substituting 51 of 687 residues and inserting 3 additional residues (AEF) could not be readily elucidated, making it difficult to extrapolate to other TAA. A rational HER2 vaccine design with minimal amino acid substitutions was sought. A panel of six pE2TM vaccines harboring single amino acid substitutions were generated and tested.

Figure 2B:
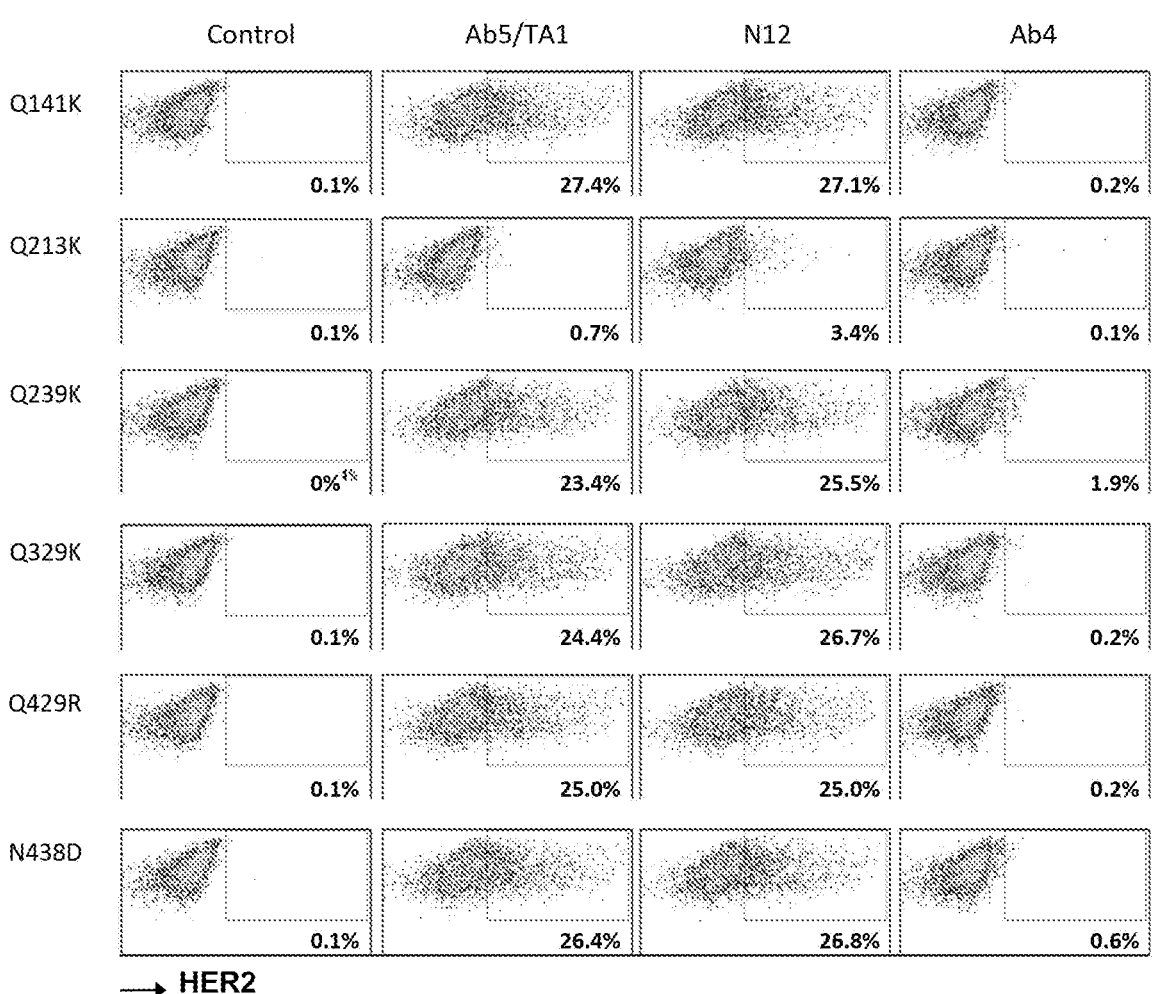
FIG. 2B is a series of graphs showing results of expression of recombinant point mutants; test vaccines were expressed in NIH 3T3 cells, then analyzed by flow cytometry using Ab4, Ab5, and N12 as detection antibodies.
Figure 2C:
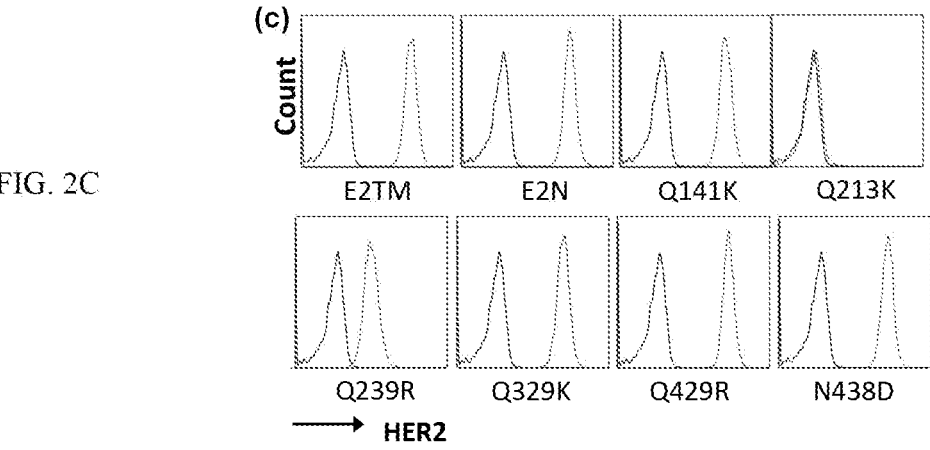
FIG. 2C shows immunogenicity of point mutants tested in BALB/c wild-type (wt) mice after one electrovaccination. Antibody response was monitored 2 weeks post-vaccination.

Glutamine (Q) or asparagine (N) located on the external surface of HER2 were replaced with AA carrying BLOSUM scores ≥1: Q141K, Q213K, Q239K, and Q329K, and Q429R and N438D (FIG. 2A). Stable expression of all mutants except Q231K was detected in transiently transfected 3T3 cells by anti-HER2 mAb TA-1 and N12, indicating preservation of the protein structure (FIG. 2B). Anti-neu mAb Ab4 was a negative control. To test immunogenicity in vivo, wt BALB/c mice were electrovaccinated once with the test constructs and HER2 binding Ab were measured two weeks following vaccination. All but Q213K test vaccines induced Ab (FIG. 2C).

Figure 2D:
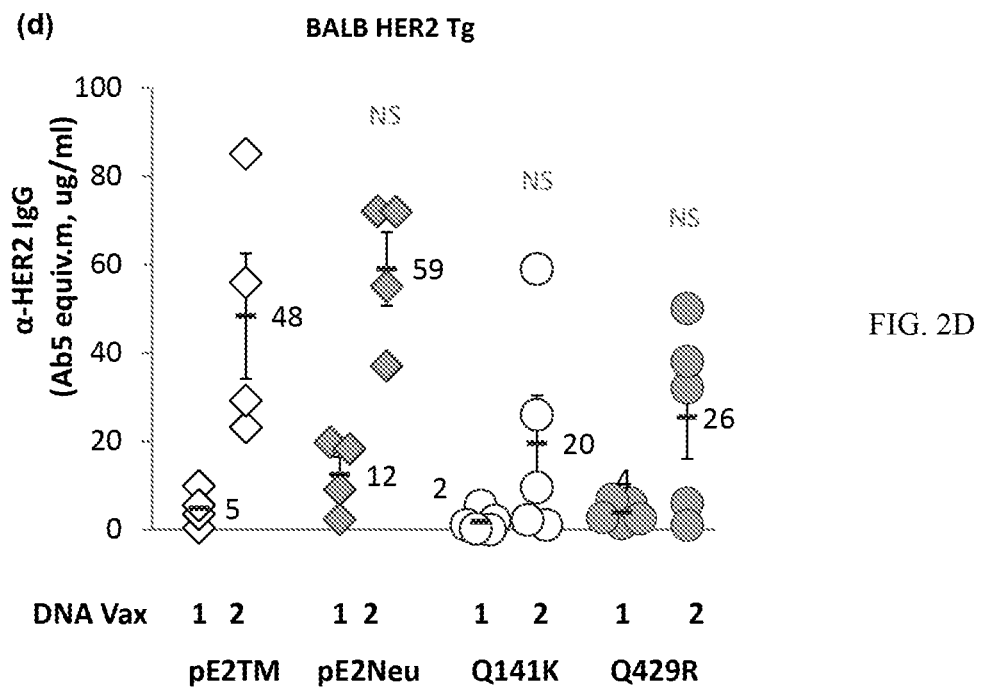
FIGS. 2D, 2E, 2F, and 2G generally show immunogenicity of selected point mutations in BALB HER-2 or B6 HER-2 transgenic (Tg) mice.
Figure 2E:
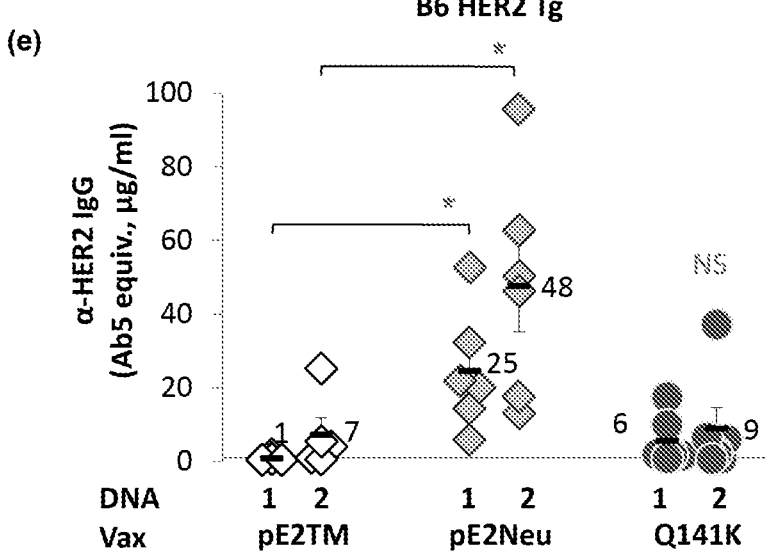
Figure 2F:
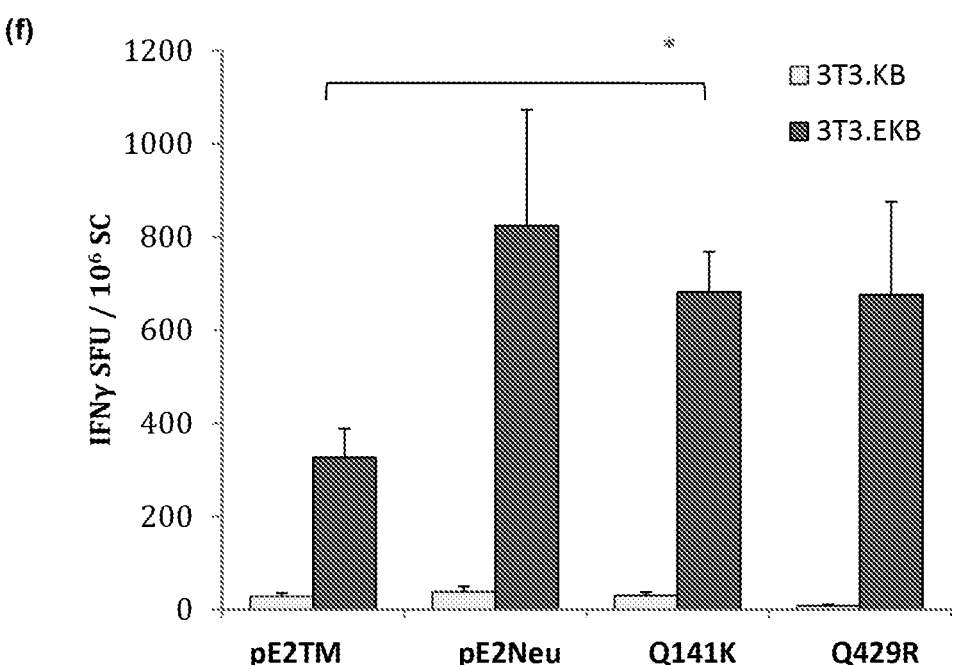
Figure 2G:
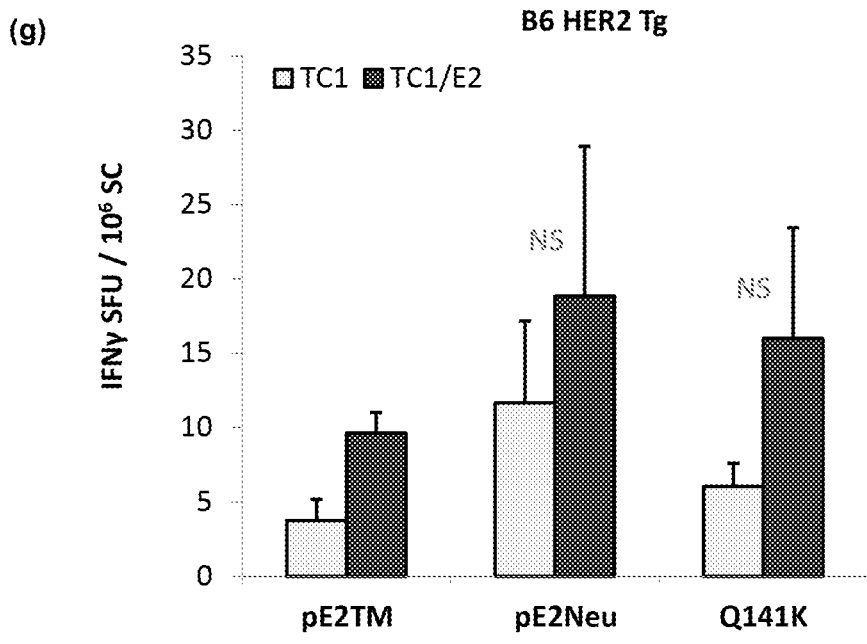

Preliminary testing of the 5 stable constructs shows Q141K and Q429R mutants producing more consistent IgG response in BALB HER2 Tg mice. The immunogenicity of these two mutant HER2 vaccines were tested in then comparisoned with pE2TM and pE2Neu vaccines. BALB HER2 Tg mice electrovaccinated 2× produced 48±12, 59±8, 20±11 and 26±10 μg/ml HER2 binding Ab after vaccination with pE2TM, pE2Neu, pE2TM-Q141K and pE2TM-Q429R mutant constructs, respectively, showing no advantage of single residue substitutions (FIG. 2D). 2× vaccination of Treg-depleted C57BL/6 (B6) HER2 Tg mice with pE2TM, pE2Neu or pE2TM-Q141K induced 7±5, 48±12 and 9±6 μg/ml HER2 binding Ab (FIG. 2E). Treg were depleted 10 days before vaccination because this mouse strain responds poorly in the presence of Treg (see Radkevich-Brown O. et al., (2009) Cancer Res. 69: 212-8. doi: 10.1158/0008-5472.CAN-08-3092). Q141K mutants induced elevated HER2-specific IFN-γ-producing T cells in BALB HER2 Tg mice when compared with pE2TM (FIG. 2F) but not in B6 HER2 Tg (FIG. 2G). Therefore, the overall trend that single residue substitution is less effective than pE2Neu is shown consistent in both BALB HER2 Tg and C57BL/6 HER2 Tg mice.

Evolution-Selected HER2 Vaccine ph(es)E2TM

To produce HER2 proteins that closely resemble human HER2 in order to preserve most antigenic epitopes, yet with sufficient alteration to overcome HER2 self-tolerance, common amino acid substitutions were sought in HER2 sequences from twelve primate species that share >95% sequence identity with human HER2 (Table 1).

TABLE 1

| Sequence | Sequence source | Start | End | Match | % Match | SEQ ID NO: |
|---|---|---|---|---|---|---|
| huE2ectm protein | NP_004439 | 1 | 687 | | | 1 |
| Bonobo-XP_008955 | XP_008955053 | 1 | 687 | 686 | 99 | 3 |
| BolivSqMonkey-XP | XP_010328997 | 38 | 701 | 644 | 93 | 4 |
| Chimp-XP_0033155 | XP_003315512 | 1 | 687 | 685 | 99 | 5 |
| GoldSnNo-Monkey-X | XP_010377602 | 1 | 687 | 673 | 97 | 6 |
| Gorilla-XP_00404 | XP_004041868 | 1 | 687 | 684 | 99 | 7 |
| GrnMonkey-XP_008 | XP_008011036 | 1 | 687 | 679 | 98 | 8 |
| OliveBaboon-XP_0 | XP_003912981 | 1 | 687 | 681 | 99 | 9 |
| RhesusErbB2-XP_0 | XM_001090430 | 1 | 687 | 677 | 98 | 10 |
| Rhesus-HER2prot2 | U.S. Pat. No. 7,282,365 | 1 | 687 | 677 | 98 | 11 |
| SumOrangutan-XP_ | XP_009250137 | 1 | 658 | 630 | 91 | 12 |
| WhChGibbon-XP_00 | XP_003278275 | 37 | 699 | 654 | 95 | 13 |
| WhTufEar-Marmoset | XP_002806904 | 1 | 687 | 660 | 96 | 14 |
| Macaca-XP_005584 | XP_005584091 | 98 | 784 | 677 | 98 | 15 |

Figure 8:
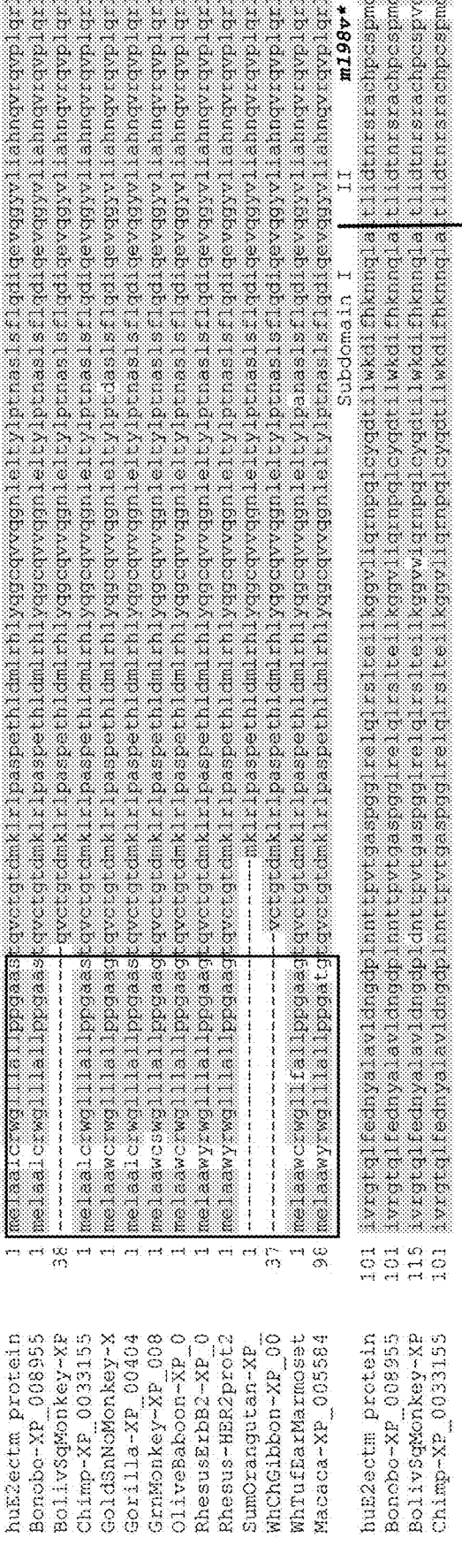
FIG. 8 shows sequence comparisons and alignment results for the 14 protein sequences listed in Table 1: huE2ectm protein (SEQ ID NO:1), Bonobo-XP_008955 (SEQ ID NO:3), BolivSqMonkey-XP (SEQ ID NO:4), Chimp-XP_0033155 (SEQ ID NO:5), GoldSnNoMonkey-X (SEQ ID NO:6), Gorilla-XP_00404 (SEQ ID NO:7), Grn-Monkey-XP_008 (SEQ ID NO:8), OliveBaboon-XP_0 (SEQ ID NO:9), RhesusErbB2-XP_0 (SEQ ID NO:10), Rhesus-HER2prot2 (SEQ ID NO:11), SumOrangutan-XP_ (SEQ ID NO:12), WhChGibbon-XP_00 (SEQ ID NO:13), WhTufEarMarmoset (SEQ ID NO:14), Macaca-XP_005584 (SEQ ID NO:15). For this alignment, global protein alignment against reference molecule was used, wherein the reference molecule as huE2ectm protein, Region 1 to 687. Fourteen sequences were aligned and the total length of aligned sequences with gaps was 688 amino acids. Parameters: Scoring matrix: BLOSUM 62. * indicates aa substitutions in hu vs. primate E2ectm [Blosum62 score] 198 3M→8V [1]; 398 7Q→6R [1]; 425 8F→6L [0]; 473 4H→10R [0]; and 622 2A→12T [0].
Figure 8:
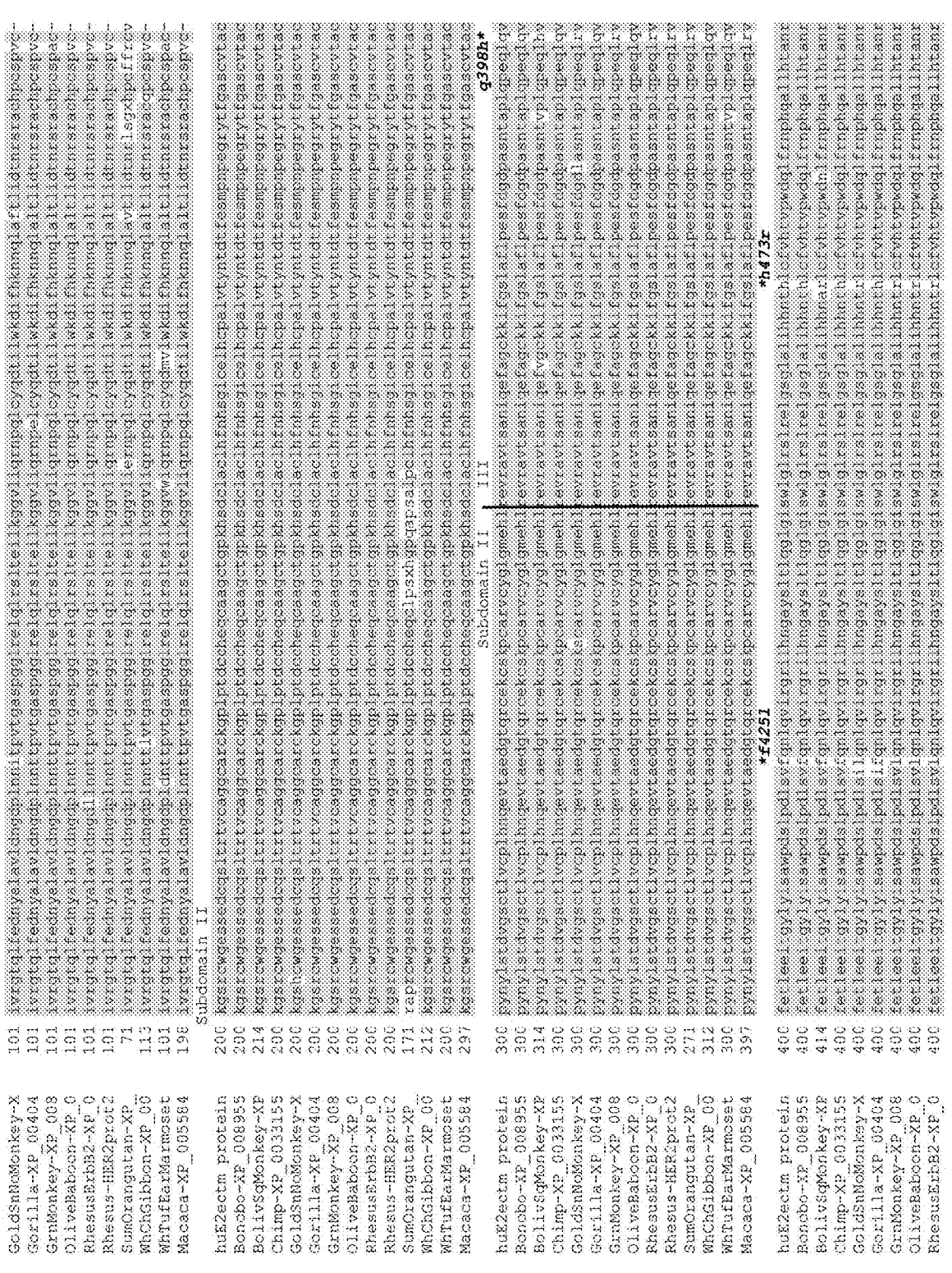

FIG. 8 shows the alignment of 14 protein sequences listed in Table 1. For this alignment, global protein alignment against reference molecule was used, wherein the reference molecule as huE2ectm protein, Region 1 to 687. Fourteen sequences were aligned and the total length of aligned sequences with gaps was 688 amino acids. Parameters: Scoring matrix: BLOSUM 62.

Figure 3A:
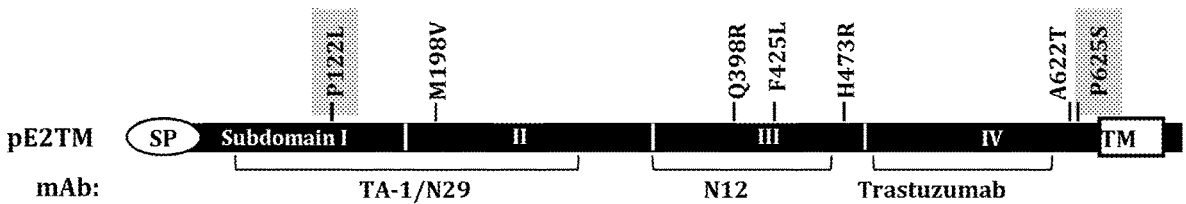
FIGS. 3A, 3B, 3C, 3D, and 3E generally show evolution-selected HER2 vaccine and the corresponding immune response.
Figure 3B:
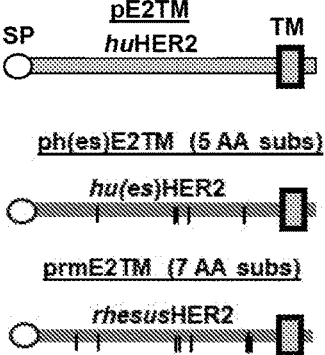

From this panel of 'evolution-selected alterations', 5 amino acids in HER2 ECD were found to be frequently replaced by a common residue (FIG. 8): M198V (ECD subdomain I), Q398R (III), F425L (III), H473R (III) and A622T (IV), see FIG. 3A. BLOSUM scores of these substitutions are all 0 and +1, indicating they are relatively neutral changes. A new HER2 vaccine, ph(es)E2TM, was generated to incorporate these five common substitutions as shown in FIG. 3B.

Figure 7:
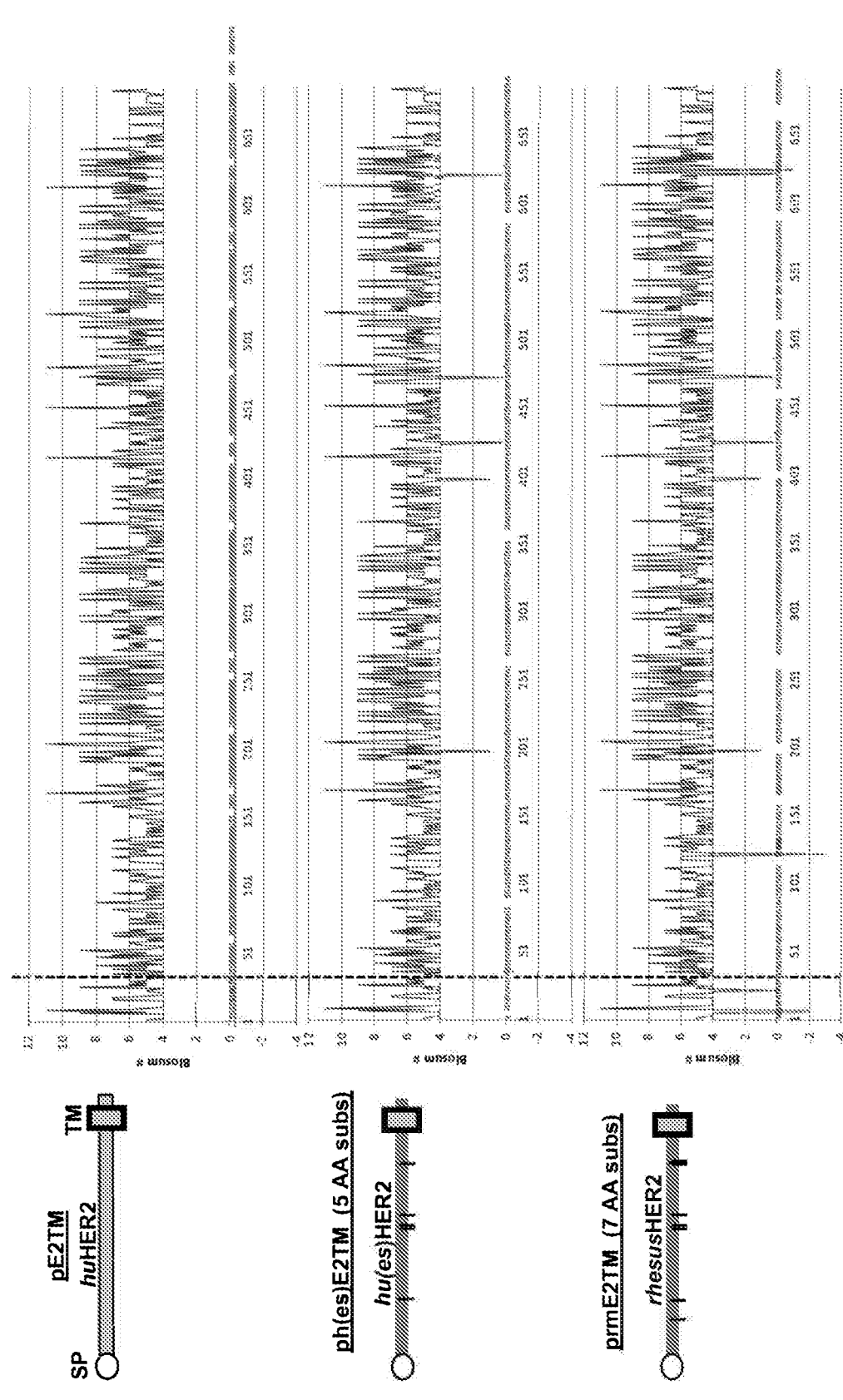
FIG. 7 shows BLOSUM scores of amino acid substitutions in immunogenic HER2 vaccine compositions according to aspects of the present invention. BLOSUM62 scores are plotted for AA residues of indicated HER2 vaccine constructs: pE2TM is human native HER2ectm; ph(es) E2TM is pE2TM with the indicated 5 evolutionary-selected AA substitutions; prmE2TM is rhesus monkey HER2ectm, which differs from human E2ectm by 7 AA residues, as indicated. BLOSUM62 scores are calculated for substituted AA's in reference to human native E2TM.

Alterations in ph(es)E2TM are readily quantifiable (FIG. 7). A rhesus monkey HER2 (rmE2TM) (XM_001090430) encodes 2 additional amino acid substitutions that are more drastic and not commonly observed: P122L in subdomain I (BLOSUM score=−3) and P625S in subdomain IV (score=−2) (shaded blocks) (Fattori E, et al., 2009, Hum. Gene Ther., 20: 253-65. doi: 10.1089/hum.2008.153)

To test whether drastic amino acid substitutions would detract immune response from native HER2, the prmE2TM DNA construct with all 7 residue substitutions was generated for comparison.

Expression and Immunogenicity of ph(es)E2TM and prmE2TM

Figure 3C:
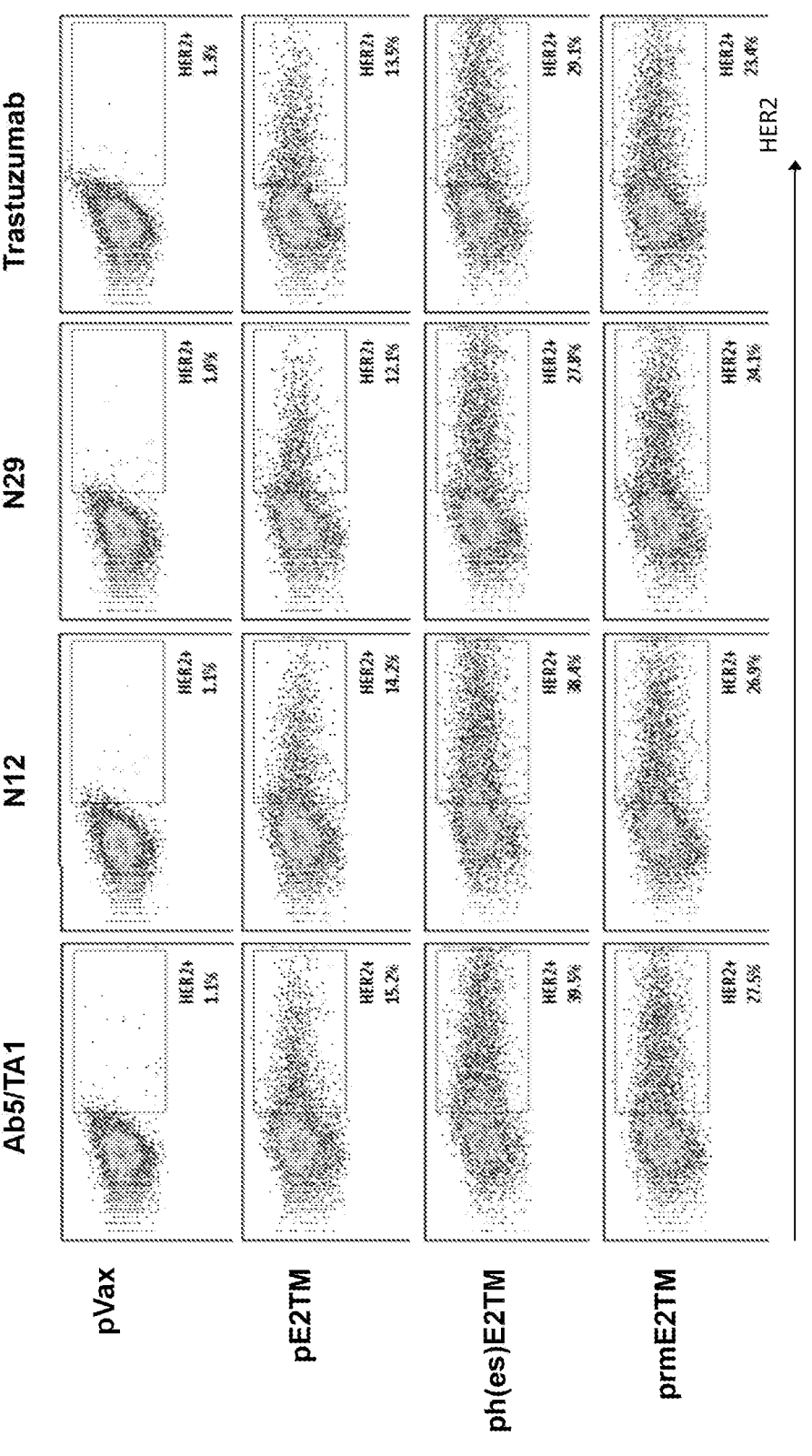

Recombinant protein was measured by flow cytometry using 3T3 cells transiently transfected with ph(es)E2TM or prmE2TM (FIG. 3C). The controls were pVax and pE2TM. Anti-HER2 mAb TA1, N29, N12, and trastuzumab recognized both ph(es)E2TM and rmE2TM, recombinant proteins, indicating preservation of these epitopes.

Figure 3D:
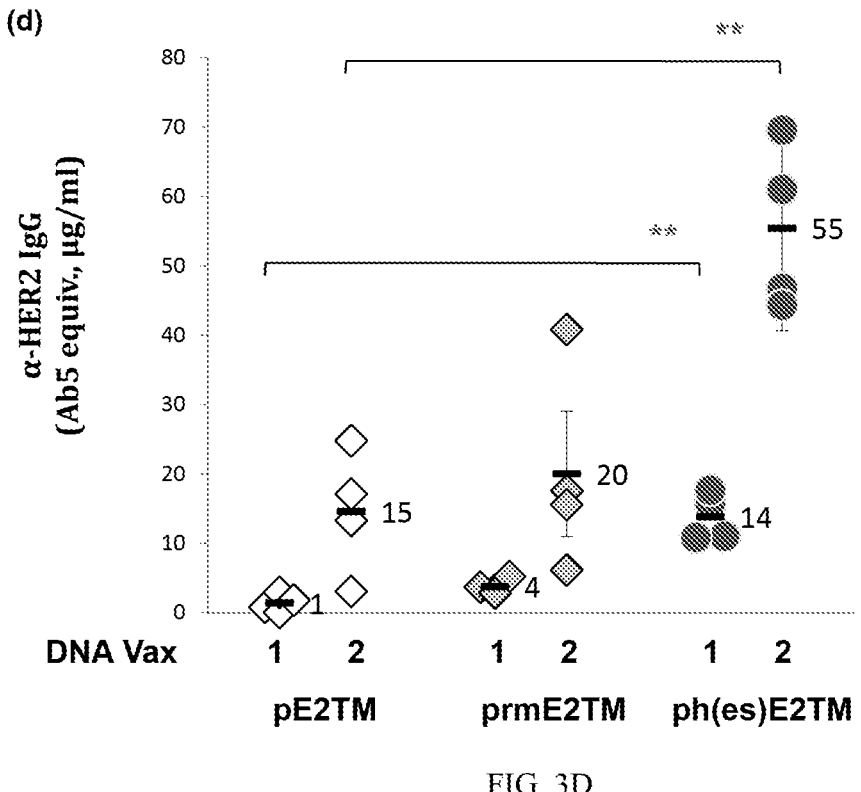
Figure 3E:
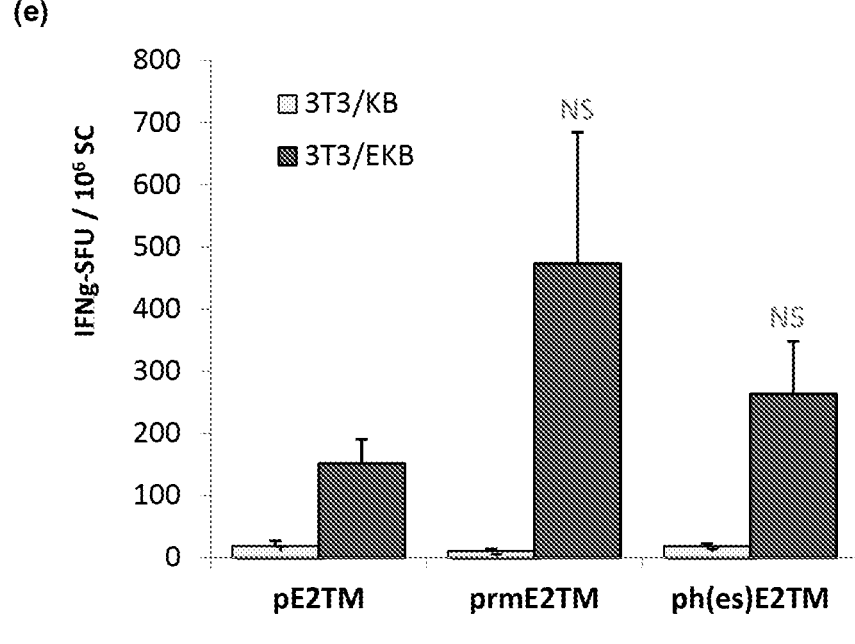

Immunogenicity of ph(es)E2TM and prmE2TM versus native pE2TM was compared. BALB HER2 Tg mice were electrovaccinated twice and anti-HER2 response monitored (FIG. 3D-E). HER2 binding Ab increased by more than three fold in ph(es)E2TM immunized mice (55±6 vs 15±5, p<0.01), showing augmented HER2 immunogenicity from the 5 substitutions. In contrast, prmE2TM did not enhance HER2 Ab response (20±7 vs 15±6 μg/ml)(FIG. 3D). It is possible that P122L and P625S substitutions resulted in neoantigen to detract immunity from native HER2 (FIG. 3D). HER2-specific IFN-γ-producing T cells were induced in pE2TM, prmE2TM and ph(es)E2TM vaccinated mice at 152±39, 474±211 and 264±85 spot-forming units/$10^6$ SC, respectively (FIG. 3E). There may be a trend toward higher T cell response in prmE2TM and ph(Es)E2TM immunized mice, but the difference was not statistically significant.

Figure 4A:
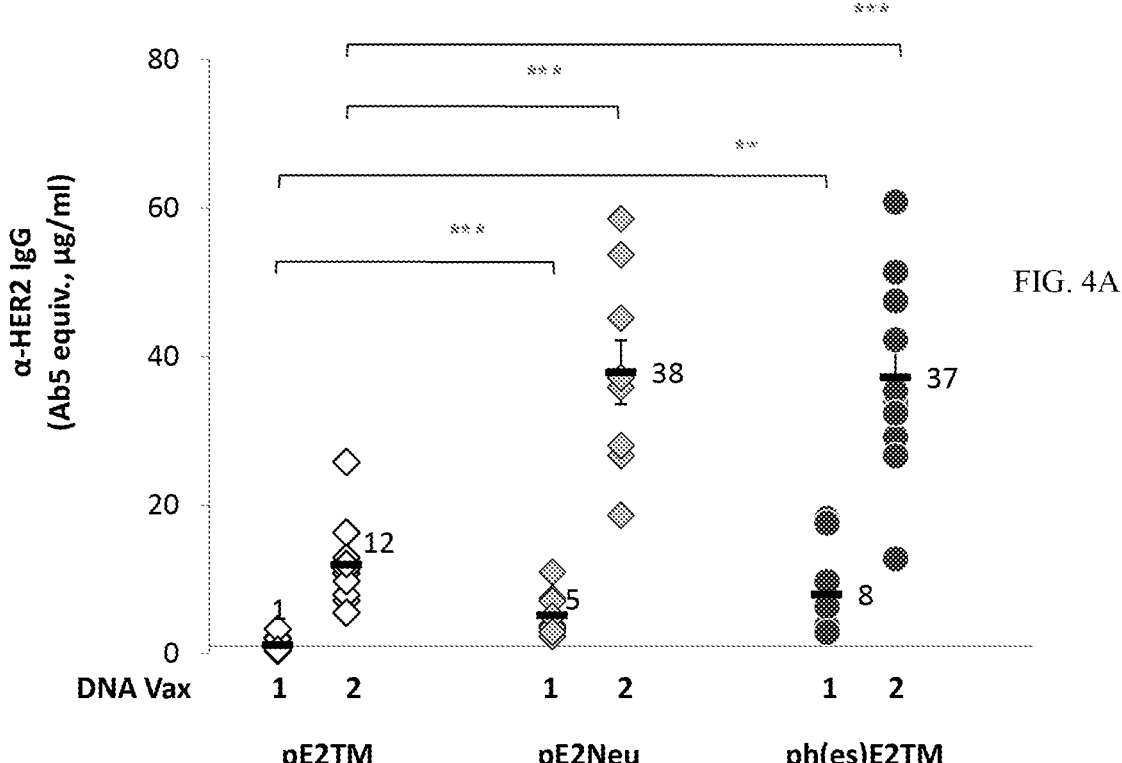
FIG. 4A is a graph showing induction of HER2 immunity by ph(es)E2TM in BALB HER2Tg. BALB HER2Tg mice were electrovaccinated twice with pE2TM, pE2Neu, or ph(es)E2TM. HER2 Ab levels were measured.
Figure 4B:
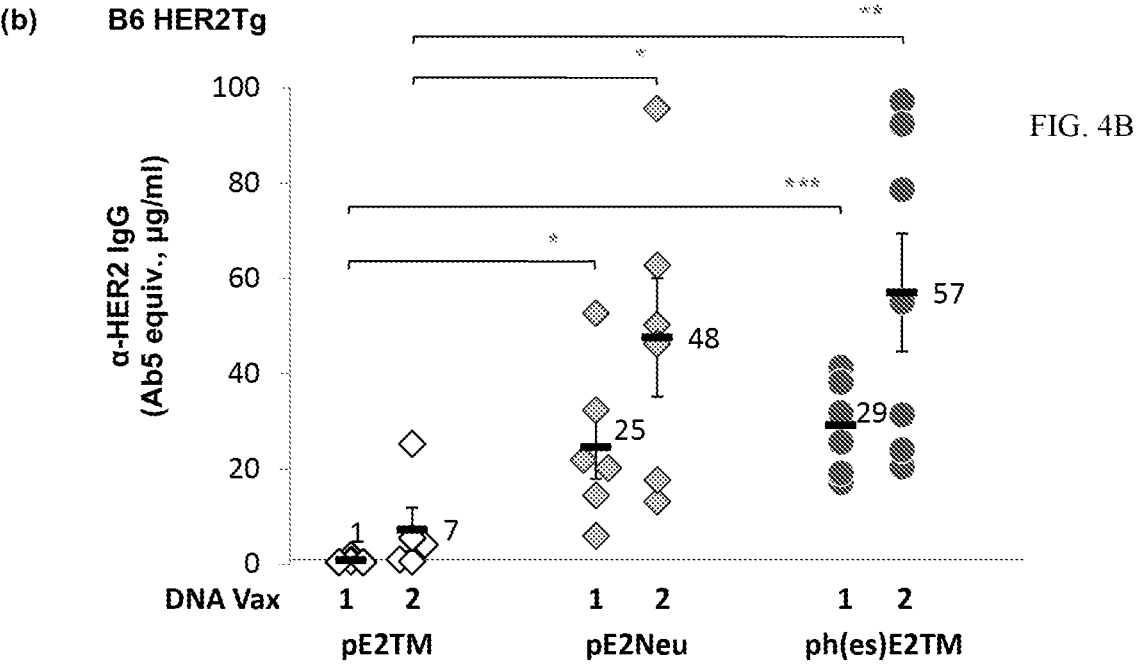
FIG. 4B is a graph showing induction of HER2 immunity by ph(es)E2TM in Treg-depleted B6 HER2 Tg mice. Treg-depleted B6 HER2 Tg mice were electrovaccinated 2× with pE2TM, pE2Neu, or ph(es)E2TM and α-HER2 Ab measured 2 weeks after each vaccination.

Immunogenicity of ph(es)E2TM was also compared with pE2Neu in BALB and B6 HER2 Tg mice. Mice were electrovaccinated twice, 2 weeks apart, and serum was collected two weeks after each vaccination. B6 HER2 Tg mice received mAb PC61 before vaccination to remove Treg. FIG. 4A shows pE2TM, pE2Neu and ph(es)E2TM inducing 12±1.8, 38±4.3 and 37±4.3 μg/ml HER2-binding Ab, respectively, in BALB HER2 Tg mice. ph(es)E2TM and pE2Neu induced comparable levels of HER2 binding IgG even though ph(es)E2TM has only 5 substituted residues. In Treg depleted, twice vaccinated B6 HER2 Tg mice, pE2Neu and ph(es)E2TM induced 48±12.4 μ/ml and 57±12.4 μg/ml HER2-binding Ab, respectively, compared to 7±4.6 μg/ml by pE2TM (FIG. 4B). Therefore, in both BALB and B6 HER2 Tg mice, ph(es)E2TM was as effective as pE2Neu in generating Ab to self HER2. Of the 5 substituted amino acids, four are located in ECD subdomains III and IV. M198V substitution in subdomain I has a BLOSUM score of +1. Incorporation of conservative AA substitutions selected and preserved during evolution resulted in an improved HER2 vaccine for antibody induction.

Figure 4C:
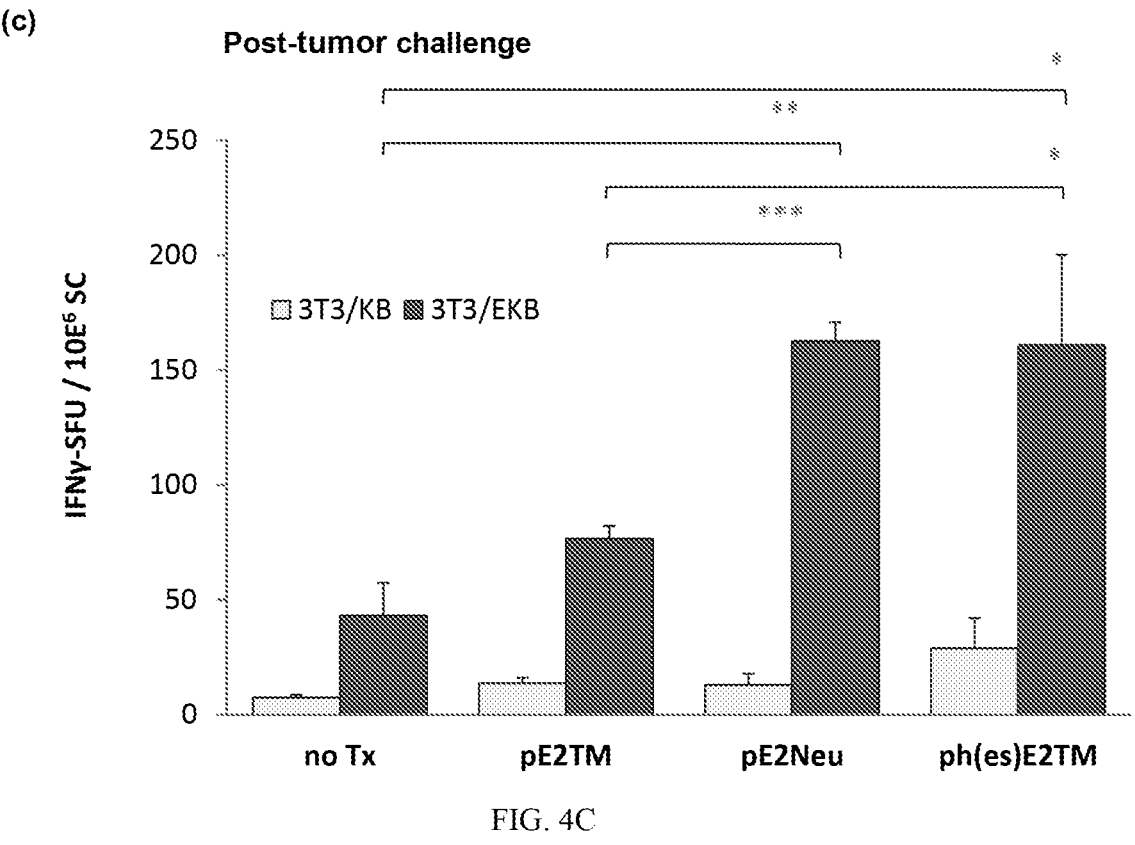
FIG. 4C is a graph showing results from BALB HER2 Tg mice which were inoculated with D2F2/E2t tumors in the mammary fatpad and IFNγ-producing SC were analyzed 4 weeks post tumor inoculation. There were 6-9 mice per group. *p<0.05, p<0.01, *p<0.0001
Figure 4D:
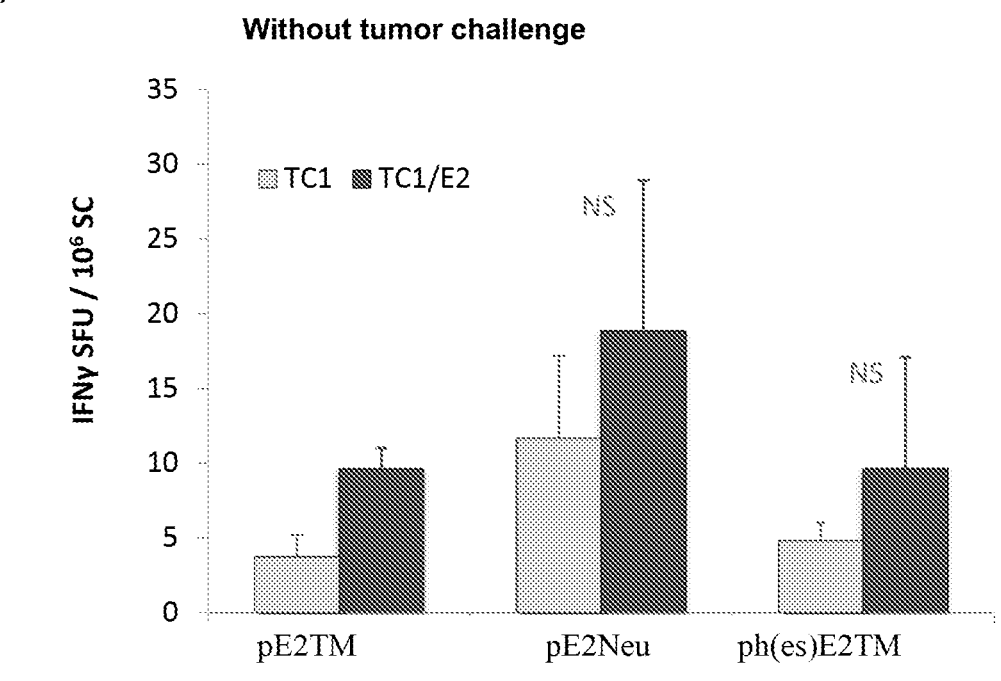
FIG. 4D is a graph showing results from IFNγ-producing SC in B6 HER2 Tg which were evaluated 2 weeks post second vaccination, without tumor inoculation. There were 6-9 mice per group. *p<0.05, p<0.01, *p<0.0001

To measure HER2-specific T cell response, twice-vaccinated BALB HER2 Tg mice received intra-fat pad injection of syngeneic D2F2/E2t mammary tumor cells expressing human HER2 at 2 weeks post-2nd vaccination. Immune SC harvested 3 weeks later showed a significant increase in T cell response in ph(es)E2TM or pE2Neu vaccinated mice, when compared to pE2TM immunization (FIG. 4C). A modest T cell response was induced in B6 HER2 Tg mice regardless of the vaccine. B6 HER2 Tg mice were not challenged with tumors (FIG. 4D). Taken together, ph(es) E2TM, like pE2Neu, induced elevated humoral immunity in both strains of mice and elevated T cell immunity in BALB HER2 Tg mice.

Peptide Binding Profiles of Immune Serum

Figure 5A:
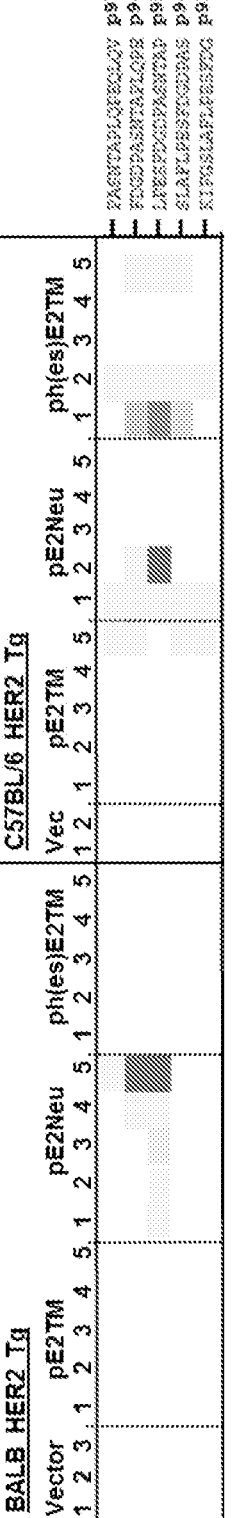
FIGS. 5A and 5B generally show HER2 immune serum epitope mapping. For these studies, immune serum was incubated on peptide microarray slide containing a library of 168 human HER2 15-mer peptides with 11-mer overlaps. Bound antibodies were detected with a fluorescence labeled anti-mouse IgG. Specific binding was expressed by the fold increase in mean pixel value for a particular peptide over the average pixel values of all peptides. A 2-fold increase is considered positive binding.

To determine the epitopes recognized by the immune serum, a library of 168 human HER2 15-mer peptides with 11-mer overlaps was used to evaluate the Ab binding profile. Peptides were covalently immobilized to glass slides. Immune serum was incubated on the peptide microarray slide at 1:200 dilution and bound antibodies were detected with a fluorescence labeled anti-mouse IgG and scanned at 635 nm. Specific binding was expressed by the fold increase in mean pixel value for a particular peptide over the average pixel values of all peptides excluding 3 non-specific binding peptides (85, 121 and 128) (FIG. 5A). An arbitrary cut-off of 2 fold increase was used to identify positive binding peptide.

Figure 5B:
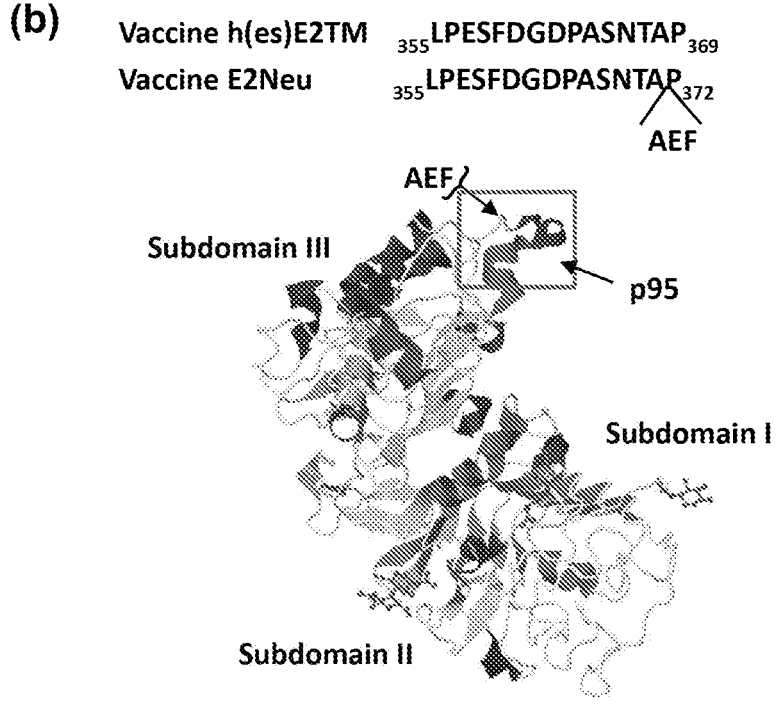

A single P95 355LPESFDGDPASNTAP369 (SEQ ID NO:40) emerged as the target of the immune serum from B6 HER2 Tg mice that received pE2Neu (2/5) or ph(es)E2TM (2/5), but not pE2TM (0/5). In BALB HER2 Tg mice, pE2Neu immune serum recognized p95 (5/5), but not ph(es) E2TM or pE2TM immune serum. p95 in subdomain III is situated on the external surface of HER2 ECD (FIG. 5B). In pE2Neu, the 3 amino acid insertion (AEF) introduced during pE2Neu construction is located between residue 368-369 within p95, and may contribute to the exposure of p95 in E2Neu.

Vaccine Induced Anti-Tumor Immunity

Figure 6A:
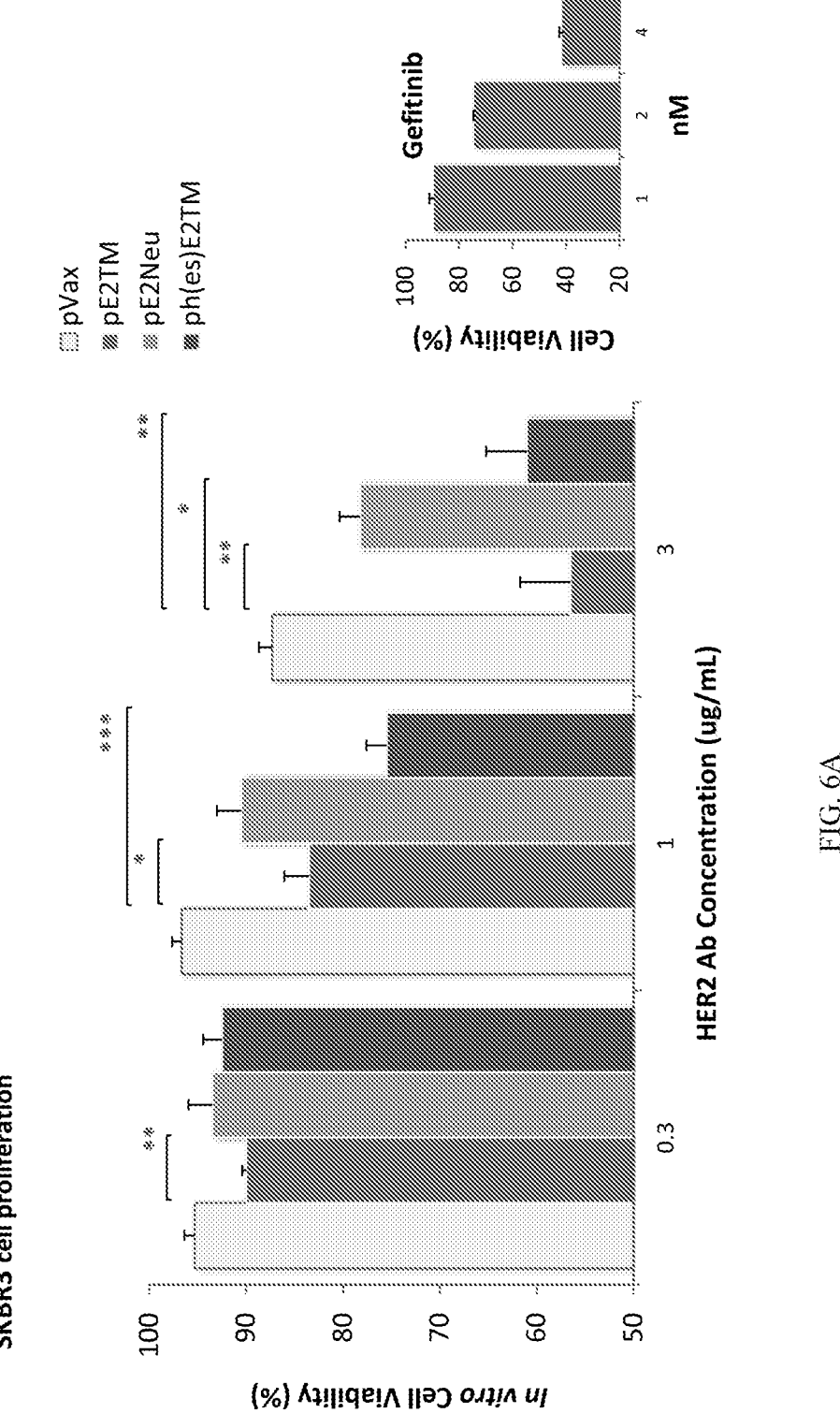
FIGS. 6A and 6B generally show tumor growth inhibition in vitro and in vivo.

Functionality of HER2 immune serum was measured by incubating graded concentrations of immune serum from BALB HER2 Tg mice (FIG. 4A-B) with human SK-BR-3 cells for 48 hours (FIG. 6). Antibody concentrations were calculated based on their HER2 binding activity as determined by flow cytometry. Surviving cells were quantified by Alamar Blue. Reduction in cell survival at 45, 20 and 40%, was observed when the cells were incubated with 3 µg/ml of pE2TM, pE2Neu and ph(es)E2TM immune serum, respectively. At 1 µg/ml, only pE2TM (15% inhibition) and ph(es)E2TM (25% inhibition) immune sera inhibited tumor cell proliferation. Examination of IgG subtypes indicate similar IgG1/IgG2 composition in the three test sera.

Figure 6B:
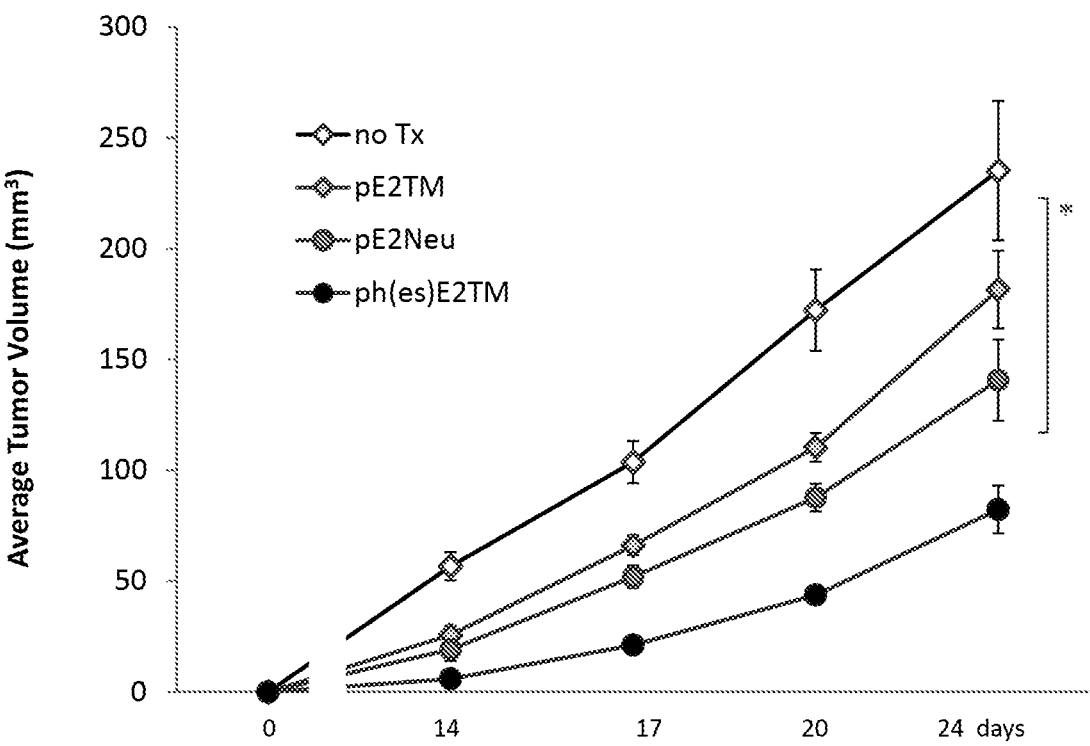

The efficacy of controlling tumor growth in vivo was compared in BALB HER2 Tg mice (FIG. 6B). After two electrovaccinations, mice received 2×10^5 BALB/c D2F2/ E2t cells in their #4 fat pads. Tumor growth was monitored twice weekly. Tumor volume was reduced in mice whether they were vaccinated with pE2Neu or ph(es)E2TM, but reduction was greater in ph(es)E2TM immunized mice.

An effective HER2 cancer vaccine, ph(es)E2TM, was produced by substituting just 5 AA that occur frequently in closely related primates. These five substitutions (M198V, Q398R, F425L, H473R and A622T) are relatively conservative as defined by their BLOSUM scores of 0 to +1. This selection process resulted in a natural design template for generating tumor-associated self-antigens (TAA) vaccines to boost endogenous immunity. Vaccination with ph(es)E2TM induced HER2 immunity that inhibited tumor growth in HER2 Tg mice. Introduction of 2 additional drastic substitutions, P122L (score=-3) and P625S (score=-2), abolished elevated response to HER2, showing that inclusion of uncommon substitutions can be detrimental. Based on these findings with ph(es)E2TM, incorporation of evolution-selected, conservative substitutions may be most appropriate for boosting endogenous immunity to unmodified TAA.

The test vaccines were delivered by intramuscular DNA electroporation. Naked plasmid DNA can be readily generated and modified. It is stable and relatively easy to produce in large quantity. Intramuscular Delivery by i.m. injection is safe and consistent. Application of electroporation at the injection site enhances DNA uptake and expression with little adverse effect.

The importance of preserving wt HER2 ECD subdomains I and II in a vaccine construct was indicated by the poor vaccine response from pNeuE2, in which subdomains I and II were replaced with rat sequences. Critical epitopes may be lost or foreign epitopes created that detract from self HER2. Note that the predicted Nglycosylation sites in pNeuE2 ECD subdomain I differ significantly from wt pE2TM, ph(es) E2TM, or pE2neu. The post-translational glycosylation patterns may also contribute to altered antigenicity.

The ph(es)E2TM recombinant protein is recognized by a panel of four anti-HER2 mAbs that recognize specific epitopes in subdomains I/II, III and IV, showing structural preservation of HER2 ECD. Recombinant rmE2TM was also recognized by these mAbs, but prmE2TM was ineffective at elevating HER2 binding antibodies.

Epitope scanning revealed a linear epitope p95 355LPESFDGDPASNTAP369 (SEQ ID NO:40) preferentially recognized by pE2Neu immune serum from both strains and by ph(es)E2TM immune serum from B6 HER2 Tg mice. Treg depletion in B6 HER2 Tg mice prior to vaccination may result in a broader immune recognition. Overlapping peptides p94, p96 and p97 are also recognized by the reactive immune sera, revealing ESFDGDPASNT (SEQ ID NO:45) as the core peptide. The insertion of AEF between residues 368 and 369 at the C-terminus of p95 may expose p95 for B cell and Ab recognition. ph(es)E2TM does not contain this insertion and the closest substitution is Q398R.

ph(es)E2TM was tested in HER2 Tg mice of BALB/c and C57BL/6 backgrounds and provided elevated immune response in both strains. Although BALB/c and C57BL/6 mice have distinct MHC genotypes, and HER2 Tg mice of these two backgrounds showed very different intrinsic response to HER2 vaccines, ph(es)E2TM induced a stronger HER2 immunity compared to native pE2TM or pE2Neu in either strain. ph(es)E2TM with evolution-selected conservative residue substitutions represents a new and novel principle for vaccine formulation.

Sequences
SEQ ID NO: 1 - *Homo sapiens* (Human; "E2ectm") NP_004439.2 (1-687)
    1 melaalcrwg lllallppga astqvctgtd mklrlpaspe thldmlrhly qgcqvvqgnl -continued

```
   61 eltylptnas lsflqdiqev qgvvliahnq vrqvplqrlr ivrgtqlfed nvalavldng 121 dplnnttpvt gaspgglrel qlrslteilk ggvliqrnpq lcyqdtilwk difhknnqla 181 ltlidtnrsr achpcspmck gsrcwgesse dcqsltrtvc aggcarckgp lptdccheqc 241 aagctgpkhs dclaclhfnh sgicelhcpa lvtyntdtfe smpnpegryt fgascvtacp 301 ynylstdvgs ctlvcplhnq evtaedgtqr cekcskpcar vcyglgmehl revravtsan 361 iqefagckki fgslaflpes fdgdpasnta plqpeqlqvf etleeitgyl yisawpdslp 421 dlsvfqnlqv irgrilhnga ysltlqglgi swlglrslre lgsglalihh nthlcfvhtv 481 pwdqlfrnph qallhtanrp edecvgegla chqlcarghc wgpgptqcvn csqflrgqec 541 veecrvlqgl preyvnarhc lpchpecqpq ngsvtcfgpe adqcvacahy kdppfcvarc 601 psgvkpdlsy mpiwkfpdee gacqpcpinc thscvdlddk gcpaeqrasp ltsiisavvg 661 illvvvlgvv fgilikrrqq kirkytm
```

SEQ ID NO: 2 - h(es)E2ectm (human) (1-687; with substitutions M198V,
Q398R, F425I, H473R, A622T)
```
    1 melaalcrwg lllallppga astqvctgtd mklrlpaspe thldmlrhly qgcqvvqgnl 61 eltylptnas lsflqdiqev qgyvliahnq vrqvplqrlr ivrgtqlfed nyalavldng 121 dplnnttpvt gaspgglrel qlrslteilk ggvliqrnpq lcyqdtilwk difhknnqla 181 ltlidtnrsr achpcspvck gsrcwgesse dcqsltrtvc aggcarckgp lptdccheqc 241 aagctgpkhs dclaclhfnh sgicelhcpa lvtyntdtfe smpnpegryt fgascvtacp 301 ynylstdvgs ctlvcplhnq evtaedgtqr cekcskpcar vcvglgmehl revravtsan 361 igefagckki fgslaflpes fdgdpasnta plqpeqlrvf etleeitgyl yisawpdslp 421 dlsvlqnlqv irgrilhnga ysltlqglgi swlglrslre lgsglalihh ntrlcfvhtv 481 pwdqlfrnph qallhtanrp edecvgegla chqlcarghc wgpgptqcvn csqflrgqec 541 veecrvlqgl preyvnarhc lpchpecqpq ngsvtcfgpe adqcvacahy kdppfcvarc 601 psgvkpdlsy mpiwkfpdee gtcqpcpinc thscvdlddk gcpaeqrasp ltsiisavvg 661 illvvvlgvv fgilikrrqq kirkytm
```

SEQ ID NO: 3 - *Pan paniscus* (Bonobo) XP_0089590.53.1 (1-145, 170-711)
```
    1 melaalcrwg lllallppga astqvctgtd mklrlpaspe thldmlrhly qgcqvvqgnl 61 eltylptnas lsflqdiqev qgyvliahnq vrqvplqrlr ivrgtqlfed nyalavldng 121 dplnnttpvt gaspgglrel qlrslteilk ggvliqrnpq lcyqdtilwk difhknnqla 181 ltlidtnrsr achpcspmck gsrcwgesse dcqsltrtvc aggcarckgp lptdccheqc 241 aagctgpkhs dclaclhfnh sgicelhcpa lvtyntdtfe smpnpegryt fgascvtacp 301 ynylstdvgs ctlvcplhnq evtaedgtqr cekcskpcar vcyglgmehl revravtsan 361 iqefagckki fgslaflpes fdgdpasnta plqpeqlqvf etleeitgyl yisawpdslp 421 dlsvfqnlqv irgrilhnga ysltlqglgi swlglrslre lgsglalihh nthlcfvhtv 481 pwdqlfrnph qallhtanrp edecvgegla chqlcarghc wgpgptqcvn csqflrgqec 541 veecrvlqgl preyvnarhc lpchpecqpq ngsvtcfgpe adqcvacahy kdppfcvarc 601 psgvkpdlsy mpiwkfpdee gtcqpcpinc thscvdlddk gcpaeqrasp ltsiisavvg 661 illvvvlgvv fgilikrrqq kirkytm
```

SEQ ID NO:4 - *Saimiri boliviensis boliviensis* (Bolivian Squirrel Monkey)
XP_010328997.1 (38-701)
```
   38 qvctgtdmkl rlpaspethl dmlrhlvqgc qvvqgnlelt ylptnaslsf lqdiqevqgy 98 vliahnqvrq vplqrlrivr gtqlfednya lavldngdpl dnttpvtgas pgglrelqlr 158 slteilkggv wiqrnpqlcy qdtilwkdif hknnqlaltl idtnrsrach pcspvckgsr
```

-continued

```
218 cwgessedcq sltrtvcagg carckgplpt dccheqcaag ctgpkhsdcl aclhfnhsgi 278 celhcpalvt yntdtfesmp npegrytfga scvtacpvny lstdvgsctl vcplhnqevt 338 aedgtqrcek cskpcarvcy glgmehlrev ravtsaniqe fvgckkifgs laflpesfdg 398 dpasntvplq peqlhvfetl eeitgylyis awpdslpdls vfqnlqvirg rilhngaysl 458 tlqglaiswl glrslrelgs glalihhnar lcfvhtvpwd nlfrnphqal lhtanrpehe 518 cvgkdlachp lcarghcwgp gptqcvncsq flrgqecvee crvlqglpre yvnarhclpc 578 hpecqpqngs vtcsgpeadq cvacahykds pfcvarcpsg vkpdisympi wkfpdeegtc 638 qpcpincths cvdlddkgcp aeqrasplts iisavvgill vmvlglllgi likrrqqkir 698 kytm
```

SEQ ID NO: 5 - *Pan troglodytes* (Chimp) XP_003315512.2 (1-687)
```
  1 melaalcrwg lllallppga astqvctgtd mklrlpaspe thldmlrhly qgcqvvqgnl 61 eltylptnas lsflqdiqev qgyvliahnq vrqvplqrlr ivrgtqlfed nyalavldng 121 dplnnttpvt gaspgglrel qlrslteilk ggvliqrnpq lcyqdtilwk difhknnqla 181 ltlidtnrsr achpcspmck gsrcwgesse dcqsltrtvc aggcarckgp lptdccheqc 241 aagctgpkhs dclaclhfnh sgicelhcpa lvtyntdtfe smpnpegryt fgascvtacp 301 ynylstdvgs ctlvcplhnq evtaedgtqr cekcskpcar vcyglamehl revravtsan 361 iqefagckki fgslaflpes fdgdpasnta plqpeqlqvf etleeitgyl yisawpdslp 421 dlsvfqnlqv irgrilhnga ysltlqglgi swlglrslre lgsglalihh nthlcfvhtv 481 pwdqlfrnph qallhtanrp edecvgegla chqlcarghc wgpgptqcvn csqflrgqec 541 veecrvlqgl preyvnarhc lpchpecqpq ngsvtcfgpe adqcvacahy kdppfcvarc 601 psgvkpdlsy mpiwkfpdek gtcqpcpinc thscvdlddk gcpaeqrasp ltsiisavvg 661 illvvvlgvv fgilikrrqq kirkytm
```

SEQ ID NO: 6 - *Rhinopithecus roxellana* (Gold Snooted No Monkey
XP_010377602.1 (1-687)
```
  1 melaawcrwg lllallppga agtqvctgtd mklrlpaspe thldmlrhly qgcqvvqgnl 61 eltylptdas lsflqdiqev qgyvliahnq vrqvplqrlr ivrgtqlfed nyalavldng 121 dplnnitpvt gaspgglrel qlrslteilk ggvliqrnpq lcvqdtilwk difhknnqla 181 ftlidtnrsr achpcspvck gshcwgesse dcqsltrtvc aggcarckgp lptdccheqc 241 aagctgpkhs dclaclhfnh sgicelhcpa lvtyntdtfe smpnpegryt fgascvtacp 301 ynylstdvgs ctlvcplhnq evtaedgtqr cekcskscar vcyglgmehl revravtsan 361 iqefagckki fgslaflpes fdgdlasnta plqpeqlrvf etleeitgyl yisawpdslp 421 dlsilqnlqv irgrilhnga ysltlqglgi swlglrslre lgsglalihh ntrlcfvhtv 481 pwdqlfrnph qallhtanrp edecvgegla chqlcarghc wgpgptqcvn csqflrgqec 541 veecrvlqgl preyvnarhc lpchpecqpq ngsvtcfgpe adqcvacahy kdppfcvarc 601 psgvkpdlsy mpiwkfpdee gtcqpcpinc thscvdlddk gcpaeqrasp ltsiisavvg 661 illvvvlgvv fgilikrrqq kirkytm
```

SEQ ID NO: 7 - *Gorilla gorilla gorilla* (Gorilla) XP_004041868.1 (1-687)
```
  1 melaalcrwg lllallppga astqvctgtd mklrlpaspe thldmlrhly qgcqvvqgnl 61 eltylptnas lsflqdiqev qgyvliahnq vrqvplqrlr ivrgtqlfed nyalavldng 121 dplnnttpvt gaspgglrel qlrslteilk ggvliqrnpe lcyqdtilwk difhknnqla 181 ltlidtnrsr achpcspvck gsrcwgesse dcqsltrtvc aggcarckgp lptdccheqc 241 aagctgpkhs dclaclhfnh sgicelhcpa lvtyntdtfe smpnpegryt fgascvtacp
```

-continued

```
301 ynylstdvgs ctlvcplhnq evtaedgtqr cekcskpcar vcyglgmehl revravtsan 361 iqefaackki fgslaflpes fdgdpasnta plqpeqlqvf etleeitgyl yisawpdslp 421 dlsifqnlqv irgrilhnga ysltlqglgi swlglrslre lgsglalihh nthlcfvhtv 481 pwdqlfrnph qallhtanrp edecvgegla chqlcarghc wgpgptqcvn csqflrggqec 541 veecrvlqgl preyvnarhc lpchpecqpq ngsvtcfgpe adqcvacahy kdppfcvarc 601 psgvkpdlsy mpiwkfpdee gacqpcpinc thscvdlddk gcpaeqrasp ltsiisavvg 661 illvvvlgvv fgilikrrqq kirkytm
```

SEQ ID NO: 8 - *Chlorocebus sabaeus* (Green Monkey) XP_008011036.1 (1-687)
```
  1 melaawcswg lilallppga agtqvctgtd mklrlpaspe thldmlrhly qgcqvvqgnl 61 eltylptnas lsflqdiqev qgyvliahnq vrqvplqrlr ivrgtqlfed nvalavldng 121 dplnnttpvt gaspgglrel qlrslteilk ggvliqrnpq lcyqdtilwk difhknnqla 181 ltlidtnrsr achpcspack gsrcwgesse dcqsltrtvc aggcarckgp lptdccheqc 241 aagctgpkhs dclaclhfnh sgicelhcpa lvtyntdtfe smpnpegryt fgascvtacp 301 vnylstdvgs ctlvcplhnq evtaedgtqr cekcskpcar vcyglgmehl revravtsan 361 iqefagckki fgslaflpes fdgdpasnta plqpeqlrvf etleeitgyl yisawpdslp 421 dlsvlqnlqv irgrilhnga ysltlqglgi swlglrslre lgsglalihh ntrlcfvhtv 481 pwdqlfrnph qallhtanrp edecvgeala chqlcarghc wgpgptqcvn csqflrggqec 541 veecrvlqgl preyvnarhc lpchpecqpq ngsvtcfgpe adqcvacahy kdppfcvarc 601 psgvkpdlsy mpiwkfpdee gtcqpcpinc thscvdlddk gcpaeqrasp ltsiisavvg 661 illvvvlgvv fgilikrrqq kirkytm
```

SEQ ID NO: 9 - *Papio anubis* (Olive Baboon) XP_003912981.1 (1-687)
```
  1 melaawcrwg lllallppga agtqvctgtd mklrlpaspe thldmlrhly qgcqvvqgnl 61 eltylptnas lsflqdiqev qgyvliahnq vrqvplqrlr ivrgtqlfed nyalavldng 121 dplnnttpvt gaspgglrel qlrslteilk ggvliqrnpq lcyqdtilwk difhknnqla 181 ltlidtnrsr achpcspvck gsrcwgesse dcqsltrtvc aggcarckgp lptdccheqc 241 aagctgpkhs dclaclhfnh sgicelhcpa lvtyntdtfe smpnpegryt fgascvtacp 301 ynvlstdvgs ctlvcplhnq evtaedgtqr cekcskpcar vcyglgmehl revravtsan 361 iqefaackki fgslaflpes fdgdpasnta plqpeqlqvf etleeitgyl yisawpdslp 421 dlsvlqnlqv irgrilhnga ysltlqglgi swlglrslre lgsglalihh ntrlcfvhtv 481 pwdqlfrnph qallhtanrp edecvgegla chqlcarghc wgpgptqcvn csqflrggqec 541 veecrvlqgl preyvnarhc lpchpecqpq ngsvtcfgpe adqcvacahy kdppfcvarc 601 psgvkpdlsy mpiwkfpdee gtcqpcpinc thscvdlddk gcpaeqrasp ltsiisavvg 661 illvvvlgvv fgilikrrqq kirkytm
```

SEQ ID NO: 10 - *Macaca mulatta* (Rhesus) XP_001090430.1 (1-687)
```
  1 melaawyrwg lllallppga agtqvctgtd mklrlpaspe thldmlrhly qgcqvvqgnl 61 eltylptnas lsflqdiqev qgyvliahnq vrqvplqrlr ivrgtqlfed nyalavldng 121 dllnnttpvt gaspgglrel qlrslteilk ggvliqrnpq lcyqdtilwk difhknnqla 181 ltlidtnrsr achpcspvck gsrcwgesse dcqsltrtvc aagcarckgp yptdccheqc 241 aagctgpkhs dclaclhfnh sgicelhcpa lvtyntdtfe smpnpegryt fgascvtacp 301 ynylstdvgs ctlvcplhnq evtaedgtqr cekcskpcar vcyglgmehl revravtsan 361 iqefagckki fgslaflpes fdgdpasnta plqpeqlrvf etleeitgyl yisawpdslp 421 dlsvlqnlqv irgrilhnga ysltlqglgi swlglrslre lgsglalihh ntrlcfvhtv
```

-continued

```
481 pwdqlfrnph qallhtanrp edecvgegla chqlcarghc wgpgptqcvn csqflrgqec 541 veecrvlqgl preyvnarhc lpchpecqpq ngsvtcfgpe adqcvacahy kdppfcvarc 601 psgvkpdlsy mpiwkfpdee gtcqscpinc thscvdlddk gcpaeqrasp ltsiisavvg 661 illvvvlgvv fgilikrrqq kirkytm
```

SEQ ID NO: 11 - *Macaca mulatta* (Rhesus-HER2prot2) US7282365 B2 (#41)
(1-687)

```
  1 melaawyrwg lllallppga agtqvctgtd mklrlpaspe thldmlrhly qgcqvvqgnl 61 eltylptnas lsflqdiqev qgyvliahnq vrqvplqrlr ivrgtqlfed nyalavldng 121 dplnnttpvt gaspgglrel qlrslteilk ggvliqrnpq lcvqdtilwk difhknnqla 181 ltlidtnrsr achpcspvck gsrcwgesse dcqsitrtvc aggcarckgp lptdccheqc 241 aagctgpkhs dclaclhfnh sgicelhcpa lvtyntdtfe smpnpegryt fgascvtacp 301 ynylstdvgs ctlvcplhnq evtaedgtqr cekcskpcar vcyglgmehl revravtsan 361 iqefagckki fgslaflpes fdgdpasnta plqpeqlrvf etleeitgyl yisawpdslp 421 dlsvlqnlqv irgrilhnga ysltlqglgi swlglrslre lgsglalihh ntrlcfvhtv 481 pwdqlfrnph qallhtanrp edecvgegla chqlcaxghc wgpgptqcvn csqflrgqec 541 veecrvlqgl preyvnarhc lpchpecqpq ngsvtcfgpe adqcvacahy kdppfcvarc 601 psgvkpdlsy mpiwkfpdee gtcqpcpinc thscvdlddk gcpaeqxasp ltsiisavvg 661 illvvvlgvv fgilikrrqq kirkytm
```

SEQ ID NO: 12 - *Pongo abelii* (Sumatran Orangutan) XP_009250137.1
(1-221, 229-666)

```
  1 mklrlpaspe thldmlrhly qgcqvvqgnl eltylptnas lsflqdiqev qgyvliahnq 61 vrqvplqrlr ivrgtqlfed nyalavldng dplnnttpvt gaspgglrel qlrslteilk 121 ggvliernpq lcyqdtilwk difhknnqla vtlidtnrls gxhpcffrcv raprcwgess 181 edcqsltrtv caggcarckg plptdccheq clpsxhgpqa psalpclhfn hsgicelhcp 241 alvtyntdtf esmpnpegry tfgascvtac pynylstdvg sctlvcplhn qevtaedgtq 301 rcekcskpca rvcyglgmeh lrevravtsa niqefagckk ifgslaflpe sfdgdpasnt 361 aplqpeqlrv fetleeitgy lyisawpdsl pdlsvfqnlq virgrilhng aysltlqglg 421 iswlglrslr elgsglalih hntrlcfvht vpwdqlfrnp hqallhtanr pedecvgegl 481 achqlcargh cwgpgptqcv ncsqflrgqe cveecrvlqg lpreyvnary clpchpecqp 541 qngsvtcfgp eadqcvacah vkdppfcvar cpsgvkpdls ympiwkfpde egtcqpcpin 601 cthscvdldd kgcpaeqras pltsiisavv gillvvvlgv vfgilikrrq qkirkytm
```

SEQ ID NO: 13 - *Nomascus leucogenys* (WhChGibbon) XP_003278275.1 (37-699)

```
 37 vctgtdmklr lpaspethld mlrhlyqgcq vvqgnlelty lptnaslsfl qdiqevqgyv 97 liahnqvrqv plqrlrivrg tqlfednyal avldngdpln nttlvtgasp gglrelqlrs 157 iteilkggvl iqrnpqlcyq dtilwkdifh knnqlaltli dtnrsracqp cspvckgsrc 217 wgessedcqs ltrtvcaggc arckgpiptd ccheqcaagc tapkhsdcla clhfnhsgic 277 elhcpalvty ntdtfesmpn pegrytfgas cvtacpynyl stdvgsctlv cplhnqevta 337 edgtqrcekc skpcarvcyg lgmehlrevr avtsaniqef agckkifgsl aflpesfdgd 397 pasntaplqp eqlqvfetle eitgylyisa wpdslsdlsv fqnlqvirgr ilhngayslt 457 iqglgiswlg lrslrelgsg lalihhnnrl cfvhtvpwdq ifrnphqall htanrpedec 517 vaeglachql carghcwgpg ptqcvncsqf lrgqecveec rvlqglprey vnarhclpch 577 pecqpqngsv tcfgpeadqc vscahykdpp fcvarcpsgv kpdlsvmpiw kfpdeegtcq
```

-continued

```
637 pcpincthsc vdlddkgcpa eqraspltsi isavvgillv vvlgavfgil ikrrqqkirk 697 ytm
```

SEQ ID NO: 14 - *Callithrix jacchus* (WhTufEarMarmoset) XP_002806904.1
(1-687)
```
  1 melaawcrwg llfallppga agtqvctatd mklrlpaspe thldmlrhly qgcqvvqgnl 61 eltylpanas lsflqdiqev qgyvliahnq vrqvplqrlr ivrgtqlfed nyalavldng 121 dpldnttpvt gaspgglrel qlrslteilk ggvwiqrnpq lcyqdmvlwk difhknnqla 181 ltlidtnrsr achpcspack gsrcwgesse dcqsltrtvc aggcarckgp lptdccheqc 241 aagctgpkhs dclacihfnh sgicelhcpa lvtyntdtfe smpnpegryt fgascvtacp 301 ynylstdvgs ctlvcplhnq evtaedgtqr cekcskpcar vcyglamehl revravtsan 361 iqefagckki fgslaflpes fdgdpasntv plqpeqlqvf etleeitgyl yisawpdslp 421 dlsvfqnlqv irgrilhnga ylltlqglgi swlglrslre lgsglalihh narlcfvhtv 481 pwdnlfrnph qallhtanrp ehecvgkdla chplcarghc wgpgptqcvn csqflrgqec 541 veecrvlqgl preyvnarhc lpchpecqpq ngsvtcsgpe adqcvacahy kdspfcvarc 601 psgvkpdlsv mpiwkfpdee gtcqpcpinc thscvdlddk gcpaeqrasp ltsiisavvg 661 illfmvlgll lgilmkrrqq kirkytm
```

SEQ ID NO: 15 - *Macaca fascicularis* (Macaca) XP_005584091.2 (98-784)
```
 98 melaawyrwg lllallppga tgtqvctgtd mklrlpaspe thldmlrhly qgcqvvqgnl 158 eltylptnas lsflqdiqev qgyvliahnq vrqvplqrlr ivrgtqlfed nyalavldng 218 dplnnttpvt gaspgglrel qlrslteilk ggvliqrnpq lcvqdtilwk difhknnqla 278 ltlidtnrsr achpcspvck gsrcwgesse dcqsltrtvc aggcarckgp lptdccheqc 338 aagctgpkhs dclaclhfnh sgicelhcpa lvtyntdtfe smpnpegryt fgascvtacp 398 vnylstdvgs ctlvcplhnq evtaedgtqr cekcskpcar vcyglmehl revravtsan 458 igefagckki fgslaflpes fdgdpasnta plqpeqlrvf etleeitgyl yisawpdslp 518 dlsvlqnlqv irgrilhnga ysltlqglgi swlglrslre lgsglalihh ntrlcfvhtv 578 pwdqlfrnph qallhtanrp edecvgegla chqlcarghc wgpgptqcvn csqflrgqec 638 veecrvlqgl preyvnarhc lpchpecqpq ngsvtcfgpe adqcvacahy kdppfcvarc 698 psgvkpdlsv mpiwkfpdee gtcqscpinc thscvdlddk gcpaeqrasp ltsiisavvg 758 illvvvlgvv fgilikrrqq kirkytm
```

SEQ ID NO: 16 - Human ERBB2ectm-delta 16 NP_004439.2 (1-632, 649-687)
```
  1 melaalcrwg lllallppga astqvctgtd mklrlpaspe thldmlrhly qgcqvvqgnl 61 eltylptnas lsflqdiqev qgyvliahnq vrqvplqrlr ivrgtqlfed nyalavldng 121 dplnnttpvt gaspgglrel qlrslteilk ggvliqrnpq icyqdtilwk difhknnqla 181 ltlidtnrsr achpcspmck gsrcwgesse dcqsltrtvc aggcarckgp lptdccheqc 241 aagctgpkhs dclaclhfnh sgicelhcpa lvtyntdtfe smpnpegrvt fgascvtacp 301 ynylstdvgs ctlvcplhnq evtaedgtqr cekcskpcar vcyglgmehl revravtsan 361 iqefagckki fgslaflpes fdgdpasnta plqpeqlqvf etleeitgyl yisawpdslp 421 dlsvfqnlqv irgrilhnga ysltlqglgi swlglrslre lgsglalihh nthlcfvhtv 481 pwdqlfrnph qallhtanrp edecvgegla chqlcarghc wgpgptqcvn csqflrgqec 541 veecrvlqgl preyvnarhc lpchpecqpq ngsvtcfgpe adqcvacahy kdppfcvarc 601 psgvkpdlsy mpiwkfpdee gacqpcpinc thspltsiis avvgillvvv lgvvfgilik 661 rrqqkirkyt m
```

-continued

SEQ ID NO: 17 - Human (es)E2ectm-delta 16 (1-632, 649-687; with
substitutions M198V, Q398R, F425L, H473R, A622T)
    1 melaalcrwg lllallppga astqvctgtd mklrlpaspe thldmlrhly qgcqvvqgnl 61 eltylptnas lsflqdiqev qgyvliahnq vrqvplqrlr ivrgtqlfed nyalavldng 121 dplnnttpvt gaspgglrel qlrslteilk ggvliqrnpq lcyqdtilwk difhknnqla 181 ltlidtnrsr achpcspvck gsrcwgesse dcqsltrtvc aggcarckgp lptdccheqc 241 aagctgpkhs dclaclhfnh sgicelhcpa lvtyntdtfe smpnpegryt fgascvtacp 301 ynylstdvgs ctlvcplhnq evtaedgtqr cekcskpcar vcvglamehl revravtsan 361 iqefagckki fgslaflpes fdgdpasnta plqpeqlrvf etleeitgyl yisawpdslp 421 dlsvlqnlqv irgrilhnga ysltlqglgi swlglrslre lgsglalihh ntrlcfvhtv 481 pwdqlfrnph qallhtanrp edecvgegla chqlcarghc wgpgptqcvn csqflrgqec 541 veecrvlqgl preyvnarhc lpchpecqpq ngsvtcfgpe adqcvacahy kdppfcvarc 601 psgvkpdlsy mpiwkfpdee gtcqpcpinc thspltsiis avvgillvvv lgvvfgilik 661 rrqqkirkyt m SEQ ID NO: 18 - Feline E2ectm (wt) Translate of JN990983 (1-687)
    1 melaawcrwg lllallpsga tgtqvctgtd mklrlpaspe thldmlrhly qgcqvvqgnl 61 eltylhanas lsflqdiqev qgyvliahnq vkqvplqrlr ivrgtqlfed nyalavldng 121 dpldsgtpat gaalgglrel qlrslteilk ggvliqrnpq lchqdtilwk difhknnqla 131 lmlidtnrsr acqpcspack dshcwgassg dcqsltrtvc aggcarckgp qptdccheqc 241 aagctgpkhs dclaclhfnh sgicelhcpa lvtyntdtfe smpnpegryt fgascvtacp 301 ynylstdvgs ctlvcplnnq evtaedgtqr cekcskpcar vcyglgmehl rearavtsan 361 iqefvgckki fgslaflpes fegdpasnta plqpeqlrvf ealeeitgyl yisawpdslp 421 nlsvfqnlrv irgrvlhdga ysltlqglgi swlglrslre lgsglalihr nsrlcfvhtv 481 pwdqlfrnph qallhsanrp edecagegla cvplcahghc wgpgptqcvn csqflrgqec 541 veecrvlqgl preyvkdrfc lpchpecqpq ngsvtclgse adqcvacahy kdppfcvarc 601 psgvkpdlsf mpiwkfadee gtcqpcpinc thscadldek gcpaeqrasp vtsiiaavvg 661 illvvvvglv lgilikrrrq kirkytm SEQ ID NO: 19 - Feline (es)E2ectm (1-687; with substitutions A198V,
R398Q, F425L, R473H, T622A)
    1 melaawcrwg lllallpsga tgtqvctgtd mklrlpaspe thldmlrhly qgcqvvqgnl 61 eltylhanas lsflqdiqev qgyvliahnq vkqvplqrlr ivrgtqlfed nyalavldng 121 dpldsgtpat gaalgglrel qlrslteilk ggvliqrnpq lchqdtilwk difhknnqla 181 lmlidtnrsr acqpcspvck dshcwgassg dcqsltrtvc aggcarckgp qptdccheqc 241 aagctgpkhs dclaclhfnh sgicelhcpa lvtyntdtfe smpnpegryt fgascvtacp 301 ynylstdvgs ctlvcplnnq evtaedgtqr cekcskpcar vcyglgmehl rearavtsan 361 iqefvgckki fgslaflpes fegdpasnta plqpeqlqvf ealeeitgyl yisawpdslp 421 nlsvlqnlrv irgrvlhdga ysltlqglgi swlglrslre lgsglalihr nshlcfvhtv 481 pwdqlfrnph qallhsanrp edecagegla cyplcahghc wgpgptqcvn csqflrgqec 541 veecrvlqgl preyvkdrfc lpchpecqpq ngsvtclgse adqcvacahy kdppfcvarc 601 psgvkpdlsf mpiwkfadee gacqpcpinc thscadldek gcpaeqrasp vtsiiaavvg 661 illvvvvglv lgilikrrrq kirkytm -continued SEQ ID NO: 20 - Feline (es)E2ectm-delta16 Feline (es)E2ectm (1-632,
649-687)
```
    1 melaawcrwg lllallpsga tgtqvctgtd mklrlpaspe thldmlrhly qgcqvvqgnl 61 eltylhanas lsflqdiqev qgvvliahnq vkqvplqrlr ivrgtqlfed nvalavldng 121 dpldsgtpat gaalgglrel qlrslteilk ggvliqrnpq lchqdtilwk difhknnqla 181 lmlidtnrsr acqpcspvck dshcwgassg dcqsltrtvc aggcarckgp qptdccheqc 241 aagctgpkhs dclaclhfnh sgicelhcpa lvtyntdtfe smpnpegryt fgascvtacp 301 ynylstdvgs ctlvcplnnq evtaedgtqr cekcskpcar vcyglgmehl rearavtsan 361 iqefvgckki fgslaflpes fegdpasnta plqpeqlqvf ealeeitgyl yisawpdslp 421 nlsvlqnlrv irgrvlhdga ysltlqglgi swlglrslre lgsglalihr nshlcfvhtv 431 pwdqlfrnph qallhsanrp edecagegla cyplcahghc wgpgptqcvn csqflrgqec 541 veecrvlqgl preyvkdrfc lpchpecqpq ngsvtclgse adqcvacahy kdppfcvarc 601 psgvkpdlsf mpiwkfadee gacqpcpinc thspvtsiia avvgillvvv vglvlgilik 661 rrrqkirkvt m
```

SEQ ID NO: 21 - Dog E2ectm(wt) NP_001003217 (1-687)
```
    1 melaawcrwg lllallpsga agtavctgtd mklrlpaspe thldmlrhly qgcqvvqgnl 61 eltylpanas lsflqdiqev qgyvliahsq vrqiplqrlr ivrgtqlfed nyalavldng 121 dpleggipap gaapgglrel qlrslteilk ggvliqrspq lchqdtilwk dvfhknnqla 131 ltlidtnrsr acppcspack dahcwgassg dcqsltrtvc aggcarckgp qptdccheqc 241 aagctgpkhs dclaclhfnh sgicelhcpa lvtyntdtfe smpnpegryt fgascvtscp 301 ynylstdvgs ctlvcplnnq evtaedgtqr cekcskpcar vcvglgmehl revravtsan 361 igefagckki fgslaflpes fegdpasnta plqpeqlrvf ealeeitgyl yisawpdslp 421 nlsvfqnlrv irgrvlhdga ysltlqglgi swlglrslre lgsglalihr narlcfvhtv 431 pwdqlfrnph qallhsanrp eeecvgegla cyplcahghc wgpgptqcvn csqflrgqec 541 veecrvlqgl preyvkdryc lpchsecqpq nasvtcfgse adqcvacahy kdppfcvarc 601 psgvkpdlsf mpiwkfadee gtcqpcpinc thscadldek gcpaearasp vtsiiaavvg 661 illavvvglv lgilikrrrq kirkvtm
```

SEQ ID NO: 22 - Dog (es)E2ectm NP_001003217 (1-687; with substitutions
A198V, R398Q, F425L, R473H, T622A)
```
    1 melaawcrwg lllallpsga agtavctgtd mklrlpaspe thldmlrhly qgcqvvqgnl 61 eltylpanas lsflqdiqev qgyvliahsq vrqiplqrlr ivrgtqlfed nyalavldng 121 dplegaipap gaapgglrel qlrslteilk ggvliqrspq lchqdtilwk dvfhknnqla 181 ltlidtnrsr acppcspvck dahcwgassg dcqsltrtvc aggcarckgp qptdccheqc 241 aagctgpkhs dclaclhfnh sgicelhcpa lvtvntdtfe smpnpegryt fgascvtscp 301 ynylstdvgs ctlvcplnnq evtaedgtqr cekcskpcar vcyglgmehl revravtsan 361 iqefagckki fgslaflpes fegdpasnta plqpeqlqvf ealeeitgyl yisawpdslp 421 nlsvlqnlrv irgrvlhdga ysltlqglgi swlglrslre lgsglalihr nahlcfvhtv 481 pwdqlfrnph qallhsanrp eeecvgegla cyplcahghc wgpgptqcvn csqflrgqec 541 veecrvlqgl preyvkdryc lpchsecqpq ngsvtcfgse adqcvacahy kdppfcvarc 601 psgvkpdlsf mpiwkfadee gacqpcpinc thscadldek gcpaeqrasp vtsiiaavvg 661 illavvvglv lgilikrrrq kirkvtm
```

-continued

SEQ ID NO: 23 - Dog (es)E2ectm-delta16 Dog (es)E2ectm (1-632, 649-687)
    1 melaawcrwg lllallpsga agtqvctgtd mklrlpaspe thldmlrhly qgcqvvqgnl 61 eltylpanas lsflqdiqev qgyvliahsq vrqiplqrlr ivrgtqlfed nyalavldng 121 dpleggipap gaapgglrel qlrslteilk ggvliqrspq lchqdtilwk dvfhknnqla 181 ltlidtnrsr acppcspvck dahcwgassg dcqsltrtvc aggcarckgp qptdccheqc 241 aagctgpkhs dclaclhfnh sgicelhcpa lvtyntdtfe smpnpegryt fgascvtscp 301 ynylstdvgs ctlvcpinnq evtaedgtqr cekcskpcar vcyglgmehl revravtsan 361 iqefagckki fgslaflpes fegdpasnta plqpeqlqvf ealeeitgvl yisawpdslp 421 nlsvlqnlrv irgrvlhdga ysltlqglgi swlglrslre lgsglalihr nahlcfvhtv 481 pwdqlfrnph qallhsanrp eeecvgegla cyplcahghc wgpgptqcvn csqflrgqec 541 veecrvlqgl pryvvkdryc lpchsecqpq ngsvtcfgse adqcvacahy kdppfcvarc 601 psgvkpdlsf mpiwkfadee gacqpcpinc thspvtsiia avvgillavv vglvlgilik 661 rrrqkirkyt m ERBB2 cDNAs for human, cat, dog; wt, (es), (es)d16
Technical note: The feline ERBB2 cDNAs, for example, are derived from
accession #JN990983 (which inventors cloned). This has a 135 nt 5' UTR,
where the orf begins at nt 136. The numbering of the feline ERBB2 cDNA
derivatives is based on this. In the case of (es) sequences, the sub-
stitutions are indicated. Finally, since the ectm vaccines include only the
first ~687 codons, a stop codon was added, as indicated.
SEQ ID NO: 24 - Homo sapiens (Human; "E2ectm") NM_004448 (1-2061, +TGA)
    1 atggagctgg cggccttgtg ccgctggggg ctcctcctcg ccctcttgcc ccccggagcc 61 gcgaacaccc aagtgtgcac cggcacagac atgaagctgc ggctccctgc cagtcccgag 121 acccacctgg acatgctccg ccacctctac cagggctgcc aggtggtgca gggaaacctg 181 gaactcacct acctgcccac caatgccagc ctgtccttcc tgcaggatat ccaggaggtg 241 cagggctacg tgctcatcgc tcacaaccaa gtgaggcagg tcccactgca gaggctgcgg 301 attgtgcgag gcacccagct ctttgaggac aactatgccc tggccgtgct agacaatgga 361 aacccgctaa acaataccac ccctgtcaca ggggcctccc aggaggcct gcgggagcta 421 cagcttcgaa gcctcacaga gatcttgaaa ggaggggtct tgatccagcg gaacccccag 481 ctctgctacc aggacacgat tttgtggaag gacatcttcc acaagaacaa ccagctggct 541 ctcacactga tagacaccaa ccgctctcgg gcctgccacc cctgttctcc gatgtgtaag 601 ggctcccgct gctggggaga gagttctgag gattgtcaga gcctgacgcg cactgtctgt 661 gccgatggct gtgcccgcta caagggacca ctgcccactg actgctgcca tgagcagtgt 721 gctgccggct gcacgggccc caagcactct gactgcctgg cctgcctcca cttcaaccac 781 agtggcatct gtgagctgca ctgcccagcc ctggtcacct acaacacaga cacgtttgag 841 tccatgccca tcccgaggg ccggtataca ttcggcgcca gctgtgtgac tgcctgtccc 901 tacaactacc tttctacgga cgtgggatcc tgcaccctcg tctgcccct gcacaaccaa 961 aaggtgacag cagagaatgg aacacagcgg tgtgagaagt gcagcaagcc ctgtgcccga 1021 gtgtgctatg gtctgggcat ggagcacttg cgagaggtga gggcagttac cagtgccaat 1081 atccaggagt tgctggctg caagaagatc tttgggagcc tggcatttct gccggagagc 1141 tttgatgggg acccagcctc caacactgcc ccgctccagc cagagcagct ccaagtgttt 1201 gagactctgg aagagatcac aggttaccta tacatctcag catggccgga cagcctgcct 1261 gacctcagcg tcttccagaa cctgcaagta tccggggac aaattctgca caatgacgcc 1321 tactcgctga ccctgcaagg gctgggcatc agctggctgg gctgcgctc actgagggaa 1381 ctgggcagtg gactggccct catccaccat aacacccacc tctgcttcgt gcacacggtg -continued

```
1441 ccctgggacc agctctttcg gaacccgcac caagctctgc tccacactgc caaccggcca 1501 gaggacgagt gtgtgggcga gggcctggcc tgccaccagc tgtgcgcccg agggcactgc 1561 tggggtccag ggcccaccca gtgtgtcaac tgcagccagt ccttcggggg ccaggagtgc 1621 gtggaggaat gccgagtact gcagggggctc cccagggagt atgtgaatgc caggcactgt 1681 ttgccgtgcc accctgagtg tcagccccag aatggctcag tgacctgttt tggaccggag 1741 gctgaccagt gtgtggcctg tgcccactat aaggaccctc ccttctgcgt ggcccgctgc 1801 cccagcggtg tgaaacctga cctctcctac atgcccatct ggaagtttcc agatgaggag 1861 ggcgcatgcc agccttgccc catcaactgc acccactcct gtgtggacct ggatgacaag 1921 ggctgccccg ccgagcagag agccagccct ctgacgtcca tcatctctgc ggtggttggc 1981 attctgctgg tcgtggtctt gggggtagtc tttaggatcc tcatcaagcg acggcagcag 2041 aagatccgga agtacacgat gtga
```

SEQ ID NO: 25 -h(es)E2tm (human)

```
1 atggagctgg cggccttgtg ccgctggggg ctcctcctcg ccctcttgcc ccccggagcc 61 gcgagcaccc aagtgtgcac cggcacagac atgaagctgc ggctccctgc cagtcccgag 121 acccacctgg acatgctccg ccacctctac cagggctgcc aggtggtgca gggaaacctg 181 aaactcacct acctgcccac caatgccagc ctgtccttcc tgcaagatat ccaggaggta 241 cagggctacg tgctcatcgc tcacaaccaa gtgaggcagg tcccactgca gaggctgcgg 301 attgtgcgag gcacccagct ctttgaggac aactatgccc tggccgtgct agacaatgga 361 gacccgctga caataccac ccctgtcaca ggggcctccc aggaggcct gcgggagctg 421 cagcttcgaa gcctcacaga gatcttgaaa ggagggtct tgatccagcg gaaccccccag 481 ctctactacc aagacacgat tttgtgaaag gacatcttcc acaagaacaa ccagctggct 541 ctcacactga tagacaccaa ccgctctcgg gcctgccacc cctgttctcc ggtgtgtaag 601 ggctcccgct gctggggaga gagttctgag gattgtcaga gcctgacgcg cactgtctgt 661 gccggtggct gtgcccgctg caaggggcca ctgcccactg actgctgcca tgagcagtgt 721 gctgccggct gcacgggccc caagcactct gactgcctgg cctgcctcca cttcaaccac 781 agtggcatct gtgagctgca ctgcccagcc ctggtcacct acaacacaga cacgtttgaa 841 tccatgccca atcccgaggg ccggtataca ttcggcgcca gctgtgtgac tgcctgtccc 901 tacaactacc tttctacgga cgtgggatcc tgcaccctcg tctgccccct gcacaaccaa 961 gaggtgacag cagaggatgg aacacagcgg tgtgagaagt gcagcaagcc ctgtgcccga 1021 gtgtgctatg gtctgggcat ggagcacttg cgagaggtga gggcagttac cagtgccaat 1081 atccaggagt ttgctggcta caagaaaatc tttgggagcc tggcatttct gccggagagc 1141 tttgatgggg acccagcctc caacactgcc ccgctccagc cagagcagct cagagtgttt 1201 gagactctgg aagagatcac aggttaccta tacatctcag catggccgga cagcctgcct 1261 gacctcagcg tcctccagaa cctgcaagta atccggggac gaattctgca caatggcgcc 1321 tactcgctga ccctgcaagg gctgggcatc agctggctgg ggctgcgctc actgagggaa 1381 ctgggcagtg gactggccct catccaccat aacacccgcc tctgcttcgt gcacacggtg 1441 ccctgggacc agctctttcg gaacccgcac caagctctgc tccacactgc caaccggcca 1501 gaggacgagt gtgtgggcga gggcctggcc tgccaccagc tgtgcgcccg agggcactgc 1561 tggggtccag ggcccaccca gtgtgtcaac tgcagccagt ccttcggggg ccaggagtgc 1621 gtggaggaat gccgagtact gcagggggctc cccagggagt atgtgaatgc caggcactgt 1681 ttgccgtgcc accctgagta tcagccccag aatagctcag tgacctgttt tggaccggag
```

-continued

```
1741 gctgaccagt gtgtggcctg tgcccactat aaggaccctc ccttctgcgt ggcccgctgc 1801 cccagcggtg tgaaacctga cctctcctac atgcccatct ggaagtttcc agatgaggag 1861 ggcacatgcc agccttgccc catcaactgc acccactcct gtgtggacct ggatgacaag 1921 ggctgccccg ccgagcagag agccagccct ctgacgtcca tcatctctgc ggtggttggc 1981 attctgctag tcgtgatctt ggaggtggtc tttgggatcc tcatcaagcg acggcagcaa 2041 aagatccgga agtacacgat gtaa
```

SEQ ID NO:26 - Human E2ectm-delta 16 NM_004448 (1-1898, 1947-2061, +TAA)

```
   1 atggagctgg cggccttgtg ccgctggggg ctcctcctcg ccctcttgcc ccccggagcc 61 gcgagcaccc aagtgtgcac cggcacagac atgaagctgc ggctccctgc cagtcccgag 121 acccacctgg acatgctcca ccacctctac cagggctgcc aggtggtgca gggaaacctg 181 gaactcacct acctgcccac caatgccagc ctgtccttcc tgcaggatat ccaggaggtg 241 cagggctacg tgctcatcgc tcacaaccaa gtgaggcagg tcccactgca gaggctgcgg 301 attgtgcgag gcacccagct ctttgaggac aactatgccc tggccgtgct agacaatgga 361 gacccgctga acaataccac ccctgtcaca ggggcctccc aggaggcct gcgggagctg 421 cagcttcgaa gcctcacaga gatcttgaaa ggaggggtct tgatccagcg gaacccccag 481 ctctgctacc aggacacgat tttgtggaag gacatcttcc acaagaacaa ccagctggct 541 ctcacactga tagacaccaa ccgctctcgg gcctgccacc cctgttctcc gatgtgtaag 601 ggctcccgct gctgggaaga gagttctgag gattgtcaga gcctgacgcg cactgtctgt 661 gccgatggct gtgcccgcta caaggggcca ctgcccacta actgctgcca tgagcagtgt 721 gctgccggct gcacgggccc caagcactct gactgcctgg cctgcctcca cttcaaccac 781 agtggcatct gtgagctgca ctgcccagcc ctggtcacct acaacacaga cacgtttgag 841 tccatacca atcccgaggg ccggtataca ttcggcgcca gctgtgtgac tgcctgtccc 901 tacaactacc tttctacgga cgtgggatcc tgcaccctcg tctgcccccct gcacaaccaa 961 aaggtgacag cagagaatgg aacacagcgg tgtgagaagt gcagcaagcc ctgtgcccga 1021 gtgtgctatg gtctgggcat ggagcacttg cgagaggtga gggcagttac cagtgccaat 1081 atccaggagt ttgctggctg caagaagatc tttgggagcc tggcatttct gccggagagc 1141 tttgatggga acccagcctc caacactgcc ccgctccagc cagagcagct ccaagtgttt 1201 gagactctgg aagagatcac aggttaccta tacatctcag catggccgga cagcctgcct 1261 gacctcagcg tcttccagaa cctgcaagta atccggggac gaattctgca caatggcgcc 1321 tactcgctga ccctgcaagg gctgggcatc agctggctgg ggctgcgctc actgagggaa 1381 ctgggcagtg gactggccct catccaccat aacacccacc tctgcttcgt gcacacggtg 1441 ccctgggacc agctctttcg gaacccgcac caagctctgc tccacactgc caaccggcca 1501 gaggacgagt gtgtgggcga gggcctggcc tgccaccagc tgtgcgcccg agggcactgc 1561 tggggtccag ggcccaccca gtgtgtcaac tgcagccagt ccttcggggg ccaggagtgc 1621 gtggaggaat gccgagtact gcaggggctc cccagggagt atgtgaatgc caggcactgt 1681 ttgccgtgcc accctgagtg tcagccccag aatggctcag tgacctgttt tggaccggag 1741 gctgaccagt gtgtggcctg tgcccactat aaggaccctc ccttctgcgt ggcccgctgc 1801 cccagcggtg tgaaacctga cctctcctac atgcccatct ggaagtttcc agatgaggag 1861 ggcgcatgcc aaccttgccc catcaactgc acccactccc tctgacgtc catcatctct 1921 gcggtggttg gcattctgct ggtcgtggtc ttgggggtgg tctttgggat cctcatcaag 1981 cgacggcagc agaagatccg gaagtacacg atgtaa
```

-continued

SEQ ID NO: 27 - Human (es)E2ectm-delta 16
```
   1 atggaactgg cgaccttgtg ccgctggggg ctcctcctcg ccctcttgcc ccccggagcc 61 gcgagcaccc aagtgtgcac cggcacagac atgaagctgc ggctccctgc cagtcccgag 121 acccacctgg acatgctccg ccacctctac cagggctgcc aggtggtgca gggaaacctg 181 gaactcacct acctgcccac caatgccagc ctgtccttcc tgcaggatat ccaggaggtg 241 cagggctacg tgctcatcgc tcacaaccaa gtgaggcagg tcccactgca gaggctgcgg 301 attgtgcgag gcacccagct ctttgaggac aactatgccc tggccgtgct agacaatgga 361 gacccgctga acaataccac ccctgtcaca ggggcctccc aggaggcct gcgggagctg 421 cagcttcgaa gcctcacaga gatcttgaaa ggaggggtct tgatccagcg gaacccccag 481 ctctgctacc aggacacgat tttgtggaag gacatcttcc acaagaacaa ccagctggct 541 ctcacactga tagacaccaa ccgctctcgg gcctgccacc cctgttctcc ggtgtgtaag 601 ggctcccgct gctggggaga gagttctgag gattgtcaga gcctgacgcg cactgtctgt 661 gccggtggct gtgcccgctg caaggggcca ctgcccactg actgctgcca tgagcagtgt 721 gctgccggct gcacgggccc caagcactct gactgcctgg cctgcctcca cttcaaccac 781 agtggcatct gtgagctgca ctgcccagcc ctggtcacct acaacacaga cacgtttgag 841 tccatgccca atcccgaggg ccggtataca ttcggcgcca gctgtgtgac tgcctgtccc 901 tacaactacc tttctacgga cgtaggatcc tgcaccctcg tctgcccct gcacaaccaa 961 gaggtgacag cagaggatgg aacacagcgg tgtgagaagt gcagcaagcc ctatgcccga 1021 gtgtgctatg gtctgggcat ggagcacttg cgagaggtga gggcagttac cagtgccaat 1081 atccaggagt ttgctggctg caagaagatc tttgggagcc tggcatttct gccggagagc 1141 tttgatgggg acccagcctc caacactgcc ccgctccagc cagagcagct cagagtgttt 1201 gagactctgg aaaagatcac aggttaccta tacatctcag catggccgga cagcctgcct 1261 gacctcagcg tcctccagaa cctgcaaata tcccggggac gaattctgca caatggcgcc 1321 tactcgctga ccctgcaagg gctgggcatc agctggctgg ggctgcgctc actgaggaaa 1381 ctgggcagtg gactggccct catccaccat aacaccccgc tctgcttcgt gcacacggtg 1441 ccctgggacc agctctttcg gaacccgcac caagctctgc tccacactgc caaccggcca 1501 gaggacgagt gtgtgggcga gggcctggcc tgccaccagc tgtgcgcccg agggcactgc 1561 tggggtccag gcccaccca gtgtgtcaac tgcagccagt ccttcggggg ccaggagtgc 1621 gtggaggaat gccgagtact gcaagggctc cccagggagt atgtgaatgc caagcactgt 1681 ttgccgtgcc accctgagtg tcagccccag aatggctcag tgacctgttt tggaccggag 1741 gctgaccagt gtgtggcctg tgcccactat aaggaccctc ccttctgcgt ggcccgctgc 1801 cccagcggtg tgaaacctga cctctcctac atgcccatct ggaagtttcc agatgaggag 1861 ggcacatgcc agccttgccc catcaactgc acccactcct gtgtggacct ggatgacaag 1921 ggctgccccg ccgagcagag agccagccct ctgacgtcca tcatctctgc ggtggttggc 1981 attctgctgg tcgtggtctt ggggggtggtc tttgggatcc tcatcaagcg acggcagcag 2041 aagatccgga agtacacgat gtaa
```

SEQ ID NO: 28 - Feline E2ectm (wt) JN990983 (136-2196, +TGA)
```
   1 atggagctgg cggcctggtg ccgctggggg ctcctcctcg ccctcctgcc ctccggagcc 61 acgggcaccc aagtgtacac cggcacagac atgaagctgc ggctcccagc cagtcccgag 121 acccacctgg acatgctccg ccacctctac cagggctgtc aagtgataca gggcaacctg 181 gagctcacct acctgcatgc caatgccagc ctctccttcc tgcaggatat ccaggaggtg
```

-continued

```
 241 caaggctatg tgctcattgc ccacaaccaa gtgaaacagg tcccactgca gaggctacga 301 atcgtgcgag gcacccagct ctttgaggac aactacgccc tggccgtgct ggacaacgga 361 gacccactgg acagtggcac ccctgctaca ggggctgccc taggagggct gcgggagctg 421 cagctccgaa gcctcacaga gatcctgaag ggaggggtcc tcattcagcg gaacccgcag 481 ctctgccacc aggacacgat tctgtggaag gacatcttcc acaagaacaa ccagctggcc 541 ctcatgctga tagacaccaa ccgctctcgg gcctgccaac cctgttctcc agcttgtaaa 601 gactcccact gctggggagc aagttccggg gactgtcaga gcttgactcg aactgtctgt 661 gctggcggct gtgcccgctg caagggcccg cagcccaccg actgctgcca cgagcaatgt 721 gctgctggct gcacgggccc caagcattct gactgcctgg cctgcctcca cttcaaccac 781 agtggcatct gtgagctgca ctgcccagcc ctggtcacct acaacacgga caccttcgaa 841 tccatgccca accctgaggg ccgttatacc ttcggtgcca gctgtgtgac tgcctgtccc 901 tacaactacc tgtctacgga cgtgggatcc tgcaccctgg tctgtcccct gaacaaccaa 961 gaggtaacag ctaaggatgg aacacagcgg tgtgagaaat gcagcaagcc ctgtgcccga 1021 gtgtgctacg gcctaggcat ggagcacctg cgggaggcga gggcagtcac cagtgccaac 1081 atccaagaat ttgtcggctg caagaagatc tttgggagcc tggcgtttct gccagagagc 1141 tttgagggg acccagcctc caacactgcc cccctgcagc ctgagcagct cagagtgttt 1201 gaggctctgg aggagattac aggttacctg tacatctcag cgtggccaga cagcttgcct 1261 aacctcagtg tcttccagaa cctcagagtg atccggggcc gagttctgca tgacggtgct 1321 tactcgctga cccttcaagg gctgggcatc agctggctgg ggctgcgctc gctggggggag 1381 ctggacagtg gactggccct catccaccgc aactcccgcc tctgcttcgt acacacggtg 1441 ccctgggacc agctcttccg gaacccccac caggccctgc tccacagcgc caaccggcca 1501 gaggacgagt gcgcgggtga gggcctggcc tgctatccgc tgtgtgccca cgggcactgc 1561 tggggtccgg acccacccca gtgtgtcaac tgcagccagt tccttcgggg ccaggagtgc 1621 gtggaggaat gccgagtatt gcaggggctt ccccgggagt atgtgaagga taggttctgt 1681 ctgccatgcc acccgaagtg tcagccccag aatggctcag tgacctgctt gggctcggaa 1741 gctgaccagt gtgtggcctg tgcccactac aaggaccctc ctttctgtgt ggctcgctgc 1801 cccagtgggg tgaaacctga cctctccttc atgcccatct ggaagttcgc agatgaggag 1861 ggcacgtgcc agccatgccc catcaactgc acccactcct gtgcgaacct ggacgagaag 1921 ggctgccccg ccgagcagag agccagccct atgacgtcca tcattgctgc tgtggtgggc 1981 attctgctgg tcgtggttgt ggggctggtc cttggcatcc taatcaagcg aaggcggcag 2041 aagatccgga agtacacgat gtga
```

SEQ ID NO: 29 - Feline (es)ERBB2ectm JN990983 (136-2196; with substitutions c728t, t729g, a1327c, g1328a, a1329g, t1408c, g1553a, a1999g, g2001c; taa)

```
   1 gtacaagaat gaagttgtgg agctgagagt cccctgcgtc gtgccccgag agccgaacag 61 agctcccagg cagccgcccg gcccttcgca gcccggtcca gcccgagcca tggggccgga 121 gccgcagtga gcaccatgga gctggcggcc tggtgccgct gggggctcct cctcgccctc 181 ctgcccctcc gagccacggg cacccaagtg tgcaccggca cagacatgaa gctgcggctc 241 ccagccagtc ccgagaccca cctggacatg ctccgccacc tctaccaggg ctgtcaagtg 301 gtacagggca acctggagct cacctacctg catgccaatg ccagcctctc cttcctgcag 361 gatatccagg aggtgcaagg ctatgtgctc attgcccaca accaagtgaa acaggtccca 421 ctgcagaggc tacgaatcgt gcgaggcacc cagctctttg gaggacaacta cgccctggcc 481 gtgctggaca cggagacccc actggacagt ggcaccccctg ctacaggggc tgccctagga
```

-continued

```
 541 gggctgcggg agctgcagct ccgaagcctc acagagatcc tgaagggagg ggtcctcatt 601 cagcggaacc cgcagctctg ccaccaggac acgattctgt ggaaggacat cttccacaag 661 aacaaccagc tggccctcat gctgatagac accaaccgct ctcgggcctg ccaaccctgt 721 tctccagtgt gtaaagactc ccactgctgg ggagcaagtt ccggggactg tcagagcttg 781 actcgaactg tctgtgctgg cggctgtgcc cgctgcaagg gcccgcagcc caccgactgc 841 tgccacgagc aatgtgctgc tggctgcacg ggccccaagc attctgactc cctggcctgc 901 ctccacttca accacagtgg catctgtgag ctgcactgcc cagccctggt cacctacaac 961 acggacacct tcgaatccat gcccaaccct gagggccgtt ataccttcgg tgccagctgt 1021 gtgactgcct gtccctacaa ctacctgtct acggacgtgg gatcctgcac cctggtctgt 1081 cccctgaaca accaagaggt gacagctgag gatggaacac agcggtgtga gaaatgcagc 1141 aagcccgtgt cccgagtgtg ctacggccta ggcatggagc acctgcggga ggcgagagca 1201 gtcaccagtg ccaacatcca agaatttgtc ggctgcaaga agatctttgg gagcctggcg 1261 tttctgccag agagctttga gggggaccca gcctccaaca ctgcccccct gcagcctgag 1321 cagctccagg tgtttgaggc tctggaggag attacaggtt acctgtacat ctcagcgtgg 1381 ccagacagct tgcctaacct cagtgtcctc cagaacctca gagtgatccg ggaccgagtt 1441 ctgcatgacg gtgcttactc gctaaccctt caagggctgg gcatcagctg gctggggctg 1501 cgctcgctgc gagagctggg cagtgggctg gccctcatcc accgcaactc ccacctctgc 1561 ttcgtacaca cggtgccctg ggaccagctc ttccggaacc cccaccaggc cctgctccac 1621 agcgccaacc ggccagagga cgagtgcgcg ggtgagggcc tggcctgcta tccgctgtgt 1681 gcccacggnc actgctgggg tccgggaccc acccagtgtg tcaactgcag ccagttcctt 1741 cggggccagg agtgcgtgga ggaatgccga gtattgcagg acttccccg ggagtatgtg 1801 aaggataggt tctgtctgcc atgccacccg gagtgtcagc cccaaaatgg ctcagtgacc 1861 tgcttgggct cggaagctga ccagtgtgtg gcctgtgccc actacaagga ccctcctttc 1921 tgtgtggctc gctgccccag tggggtgaaa cctgacctct ccttcatgcc catctggaag 1981 ttcgcagatg aggaggacgc ctgccagcca tgccccatca actgcaccca ctcctgtgcg 2041 gacctggacg agaagggctg ccccgccgag cagagagcca gccctgtgac gtccatcatt 2101 gctgctgtgg tgggcattct gctggtcgtg gttgtggggc tggtccttgg catcctaatc 2161 aagcgaaggc ggcagaagat ccggaagtac acgatgtaa
```

SEQ ID NO: 30 - Feline (es)ERBB2ectm-delta16 Feline (es)ERBB2ectm
(136-2033, 2082-2196; taa)

```
   1 gtacaagaat gaagttgtgg agctgagagt cccctgcgtc gtgccccgag agccgaacag 61 agctcccagg cagccgcccg gcccttcgca gcccggtcca gcccaagcca tggggccgga 121 gccgcagtaa gcaccatgga gctggcggcc tggtgccgct ggggactcct cctcgccctc 181 ctgcccctcc gagccacggg cacccaagtg tgcaccggca cagacatgaa gctgcggctc 241 ccagccagtc ccgagaccca cctggacatg ctccgccacc tctaccaggg ctgtcaagtg 301 gtacagggca acctggagct cacctacctg catgccaatg ccagcctctc cttcctgcag 361 gatatccagg aagtgcaaga ctatgtgctc attgcccaca ccaagtgaa acaggtccca 421 ctgcagaggc tacgaatcgt gcgaggcacc cagctctttg aggacaacta cgccctggcc 481 gtgctggaca cggagaccc actggacagt ggcaccccctg ctacaggggc tgccctagga 541 gggctgcggg agctgcagct ccgaagcctc acagagatcc tgaagggagg ggtcctcatt 601 cagcggaacc cgcagctctg ccaccagaac acgattctgt gaaaggacat cttccacaag
```

-continued

```
 661 aacaaccagc tggccctcat gctgatagac accaaccgct ctcgggcctg ccaaccctgt 721 tctccagtgt gtaaagactc ccactgctgg ggagcaagtt ccggggactg tcagagcttg 781 actcgaacta tctgtgctgg cggctgtgcc cgctgcaagg gcccgcagcc caccgactgc 841 taccacgagc aatgtgctgc tggctgcacg ggccccaagc attctagctg cctggcctgc 901 ctccacttca accacagtga catctgtgag ctgcactgcc cagccctggt cacctacaac 961 acggacacct cgaatccat gcccaaccct gagggccgtt ataccttcgg tgccagctgt 1021 gtgactgcct gtccctacaa ctacctgtct acggacgtgg gatcctgcac cctggtctgt 1081 cccctaaaca accaagaggt gacagctgag gatggaacac agcggtgtga gaaatgcagc 1141 aagccctgtg cccgagtgtg ctacggccta ggcatggagc acctgcggga ggcgagggca 1201 gtcaccagtg ccaacatcca agaatttgtc ggctgcaaga agatctttgg gagcctggcg 1261 tttctgccag agagctttga gggggaccca gcctccaaca ctgcccccct gcagcctgag 1321 cagctccagg tgtttgaggc tctggaggag attacaggtt acctgtacat ctcagcgtgg 1381 ccagacagct tgcctaacct cagtgtcctc cagaacctca gagtgatccg gggccgagtt 1441 ctgcatgaca gtgcttactc gctgaccctt caagggctgg gcatcagctg gctggggctg 1501 cgctcgctgc gggagctggg cagtgggctg gccctcatcc accgcaactc ccacctctgc 1561 ttcgtacaca cggtgccctg ggaccagctc ttccggaacc cccaccaggc cctgctccac 1621 agcgccaacc ggccagagga cgagtgcgcg ggtgagggcc tggcctgcta tccgctgtgt 1681 gcccacgggc actgctgggg tccgggaccc acccagtgtg tcaactgcag ccagttcctt 1741 cggggccagg agtgcgtgga ggaatgccga gtattgcagg acttccccg ggagtatgtg 1801 aaggataggt tctgtctgcc atgccacccg gagtgtcagc cccagaatgg ctcagtgacc 1861 tgcttgggct cggaagctga ccagtgtgtg gcctgtgccc actacaagga ccctccttc 1921 tgtgtggctc gctgccccag tggggtgaaa cctgacctct ccttcatgcc catctggaag 1981 ttcgcagatg aggaggacgc ctgccagcca tgccccatca actgcaccca ctcccctgtg 2041 acgtccatca ttgctgctgt ggtgggcatt ctgctggtcg tggttgtggg gctggtcctt 2101 ggcatcctaa tcaagcgaag gcggcagaag atccggaagt acacgatgta a
```

SEQ ID NO: 31 - Canine E2ectm (wt) NM_001003217 (1-2058, +TGA)
```
   1 atggagctgg cggctggtg ccgctggggg ctccttctcg ccctcctgcc ctccggagcc 61 gcgggcaccc aagtgtgcac cggcacagac atgaagctcc ggctcccggc cagtcccgag 121 acccacctgg atatgctccg ccacctgtac cagggctgtc aaatggtaca ggggaacctg 181 gagctcactt acctgcctgc caatgccagc ctgtccttcc tgcaggatat ccaggaggtg 241 cagggctatg tgctcattgc tcacagccaa atgaggcaga tcccactgca gaggctacga 301 attgtgcgag gcacccagct ctttgaggac aactacgccc tggccgtgct ggacaatgga 361 gacccgctgg agggtggcat ccctgcacca ggggcggccc aaggagggct gcgggagctg 421 caacttcgaa gcctcacaga gatcctgaag gaaggggtct tgattcagcg gagcccgcag 481 ctctgccacc aggacacgat tttatggaag gacgtcttcc ataagaacaa ccaactggcc 541 ctcacgctga tagacaccaa ccgcttttcg gcctaccgc cctgttctcc agcttgtaaa 601 gacgcccact gctggggggc cagctccggg gactgtcaga gcttgacgcg gactgtctgt 661 gccgggggct gtgcccgctg caagggccca caacccaccg actgctgcca cgagcagtgt 721 gctgctggct gcacgggccc caagcactct gactgcctgg cctgccttca cttcaaccac 781 agtggcatct gtgagctgca ctgcccagcc ctggtcacct acaacacgga caccttcgaa 841 tccatgccca accctgaggg ccgatatacc ttcggggcca gctgtgtgac ctcctgtccc
```

```
 901 tacaactacc tgtctacgga tgtgggatcc tgcaccctgg tctgtcccct gaacaaccaa 961 gaggtgacgg ctgaggatgg gacacagcgg tgcgagaaat gcagcaagcc ctgtgcccga 1021 gtgtgctacg gtctgggcat ggagcacctg cgagaggtga gagcggtcac cagtgcgaac 1081 atccaggagt ttgccggctg caagaagatc tttggaagcc tggcattttt gccagagagc 1141 tttaatgggg acccagcctc caacactgcc ccctacagc ctgagcagct cagagtgttt 1201 gaggctctgg aggagatcac aggttacctg tacatctcag cgtggccaga cagcctgcct 1261 aacctcagtg tcttccagaa cctgcgagta atccggggac gagttctgca tgatggtgcc 1321 tactcgctga ccctgcaagg gctgggcatc agctgactgg ggctgcgctc gctgcggaaa 1381 ctgggcagtg ggctggccct catccaccgc aacgcccgcc tttgcttcgt gcacacggtg 1441 ccctgggacc agctcttccg gaacccccac caggccctgc tccatagtgc caaccggcca 1501 gaggaggagt gcgtgggcga gggcctggcc tgctacccct gtgcccatgg gcactgctgg 1561 ggtccagggc ccacccagtg cgtcaactgc agccaattcc tccggggcca ggaatgcgtg 1621 gaagaatgcc gagtactgca ggggctgccc cgagagtatg tgaaggacag gtactgtcta 1681 ccgtgccact cagagtgtca gccccagaat ggctcagtga cctgtttcgg atcggaagct 1741 gaccagtgtg tggcctgcgc ccactacaag gaccctccct tctgtgtggc tcgctgcccc 1801 agtggtgtga aacctgacct gtccttcatg cccatctgga gttcgcaga tgaggagggc 1861 acttgccagc cgtacccccat caactgcacc cactcctgtg cgaacctgga cgagaagggc 1921 tgtcccgccg agcagagagc cagccctgtg acatccatca ttaccgctgt ggtgggcatt 1981 ctgctggctg tggtcgtggg gctggtcctc ggcatcctga tcaagcgaag gcggcagaag 2041 atccggaagt acactatgtg a
```

SEQ ID NO: 32 - Canine (es)E2ectm NM _001003217 (1-2058, +TGA; with
substitutions c593t, t594g, a1192c, g1193a, a1194g, t1273c, g1418a,
a1861g, t1863c))

```
   1 atggagctgg cggcctggtg ccgctggggg ctccttctcg ccctcctgcc ctccggagcc 61 gcgggcaccc aagtgtgcac cggcacagac atgaagctcc ggctcccggc cagtcccgag 121 acccacctgg atatgctccg ccacctgtac cagggctgtc aagtggtaca gggaaacctg 181 gagctcactt acctgcctgc caatgccagc ctgtccttcc tacaggatat ccaggaagtg 241 cagggctatg tgctcattgc tcacagccaa gtgaggcaga tcccactgca gaggctacga 301 attgtgcgag gcacccagct ctttgaggac aactacgccc tggccgtgct ggacaatgga 361 gacccgctgg agggtggcat ccctgcacca ggggcggccc aaggagggct gcgggagctg 421 cagcttcgaa gcctcacaga gatcctgaag ggaggggtct tgattcagcg gagcccgcag 481 ctctgccacc aggacacgat tttatggaag gacgtcttcc ataagaacaa ccagctggcc 541 ctcacgctga tagacaccaa ccgcttttcg gcctgccgc cctgttctcc agtgtgtaaa 601 gacgcccact gctggggggc cagctccggg gactgtcaga gcttgacgcg gactgtctgt 661 gccgggggct gtgccgctg caagggccca caacccaccg actgctgcca cgagcagtgt 721 gctgctggct gcacgggccc caagcactct gactgcctgg cctgccttca cttcaaccac 781 agtggcatct gtgagctgca ctgcccagcc ctggtcacct acaacacgga caccttcgaa 841 tccatgccca accctgaggg ccgatatacc ttcgggggcca gctgtgtgac ctcctgtccc 901 tacaactacc tgtctacgga tgtgggatcc tgcaccctgg tctgtcccct gaacaaccaa 961 gaggtgacgg ctgaggatgg gacacagcgg tgcgaaaaat gcagcaagcc ctgtgcccga 1021 gtgtgctacg gtctgggcat ggagcacctg cgagaggtga gagcggtcac cagtgcgaac 1081 atccaggagt ttgccggctg caagaagatc tttggaagcc tggcattttt gccagagagc
```

-continued

```
1141 tttgatgggg acccagcctc caacactgcc ccctacagc ctgagcagct ccaggtgttt 1201 gaggctctgg aggagatcac aggttacctg tacatctcag cgtggccaga cagcctgcct 1261 aacctcagtg tcctccagaa cctgcgagta atccggggac gagttctgca tgatggtgcc 1321 tactcgctga ccctgcaagg gctgggcatc agctggctgg ggctgcgctc gctgcgggaa 1381 ctgggcagtg ggctggccct catccaccgc aacgcccacc tttgcttcgt gcacacggtg 1441 ccctgggacc agctcttccg gaacccccac caggccctgc tccatagtgc caaccggcca 1501 gaggaggagt gcgtgggcga gggcctggcc tgctaccct gtgcccatgg gcactgctgg 1561 ggtccagggc ccacccagtg cgtcaactgc agccaattcc tccggggcca ggagtgcgtg 1621 gaggaatgcc gagtactgca ggggctgccc cgagaatatg tgaaggacag gtactgtcta 1681 ccgtgccact cagagtatca gccccagaat ggctcagtga cctgtttcgg atcggaggct 1741 gaccagtgtg tggcctgcgc ccactacaag gaccctccct tctgtgtggc tcgctgcccc 1801 agtggtgtga aacctgacct gtccttcatg cccatctgga agttcgcaga tgaggagggc 1861 gcctgccagc cgtgccccat caactgcacc cactcctgtg cggacctgga cgaaaagggc 1921 tgtcccgccg agcagagagc cagccctgtg acatccatca ttgccgctgt ggtaggcatt 1981 ctgctggctg tggtcgtggg gctggtcctc ggcatcctga tcaagcgaag gcggcagaag 2041 atccggaagt acactatgtg a
```

SEQ ID NO: 33 - Dog (es)E2ectm-delta16 Dog (es)E2ectm (with 1896-1943 deleted)

```
   1 atggagctgg cggcctggtg ccgctggggg ctccttctcg ccctcctgcc ctccggagcc 61 gcgggcaccc aagtgtgcac cggcacagac atgaagctcc ggctcccggc cagtcccgag 121 acccacctgg atatgctccg ccacctgtac cagggctgtc aagtggtaca ggggaacctg 181 gagctcactt acctgcctgc caatgccagc ctgtccttcc tgcaggatat ccaggaggtg 241 cagggctatg tgctcattgc tcacagccaa gtgaggcaga tcccactgca gaggctacga 301 attgtgcgag caccccagct ctttgaggac aactacgccc tggccgtgct ggacaatgga 361 gacccgctgg agggtggcat ccctgcacca ggggcggccc aaggagggct gcgggagctg 421 cagcttcgaa gcctcacaga gatcctgaag ggaggggtct tgattcagcg gagcccgcag 481 ctctgccacc aggacacgat tttatggaag gacgtcttcc ataagaacaa ccagctggcc 541 ctcacgctga tagacaccaa ccgcttttcg gcctgcccgc cctgttctcc agtgtgtaaa 601 gacgcccact gctggggggc cagctccggg gactgtcaga gcttgacgcg gactgtctgt 661 gccggggggct gtgcccgctg caagggccca caacccaccg actgctgcca cgagcagtgt 721 gctgctggct gcacgggccc caagcactct gactgcctgg cctgccttca cttcaaccac 781 agtggcatct gtgagctgca ctgcccagcc ctggtcacct acaaacggga caccttcgaa 841 tccatgccca accctgaggg ccgatatacc ttcggggcca gctgtgtgac ctcctgtccc 901 tacaactacc tgtctacgga tgtgggatcc tgcaccctgg tctgtccect gaacaaccaa 961 gaggtgacgg ctgaggatgg gacacagcgg tgcgagaaat gcagcaagcc ctgtgcccga 1021 gtgtgctacg tctgggcat ggagcacctg cgagaggtga gagcggtcac cagtgcgaac 1081 atccaggagt ttgccggctg caagaagatc tttggaagcc tggcattttt gccagagagc 1141 tttgatgggg acccagcctc caacactgcc ccctacagc ctgagcagct ccaggtgttt 1201 gaggctctgg aggagatcac aggttacctg tacatctcag cgtggccaga cagcctgcct 1261 aacctcagtg tcctccagaa cctgcgagta atccggggac gagttctgca tgatggtgcc 1321 tactcgctga ccctgcaagg gctgggcatc agctggctgg ggctgcgctc gctgcgggaa 1381 ctgggcagtg ggctggccct catccaccgc aacgcccacc tttgcttcgt gcacacggtg
```

-continued

```
1441 ccctaggacc agctcttccg gaaccccac caggccctgc tccatagtgc caaccggcca 1501 gaggaggagt gcgtgggcga gggcctggcc tgctacccct gtgcccatgg gcactgctgg 1561 ggtccagggc ccacccagtg cgtcaactgc agccaattcc tccggggcca ggagtgcgtg 1621 gaggaatgcc gagtactgca ggggctgccc cgagagtatg tgaaggacag gtactgtcta 1681 ccgtgccact cagagtgtca gccccagaat ggctcagtga cctgtttcgg atcggaggct 1741 gaccagtgtg tggcctgcgc ccactacaag gaccctccct tctgtgtggc tcgctgcccc 1801 agtggtgtga aacctgacct gtccttcatg cccatctgga agttcgcaga tgaggagggc 1861 gcctgccagc cgtgccccat caactgcacc cactcccctg tgacatccat cattgccgct 1921 gtggtgggca ttctgctggc tgtggtcgtg gggctggtcc tcggcatcct gatcaagcga 1981 aggcggcaga agatccggaa gtacactatg tga
```

PCR primers for construction of human ERBB2-delta16, feline ERBB2-delta16 and canine ERBB2-delta 16 and derivatives thereof.

```
SEQ ID NO: 34 - huE2-D16R
5'-GGAGTGGGTGCAGTTGATGG-3'

SEQ ID NO: 35 - huE2-D16F
5'-CCTCTGACGTCCATCATCTC-3'

SEQ ID NO: 36 - feE2-D16R
5'-GGAGTGGGTGCAGTTGATGG-3'

SEQ ID NO: 37 - feE2-D16F
5'-CCTGTGACGTCCATCATTG-3'

SEQ ID NO: 38 - caE2-D16R
5'-GGAGTGGGTGCAGTTGATGG-3'

SEQ ID NO: 39 - caE2-D16F
5'-CCTGTGACATCCATCATTG-3'
```

HER2 Fragments

```
SEQ ID NO: 40 - p95 - LPESFDGDPASNTAP

SEQ ID NO: 41 - p93 - KIFGSLAPLPESFDG

SEQ ID NO: 42 - p94 - SLAFLPESFDGDPAS

SEQ ID NO: 43 - p96 - FDGDPASNTAPLQPE

SEQ ID NO: 44 - p97 - PASNTAPLQPEQLQV

SEQ ID NO: 45 - ESFDGDPASNT
```

ABBREVIATIONS

AA Amino acid
B6 C57BL6
B6 HER2 Tg C57BL/6 HER2 transgenic
BALB HER2 Tg BALB/c HER2 transgenic
BLOSUM Blocks Substitutions Matrix
ECD Extracellular domain
ICD Intracellular domain
LOD Log of odds
Neu Rat homolog of erbB-2
pCMV Empty plasmid vector pCMV3
pE2TM pVax based construct encoding the ECD and TM of human erbB-2 (HER2)
pE2Neu pVax based construct encoding a hybrid human and rat erbB-2 protein
pGM-CSF Plasmid vector pEF-Bos based construct encoding mouse GM-CSF
ph(es)E2TM pVax based construct encoding the ECD and TM of HER-2 with evolution-selected AA changes
pNeu Vector pcDNA based construct encoding rat Neu
pNeuE2 pVax based construct encoding a hybrid Neu and HER-2 protein
prmE2TM pVax based construct encoding the ECD and TM of rhesus monkey erbB-2
pVax Empty plasmid vector pVAX1
SC Spleen cells
STR Short tandem repeat
Tg Transgenic
TM Transmembrane domain
USDA United States Department of Agriculture
WAP Whey acidic protein
wt Wild type Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of stimulating immune activity against a tumor-associated self-antigen, HER2, in a subject, comprising:

administering a therapeutically effective amount of an immunogenic composition comprising: a protein, the protein consisting of: amino acid sequence SEQ ID NO:2 to the subject.

2. The method of claim 1, wherein the immunogenic composition further comprises a pharmaceutically acceptable carrier.

3. The method of claim 1, wherein the immunogenic composition further comprises an immunostimulating adjuvant.

4. A method of stimulating immune activity against a tumor-associated self-antigen, HER2, in a subject, comprising: administering a nucleic acid encoding a protein consisting of: amino acid sequence SEQ ID NO:2, the nucleic acid encoding the protein operably linked to a heterologous regulatory nucleic acid sequence.

5. The method of claim 4, wherein the nucleic acid is present in an expression vector.

6. The method of claim 5, wherein the expression vector is a virus.

7. The method of claim 1, wherein the immunogenic composition is characterized by one or more of: 1) effectiveness to stimulate immune activity against a specified tumor-associated self-antigen in a subject, 2) effectiveness to overcome self-tolerance of the specified tumor-associated self-antigen, and 3) substantial similarity to the native three dimensional structure of the specified tumor-associated self-antigen.

* * * * *

SEQUENCE LISTING

Sequence total quantity: 44
SEQ ID NO: 1              moltype = AA   length = 687
FEATURE                   Location/Qualifiers
source                    1..687
                          mol_type = protein

```
                          organism = Homo sapiens
SEQUENCE: 1
MELAALCRWG LLLALLPPGA ASTQVCTGTD MKLRLPASPE THLDMLRHLY QGCQVVQGNL   60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPMCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLQVF ETLEEITGYL YISAWPDSLP  420
DLSVFQNLQV IRGRILHNGA YSLTLQGLGI SWLGLRSLRE LGSGLALIHH NTHLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GACQPCPINC THSCVDLDDK GCPAEQRASP LTSIISAVVG  660
ILLVVVLGVV FGILIKRRQQ KIRKYTM                                      687

SEQ ID NO: 2              moltype = AA  length = 687
FEATURE                   Location/Qualifiers
REGION                    1..687
                          note = h(es)E2ectm (human) with substitutions compared to
                          wild-typeM198V, Q398R, F425L, H473R, and A622T
source                    1..687
                          mol_type = protein
                          organism = synthetic construct
SEQUENCE: 2
MELAALCRWG LLLALLPPGA ASTQVCTGTD MKLRLPASPE THLDMLRHLY QGCQVVQGNL   60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPVCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLRVF ETLEEITGYL YISAWPDSLP  420
DLSVLQNLQV IRGRILHNGA YSLTLQGLGI SWLGLRSLRE LGSGLALIHH NTRLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GTCQPCPINC THSCVDLDDK GCPAEQRASP LTSIISAYVG  660
ILLVVVLGVV FGILIKRRQQ KIRKYTM                                      687

SEQ ID NO: 3              moltype = AA  length = 687
FEATURE                   Location/Qualifiers
source                    1..687
                          mol_type = protein
                          organism = Pan paniscus
SEQUENCE: 3
MELAALCRWG LLLALLPPGA ASTQVCTGTD MKLRLPASPE THLDMLRHLY QGCQVVQGNL   60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPMCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLQVF ETLEEITGYL YISAWPDSLP  420
DLSVFQNLQV IRGRILHNGA YSLTLQGLGI SWLGLRSLRE LGSGLALIHH NTHLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GTCQPCPINC THSCVDLDDK GCPAEQRASP LTSIISAVVG  660
ILLVVVLGVV FGILIKRRQQ KIRKYTM                                      687

SEQ ID NO: 4              moltype = AA  length = 664
FEATURE                   Location/Qualifiers
source                    1..664
                          mol_type = protein
                          organism = Saimiri boliviensis
SEQUENCE: 4
QVCTGTDMKL RLPASPETHL DMLRHLYQGC QVVQGNLELT YLPTNASLSF LQDIQEVQGY   60
VLIAHNQVRQ VPLQRLRIVR GTQLFEDNYA LAVLDNGDPL DNTTPVTGAS PGGLRELQLR  120
SLTEILKGGV WIQRNPQLCY QDTILWKDIF HKNNQLALTL IDTNRSRACH PCSPVCKGSR  180
CWGESSEDCQ SLTRTVCAGG CARCKGPLPT DCCHEQCAAG CTGPKHSDCL ACLHFNHSGI  240
CELHCPALVT YNTDTFESMP NPEGRYTFGA SCVTACPYNY LSTDVGSCTL VCPLHNQEVT  300
AEDGTQRCEK CSKPCARVCY GLGMEHLREV RAVTSANIQE FVGCKKIFGS LAFLPESFDG  360
DPASNTVPLQ PEQLHVFETL EEITGYLYIS AWPDSLPDLS VFQNLQVIRG RILHNGAYSL  420
TLQGLGISWL GLRSLRELGS GLALIHHNAR LCFVHTVPWD NLFRNPHQAL LHTANRPEHE  480
CVGKDLACHP LCARGHCWGP GPTQCVNCSQ FLRGQECVEE CRVLQGLPRE YVNARHCLPC  540
HPECQPQNGS VTCSGPEADQ CVACAHYKDS PFCVARCPSG VKPDLSYMPI WKFPDEEGTC  600
QPCPINCTHS CVDLDDKGCP AEQRASPLTS IISAVVGILL VMVLGLLLGI LIKRRQQKIR  660
KYTM                                                              664

SEQ ID NO: 5              moltype = AA  length = 687
FEATURE                   Location/Qualifiers
source                    1..687
                          mol_type = protein
```

-continued

```
                              organism = Pan troglodytes
SEQUENCE: 5
MELAALCRWG LLLALLPPGA ASTQVCTGTD MKLRLPASPE THLDMLRHLY QGCQVVQGNL   60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPMCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLQVF ETLEEITGYL YISAWPDSLP  420
DLSVFQNLQV IRGRILHNGA YSLTLQGLGI SWLGLRSLRE LGSGLALIHH NTHLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEK GTCQPCPINC THSCVDLDDK GCPAEQRASP LTSIISAVVG  660
ILLVVVLGVV FGILIKRRQQ KIRKYTM                                     687

SEQ ID NO: 6           moltype = AA  length = 687
FEATURE                Location/Qualifiers
source                 1..687
                       mol_type = protein
                       organism = Rhinopithecus roxellana
SEQUENCE: 6
MELAAWCRWG LLLALLPPGA AGTQVCTGTD MKLRLPASPE THLDMLRHLY QGCQVVQGNL   60
ELTYLPTDAS LSFLQDIQEV QGYVLIAHNQ VRQVPLQRLR IVRGTQLFED NYALAVLDNG  120
DPLNNITPVT GASPGGLREL QLRSLTEILK GGVLIQRNPQ LCYQDTILWK DIFHKNNQLA  180
FTLIDTNRSR ACHPCSPVCK GSHCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKSCAR VCYGLGMEHL REVRAVTSAN  360
IQEFAGCKKI FGSLAFLPES FDGDLASNTA PLQPEQLRVF ETLEEITGYL YISAWPDSLP  420
DLSILQNLQV IRGRILHNGA YSLTLQGLGI SWLGLRSLRE LGSGLALIHH NTRLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GTCQPCPINC THSCVDLDDK GCPAEQRASP LTSIISAVVG  660
ILLVVVLGVV FGILIKRRQQ KIRKYTM                                     687

SEQ ID NO: 7           moltype = AA  length = 687
FEATURE                Location/Qualifiers
source                 1..687
                       mol_type = protein
                       organism = Gorilla gorilla
SEQUENCE: 7
MELAALCRWG LLLALLPPGA ASTQVCTGTD MKLRLPASPE THLDMLRHLY QGCQVVQGNL   60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPVCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLQVF ETLEEITGYL YISAWPDSLP  420
DLSIFQNLQV IRGRILHNGA YSLTLQGLGI SWLGLRSLRE LGSGLALIHH NTHLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GACQPCPINC THSCVDLDDK GCPAEQRASP LTSIISAVVG  660
ILLVVVLGVV FGILIKRRQQ KIRKYTM                                     687

SEQ ID NO: 8           moltype = AA  length = 687
FEATURE                Location/Qualifiers
source                 1..687
                       mol_type = protein
                       organism = Chlorocebus sabaeus
SEQUENCE: 8
MELAAWCSWG LLLALLPPGA AGTQVCTGTD MKLRLPASPE THLDMLRHLY QGCQVVQGNL   60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPACK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLRVF ETLEEITGYL YISAWPDSLP  420
DLSVLQNLQV IRGRILHNGA YSLTLQGLGI SWLGLRSLRE LGSGLALIHH NTRLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GTCQPCPINC THSCVDLDDK GCPAEQRASP LTSIISAVVG  660
ILLVVVLGVV FGILIKRRQQ KIRKYTM                                     687

SEQ ID NO: 9           moltype = AA  length = 687
FEATURE                Location/Qualifiers
source                 1..687
                       mol_type = protein
                       organism = Papio anubis
SEQUENCE: 9
MELAAWCRWG LLLALLPPGA AGTQVCTGTD MKLRLPASPE THLDMLRHLY QGCQVVQGNL   60
```

-continued

```
ELTYLPTNAS LSFLQDIQEV QGYVLIAHNQ VRQVPLQRLR IVRGTQLFED NYALAVLDNG    120
DPLNNTTPVT GASPGGLREL QLRSLTEILK GGVLIQRNPQ LCYQDTILWK DIFHKNNQLA    180
LTLIDTNRSR ACHPCSPVCK GSRCWGESSE DCQSLTRTVC AGGCARCKGP LPTDCCHEQC    240
AAGCTGPKHS DCLACLHFNH SGICELHCPA LVTYNTDTFE SMPNPEGRYT FGASCVTACP    300
YNYLSTDVGS CTLVCPLHNQ EVTAEDGTQR CEKCSKPCAR VCYGLGMEHL REVRAVTSAN    360
IQEFAGCKKI FGSLAFLPES FDGDPASNTA PLQPEQLQVF ETLEEITGYL YISAWPDSLP    420
DLSVLQNLQV IRGRILHNGA YSLTLQGLGI SWLGLRSLRE LGSGLALIHH NTRLCFVHTV    480
PWDQLFRNPH QALLHTANRP EDECVGEGLA CHQLCARGHC WGPGPTQCVN CSQFLRGQEC    540
VEECRVLQGL PREYVNARHC LPCHPECQPQ NGSVTCFGPE ADQCVACAHY KDPPFCVARC    600
PSGVKPDLSY MPIWKFPDEE GTCQPCPINC THSCVDLDDK GCPAEQRASP LTSIISAVVG    660
ILLVVVLGVV FGILIKRRQQ KIRKYTM                                        687

SEQ ID NO: 10          moltype = AA   length = 687
FEATURE                Location/Qualifiers
source                 1..687
                       mol_type = protein
                       organism = Macaca mulatta
SEQUENCE: 10
MELAAWYRWG LLLALLPPGA AGTQVCTGTD MKLRLPASPE THLDMLRHLY QGCQVVQGNL    60
ELTYLPTNAS LSFLQDIQEV QGYVLIAHNQ VRQVPLQRLR IVRGTQLFED NYALAVLDNG    120
DLLNNTTPVT GASPGGLREL QLRSLTEILK GGVLIQRNPQ LCYQDTILWK DIFHKNNQLA    180
LTLIDTNRSR ACHPCSPVCK GSRCWGESSE DCQSLTRTVC AGGCARCKGP LPTDCCHEQC    240
AAGCTGPKHS DCLACLHFNH SGICELHCPA LVTYNTDTFE SMPNPEGRYT FGASCVTACP    300
YNYLSTDVGS CTLVCPLHNQ EVTAEDGTQR CEKCSKPCAR VCYGLGMEHL REVRAVTSAN    360
IQEFAGCKKI FGSLAFLPES FDGDPASNTA PLQPEQLRVF ETLEEITGYL YISAWPDSLP    420
DLSVLQNLQV IRGRILHNGA YSLTLQGLGI SWLGLRSLRE LGSGLALIHH NTRLCFVHTV    480
PWDQLFRNPH QALLHTANRP EDECVGEGLA CHQLCARGHC WGPGPTQCVN CSQFLRGQEC    540
VEECRVLQGL PREYVNARHC LPCHPECQPQ NGSVTCFGPE ADQCVACAHY KDPPFCVARC    600
PSGVKPDLSY MPIWKFPDEE GTCQSCPINC THSCVDLDDK GCPAEQRASP LTSIISAVVG    660
ILLVVVLGVV FGILIKRRQQ KIRKYTM                                        687

SEQ ID NO: 11          moltype = AA   length = 687
FEATURE                Location/Qualifiers
VARIANT                517
                       note = Xaa can be any naturally occurring amino acid
VARIANT                647
                       note = Xaa can be any naturally occurring amino acid
source                 1..687
                       mol_type = protein
                       organism = Macaca mulatta
SEQUENCE: 11
MELAAWYRWG LLLALLPPGA AGTQVCTGTD MKLRLPASPE THLDMLRHLY QGCQVVQGNL    60
ELTYLPTNAS LSFLQDIQEV QGYVLIAHNQ VRQVPLQRLR IVRGTQLFED NYALAVLDNG    120
DPLNNTTPVT GASPGGLREL QLRSLTEILK GGVLIQRNPQ LCYQDTILWK DIFHKNNQLA    180
LTLIDTNRSR ACHPCSPVCK GSRCWGESSE DCQSLTRTVC AGGCARCKGP LPTDCCHEQC    240
AAGCTGPKHS DCLACLHFNH SGICELHCPA LVTYNTDTFE SMPNPEGRYT FGASCVTACP    300
YNYLSTDVGS CTLVCPLHNQ EVTAEDGTQR CEKCSKPCAR VCYGLGMEHL REVRAVTSAN    360
IQEFAGCKKI FGSLAFLPES FDGDPASNTA PLQPEQLRVF ETLEEITGYL YISAWPDSLP    420
DLSVLQNLQV IRGRILHNGA YSLTLQGLGI SWLGLRSLRE LGSGLALIHH NTRLCFVHTV    480
PWDQLFRNPH QALLHTANRP EDECVGEGLA CHQLCAXGHC WGPGPTQCVN CSQFLRGQEC    540
VEECRVLQGL PREYVNARHC LPCHPECQPQ NGSVTCFGPE ADQCVACAHY KDPPFCVARC    600
PSGVKPDLSY MPIWKFPDEE GTCQPCPINC THSCVDLDDK GCPAEQXASP LTSIISAVVG    660
ILLVVVLGVV FGILIKRRQQ KIRKYTM                                        687

SEQ ID NO: 12          moltype = AA   length = 658
FEATURE                Location/Qualifiers
VARIANT                162
                       note = Xaa can be any naturally occurring amino acid
VARIANT                215
                       note = Xaa can be any naturally occurring amino acid
source                 1..658
                       mol_type = protein
                       organism = Pongo abelii
SEQUENCE: 12
MKLRLPASPE THLDMLRHLY QGCQVVQGNL ELTYLPTNAS LSFLQDIQEV QGYVLIAHNQ    60
VRQVPLQRLR IVRGTQLFED NYALAVLDNG DPLNNTTPVT GASPGGLREL QLRSLTEILK    120
GGVLIERNPQ LCYQDTILWK DIFHKNNQLA VTLIDTNRLS GXHPCFFRCV RAPRCWGESS    180
EDCQSLTRTV CAGGCARCKG PLPTDCCHEQ CLPSXHGPQA PSALPCLHFN HSGICELHCP    240
ALVTYNTDTF ESMPNPEGRY TFGASCVTAC PYNYLSTDVG SCTLVCPLHN QEVTAEDGTQ    300
RCEKCSKPCA RVCYGLGMEH LREVRAVTSA NIQEFAGCKK IFGSLAFLPE SFDGDPASNT    360
APLQPEQLRV FETLEEITGY LYISAWPDSL PDLSVFQNLQ VIRGRILHNG AYSLTLQGLG    420
ISWLGLRSLR ELGSGLALIH HNTRLCFVHT VPWDQLFRNP HQALLHTANR PEDECVGEGL    480
ACHQLCARGH CWGPGPTQCV NCSQFLRGQE CVEECRVLQG LPREYVNARY CLPCHPECQP    540
QNGSVTCFGP EADQCVACAH YKDPPFCVAR CPSGVKPDLS YMPIWKFPDE EGTCQPCPIN    600
CTHSCVDLDD KGCPAEQRAS PLTSIISAVV GILLVVVLGV VFGILIKRRQ QKIRKYTM      658

SEQ ID NO: 13          moltype = AA   length = 663
FEATURE                Location/Qualifiers
source                 1..663
```

```
                              mol_type = protein
                              organism = Nomascus leucogenys
SEQUENCE: 13
VCTGTDMKLR LPASPETHLD MLRHLYQGCQ VVQGNLELTY LPTNASLSFL QDIQEVQGYV  60
LIAHNQVRQV PLQRLRIVRG TQLFEDNYAL AVLDNGDPLN NTTLVTGASP GGLRELQLRS  120
LTEILKGGVL IQRNPQLCYQ DTILWKDIFH KNNQLALTLI DTNRSRACQP CSPVCKGSRC  180
WGESSEDCQS LTRTVCAGGC ARCKGPLPTD CCHEQCAAGC TGPKHSDCLA CLHFNHSGIC  240
ELHCPALVTY NTDTFESMPN PEGRYTFGAS CVTACPYNYL STDVGSCTLV CPLHNQEVTA  300
EDGTQRCEKC SKPCARVCYG LGMEHLREVR AVTSANIQEF AGCKKIFGSL AFLPESFDGD  360
PASNTAPLQP EQLQVFETLE EITGYLYISA WPDSLSDLSV FQNLQVIRGR ILHNGAYSLT  420
LQGLGISWLG LRSLRELGSG LALIHHNNRL CFVHTVPWDQ LFRNPHQALL HTANRPEDEC  480
VGEGLACHQL CARGHCWGPG PTQCVNCSQF LRGQECVEEC RVLQGLPREY VNARHCLPCH  540
PECQPQNGSV TCFGPEADQC VSCAHYKDPP FCVARCPSGV KPDLSYMPIW KFPDEEGTCQ  600
PCPINCTHSC VDLDDKGCPA EQRASPLTSI ISAVVGILLV VVLGAVFGIL IKRRQQKIRK  660
YTM                                                                663

SEQ ID NO: 14        moltype = AA  length = 687
FEATURE              Location/Qualifiers
source               1..687
                     mol_type = protein
                     organism = Callithrix jacchus
SEQUENCE: 14
MELAAWCRWG LLFALLPPGA AGTQVCTGTD MKLRLPASPE THLDMLRHLY QGCQVVQGNL  60
ELTYLPANAS LSFLQDIQEV QGYVLIAHNQ VRQVPLQRLR IVRGTQLFED NYALAVLDNG  120
DPLDNTTPVT GASPGGLREL QLRSLTEILK GGVWIQRNPQ LCYQDMVLWK DIFHKNNQLA  180
LTLIDTNRSR ACHPCSPACK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTV PLQPEQLQVF ETLEEITGYL YISAWPDSLP  420
DLSVFQNLQV IRGRILHNGA YLLTLQGLGI SWLGLRSLRE LGSGLALIHH NARLCFVHTV  480
PWDNLFRNPH QALLHTANRP EHECVGKDLA CHPLCARGHC WGPGPTQCVN CSQFLRGQEC  540
VEECRVLQGL PREYVNARHC LPCHPECQPQ NGSVTCSGPE ADQCVACAHY KDSPFCVARC  600
PSGVKPDLSY MPIWKFPDEE GTCQPCPINC THSCVDLDDK GCPAEQRASP LTSIISAVVG  660
ILLFMVLGLL LGILMKRRQQ KIRKYTM                                      687

SEQ ID NO: 15        moltype = AA  length = 687
FEATURE              Location/Qualifiers
source               1..687
                     mol_type = protein
                     organism = Macaca fascicularis
SEQUENCE: 15
MELAAWYRWG LLLALLPPGA TGTQVCTGTD MKLRLPASPE THLDMLRHLY QGCQVVQGNL  60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPVCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLRVF ETLEEITGYL YISAWPDSLP  420
DLSVLQNLQV IRGRILHNGA YSLTLQGLGI SWLGLRSLRE LGSGLALIHH NTRLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GTCQSCPINC THSCVDLDDK GCPAEQRASP LTSIISAVVG  660
ILLVVVLGVV FGILIKRRQQ KIRKYTM                                      687

SEQ ID NO: 16        moltype = AA  length = 671
FEATURE              Location/Qualifiers
source               1..671
                     mol_type = protein
                     organism = Homo sapiens
SEQUENCE: 16
MELAALCRWG LLLALLPPGA ASTQVCTGTD MKLRLPASPE THLDMLRHLY QGCQVVQGNL  60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPMCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLQVF ETLEEITGYL YISAWPDSLP  420
DLSVFQNLQV IRGRILHNGA YSLTLQGLGI SWLGLRSLRE LGSGLALIHH NTHLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GACQPCPINC THSPLTSIIS AVVGILLVVV LGVVFGILIK  660
RRQQKIRKYT M                                                       671

SEQ ID NO: 17        moltype = AA  length = 671
FEATURE              Location/Qualifiers
REGION               1..671
                     note = Human (es)E2ectm-delta 16; with substitutions M198V,
                     Q398R,F425L, H473R, and A622T
source               1..671
```

```
                              mol_type = protein
                              organism = synthetic construct
SEQUENCE: 17
MELAALCRWG LLLALLPPGA ASTQVCTGTD MKLRLPASPE THLDMLRHLY QGCQVVQGNL  60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPVCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLRVF ETLEEITGYL YISAWPDSLP  420
DLSVLQNLQV IRGRILHNGA YSLTLQGLGI SWLGLRSLRE LGSGLALIHH NTRLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GTCQPCPINC THSPLTSIIS AVVGILLVVV LGVVFGILIK  660
RRQQKIRKYT M                                                       671

SEQ ID NO: 18              moltype = AA  length = 687
FEATURE                    Location/Qualifiers
source                     1..687
                           mol_type = protein
                           organism = Felis catus
SEQUENCE: 18
MELAAWCRWG LLLALLPSGA TGTQVCTGTD MKLRLPASPE THLDMLRHLY QGCQVVQGNL  60
ELTYLHANAS LSFLQDIQEV QGYVLIAHNQ VKQVPLQRLR IVRGTQLFED NYALAVLDNG  120
DPLDSGTPAT GAALGGLREL QLRSLTEILK GGVLIQRNPQ LCHQDTILWK DIFHKNNQLA  180
LMLIDTNRSR ACQPCSPACK DSHCWGASSG DCQSLTRTVC AGGCARCKGP QPTDCCHEQC  240
AAGCTGPKHS DCLACLHFNH SGICELHCPA LVTYNTDTFE SMPNPEGRYT FGASCVTACP  300
YNYLSTDVGS CTLVCPLNNQ EVTAEDGTQR CEKCSKPCAR VCYGLGMEHL REARAVTSAN  360
IQEFVGCKKI FGSLAFLPES FEGDPASNTA PLQPEQLRVF EALEEITGYL YISAWPDSLP  420
NLSVFQNLRV IRGRVLHDGA YSLTLQGLGI SWLGLRSLRE LGSGLALIHR NSRLCFVHTV  480
PWDQLFRNPH QALLHSANRP EDECAGEGLA CYPLCAHGHC WGPGPTQCVN CSQFLRGQEC  540
VEECRVLQGL PREYVKDRFC LPCHPECQPQ NGSVTCLGSE ADQCVACAHY KDPPFCVARC  600
PSGVKPDLSF MPIWKFADEE GTCQPCPINC THSCADLDEK GCPAEQRASP VTSIIAAVVG  660
ILLVVVVGLV LGILIKRRRQ KIRKYTM                                      687

SEQ ID NO: 19              moltype = AA  length = 687
FEATURE                    Location/Qualifiers
REGION                     1..687
                           note = Feline (es)E2ectm with substitutions A198V, R398Q,
                            F425L, R473H,and T622A
source                     1..687
                           mol_type = protein
                           organism = synthetic construct
SEQUENCE: 19
MELAAWCRWG LLLALLPSGA TGTQVCTGTD MKLRLPASPE THLDMLRHLY QGCQVVQGNL  60
ELTYLHANAS LSFLQDIQEV QGYVLIAHNQ VKQVPLQRLR IVRGTQLFED NYALAVLDNG  120
DPLDSGTPAT GAALGGLREL QLRSLTEILK GGVLIQRNPQ LCHQDTILWK DIFHKNNQLA  180
LMLIDTNRSR ACQPCSPVCK DSHCWGASSG DCQSLTRTVC AGGCARCKGP QPTDCCHEQC  240
AAGCTGPKHS DCLACLHFNH SGICELHCPA LVTYNTDTFE SMPNPEGRYT FGASCVTACP  300
YNYLSTDVGS CTLVCPLNNQ EVTAEDGTQR CEKCSKPCAR VCYGLGMEHL REARAVTSAN  360
IQEFVGCKKI FGSLAFLPES FEGDPASNTA PLQPEQLRVF EALEEITGYL YISAWPDSLP  420
NLSVLQNLRV IRGRVLHDGA YSLTLQGLGI SWLGLRSLRE LGSGLALIHR NSHLCFVHTV  480
PWDQLFRNPH QALLHSANRP EDECAGEGLA CYPLCAHGHC WGPGPTQCVN CSQFLRGQEC  540
VEECRVLQGL PREYVKDRFC LPCHPECQPQ NGSVTCLGSE ADQCVACAHY KDPPFCVARC  600
PSGVKPDLSF MPIWKFADEE GACQPCPINC THSCADLDEK GCPAEQRASP VTSIIAAVVG  660
ILLVVVVGLV LGILIKRRRQ KIRKYTM                                      687

SEQ ID NO: 20              moltype = AA  length = 671
FEATURE                    Location/Qualifiers
source                     1..671
                           mol_type = protein
                           organism = Felis catus
SEQUENCE: 20
MELAAWCRWG LLLALLPSGA TGTQVCTGTD MKLRLPASPE THLDMLRHLY QGCQVVQGNL  60
ELTYLHANAS LSFLQDIQEV QGYVLIAHNQ VKQVPLQRLR IVRGTQLFED NYALAVLDNG  120
DPLDSGTPAT GAALGGLREL QLRSLTEILK GGVLIQRNPQ LCHQDTILWK DIFHKNNQLA  180
LMLIDTNRSR ACQPCSPVCK DSHCWGASSG DCQSLTRTVC AGGCARCKGP QPTDCCHEQC  240
AAGCTGPKHS DCLACLHFNH SGICELHCPA LVTYNTDTFE SMPNPEGRYT FGASCVTACP  300
YNYLSTDVGS CTLVCPLNNQ EVTAEDGTQR CEKCSKPCAR VCYGLGMEHL REARAVTSAN  360
IQEFVGCKKI FGSLAFLPES FEGDPASNTA PLQPEQLQVF EALEEITGYL YISAWPDSLP  420
NLSVLQNLRV IRGRVLHDGA YSLTLQGLGI SWLGLRSLRE LGSGLALIHR NSHLCFVHTV  480
PWDQLFRNPH QALLHSANRP EDECAGEGLA CYPLCAHGHC WGPGPTQCVN CSQFLRGQEC  540
VEECRVLQGL PREYVKDRFC LPCHPECQPQ NGSVTCLGSE ADQCVACAHY KDPPFCVARC  600
PSGVKPDLSF MPIWKFADEE GACQPCPINC THSPVTSIIA AVVGILLVVV VGLVLGILIK  660
RRRQKIRKYT M                                                       671

SEQ ID NO: 21              moltype = AA  length = 687
FEATURE                    Location/Qualifiers
source                     1..687
```

```
                         mol_type = protein
                         organism = Canis lupus
SEQUENCE: 21
MELAAWCRWG LLLALLPSGA AGTQVCTGTD MKLRLPASPE THLDMLRHLY QGCQVVQGNL    60
ELTYLPANAS LSFLQDIQEV QGYVLIAHSQ VRQIPLQRLR IVRGTQLFED NYALAVLDNG   120
DPLEGGIPAP GAAPGGLREL QLRSLTEILK GGVLIQRSPQ LCHQDTILWK DVFHKNNQLA   180
LTLIDTNRSR ACPPCSPACK DAHCWGASSG DCQSLTRTVC AGGCARCKGP QPTDCCHEQC   240
AAGCTGPKHS DCLACLHFNH SGICELHCPA LVTYNTDTFE SMPNPEGRYT FGASCVTSCP   300
YNYLSTDVGS CTLVCPLNNQ EVTAEDGTQR CEKCSKPCAR VCYGLGMEHL REVRAVTSCP   360
IQEFAGCKKI FGSLAFLPES FEGDPASNTA PLQPEQLRVF EALEEITGYL YISAWPDSLP   420
NLSVFQNLRV IRGRVLHDGA YSLTQGLGI SWLGLRSLRE LGSGLALIHR NARLCFVHTV    480
PWDQLFRNPH QALLHSANRP EEECVGEGLA CYPLCAHGHC WGPGPTQCVN CSQFLRGQEC   540
VEECRVLQGL PREYVKDRYC LPCHSECQPQ NGSVTCFGSE ADQCVACAHY KDPPFCVARC   600
PSGVKPDLSF MPIWKFADEE GTCQPCPINC THSCADLDEK GCPAEQRASP VTSIIAAVVG   660
ILLAVVVGLV LGILIKRRRQ KIRKYTM                                       687

SEQ ID NO: 22           moltype = AA   length = 687
FEATURE                 Location/Qualifiers
REGION                  1..687
                        note = Dog (es)E2ectm; with substitutions A198V, R398Q,
                        F425L, R473H,and T622A
source                  1..687
                        mol_type = protein
                        organism = synthetic construct
SEQUENCE: 22
MELAAWCRWG LLLALLPSGA AGTQVCTGTD MKLRLPASPE THLDMLRHLY QGCQVVQGNL    60
ELTYLPANAS LSFLQDIQEV QGYVLIAHSQ VRQIPLQRLR IVRGTQLFED NYALAVLDNG   120
DPLEGGIPAP GAAPGGLREL QLRSLTEILK GGVLIQRSPQ LCHQDTILWK DVFHKNNQLA   180
LTLIDTNRSR ACPPCSPVCK DAHCWGASSG DCQSLTRTVC AGGCARCKGP QPTDCCHEQC   240
AAGCTGPKHS DCLACLHFNH SGICELHCPA LVTYNTDTFE SMPNPEGRYT FGASCVTSCP   300
YNYLSTDVGS CTLVCPLNNQ EVTAEDGTQR CEKCSKPCAR VCYGLGMEHL REVRAVTSAN   360
IQEFAGCKKI FGSLAFLPES FEGDPASNTA PLQPEQLQVF EALEEITGYL YISAWPDSLP   420
NLSVLQNLRV IRGRVLHDGA YSLTQGLGI SWLGLRSLRE LGSGLALIHR NAHLCFVHTV    480
PWDQLFRNPH QALLHSANRP EEECVGEGLA CYPLCAHGHC WGPGPTQCVN CSQFLRGQEC   540
VEECRVLQGL PREYVKDRYC LPCHSECQPQ NGSVTCFGSE ADQCVACAHY KDPPFCVARC   600
PSGVKPDLSF MPIWKFADEE GACQPCPINC THSCADLDEK GCPAEQRASP VTSIIAAVVG   660
ILLAVVVGLV LGILIKRRRQ KIRKYTM                                       687

SEQ ID NO: 23           moltype = DNA   length = 2064
FEATURE                 Location/Qualifiers
source                  1..2064
                        mol_type = other DNA
                        organism = Homo sapiens
SEQUENCE: 23
atggagctgg cggccttgtg ccgctggggg ctcctcctcg ccctcttgcc ccccggagcc    60
gcgagcaccc aagtgtgcac cggcacagac atgaagctgc ggctccctgc cagtcccgag   120
acccacctgg acatgctccg ccacctctac cagggctgcc aggtggtgca gggaaacctg   180
gaactcacct acctgcccac caatgccagc ctgtccttcc tgcaggatat ccaggaggtg   240
cagggctacg tgctcatcgc tcacaaccaa gtgaggcagg tcccactgca gaggctgcgg   300
attgtgcgag gcacccagct cttttgaggac aactatgccc tggccgtgct agacaatgga   360
gacccgctga acaataccac ccctgtcaca ggggcctccc caggaggcct gcgggagctg   420
cagcttcgaa gcctcacaga gatcttgaaa ggaggggtct tgatccagcg gaaccccccag   480
ctctgctacc aggacacgat tttgtggaag gacatcttcc acaagaacaa ccagctggct   540
ctcacactga tagacaccaa ccgctctcgg gcctgccacc cctgttctcc gatgtgtaag   600
ggctcccgct gctggggaga gagttctgag gattgtcaga cactgtctgt   660
gccggtggct gtgcccgctg caagggggcca ctgcccactg actgctgcca tgagcagtgt   720
gctgccggct gcacgggccc caagcactct gactgcctgg cctgcctcca cttcaaccac   780
agtggcatct gtgagctgca ctgcccagcc ctggtcacct acaacacaga cacgtttgag   840
tccatgccca atcccgaggg ccggtataca ttcggcgcca gctgtgtgac tgcctgtccc   900
tacaactacc tttctacgga cgtgggatcc tgcaccctcg tctgccccct gcacaaccaa   960
gaggtgacag cagaggatgg aacacagcgg tgtgagaagt gcagcaagcc ctgtgcccga  1020
gtgtgctatg gtctgggcat ggagcacttg cgagaggtga gggcagttac cagtgccaat  1080
atccaggagt ttgctggctg caagaagatc tttgggagc tggcatttct gccggagagc  1140
tttgatgggg acccagcctc caacactgcc cgctccgac cagagcagct ccaagtgttt  1200
gagactctgg aagagatcac aggttaccta tacatctcag catggccgga cagcctgcct  1260
gacctcagcg tcttccagaa cctgcaagta atccggggac gaattctgca caatggcgcc  1320
tactcgctga ccctgcaagg gctgggcatc agctggctgg ggctgcgctc actgagggaa  1380
ctgggcagtg gactggccct catccaccat aacacccacc tctgcttcgt gcacacggtg  1440
ccctgggacc agctctttcg gaacccgcac aagctcctgc tccacactgc caacccggcca  1500
gaggacgagt gtgtgggcga gggcctggcc tgccaccagc tgtgcgcccg agggcactgc  1560
tggggtccag ggcccaccca gtgtgtcaac tgcagccagt tccttcgggg ccaggagtgc  1620
gtggaggaat gccgagtact gcaggggctc cccagggagt atgtgaatgc caggcactgt  1680
ttgccgtgcc accctgagtg tcagcccag aatggctcag tgacctgttt tggaccggag  1740
gctgaccagt gtgtggcctg tgcccactat aaggacccttc ccttctgcgt tgcccgctgc  1800
cccagcggtg tgaaacctga cctctcctac atgcccatct ggaagtttcc agatgaggag  1860
ggcgcatgcc agccttgccc catcaactgc acccactcct gtgctgacct ggatgacaag  1920
ggctgccccg ccgagcagag agccagccct ctgacgtcca tcatctctgc ggtggttggc  1980
attctgctgg tcgtggtctt ggggggtggtc tttgggatcc tcatcaagcg acggcagcag  2040
aagatccgga gtacacgat gtga                                          2064
```

-continued

```
SEQ ID NO: 24         moltype = DNA  length = 2064
FEATURE               Location/Qualifiers
misc_feature          1..2064
                      note = sequence encoding h(es)E2ectm (human) with
                       substitutions comparedto wild-type M198V, Q398R, F425L,
                      H473R, and A622T
source                1..2064
                      mol_type = other DNA
                      organism = synthetic construct
SEQUENCE: 24
atggagctgg cggccttgtg ccgctggggg ctcctcctcg ccctcttgcc ccccggagcc     60
gcgagcaccc aagtgtgcac cggcacagac atgaagctgc ggctccctgc cagtcccgag    120
acccacctgg acatgctccg ccacctctac cagggctgcc aggtggtgca gggaaacctg    180
gaactcacct acctgcccac caatgccagc ctgtccttcc tgcaggatat ccaggaggtg    240
cagggctacg tgctcatcgc tcacaaccaa gtgaggcagg tcccactgca gaggctgcgg    300
attgtgcgag gcacccagct ctttgaggac aactatgccc tggccgtgct agacaatgga    360
gacccgctga acaataccac ccctgtcaca ggggcctccc caggaggcct gcgggagctg    420
cagcttcgaa gcctcacaga gatcttgaaa ggaggggtct tgatccagcg gaacccccag    480
ctctgctacc aggacacgat tttgtggaag gacatcttcc acaagaacaa ccagctggct    540
ctcacactga tagacaccaa ccgctctcgg gcctgccacc cctgttctcc ggtgtgtaag    600
ggctcccgct gctggggaga gagttctgag gattgtcaga gcctgacgtg cactgtctgt    660
gccggtggct gtgcccgctg caaggggcca ctgcccactg actgctgcca tgagcagtgt    720
gctgccggct gcacgggccc caagcactct gactgcctgg cctgcctcca cttcaaccac    780
agtggcatct gtgagctgca ctgcccagcc ctggtcacct acaacacaga cacgtttgag    840
tccatgccca atcccgaggg ccggtataca ttcggcgcca gctgtgtgac tgcctgtccc    900
tacaactacc tttctacgga cgtgggatcc tgcaccctcg tctgcccct gcacaaccaa    960
gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcctccagaa cctgcaagta atccggggac gaattctgca caatggcgcc   1320
tactcgctga ccctgcaagg gctgggcatc agctggctgg ggctgcgctc actgagggaa   1380
ctgggcagtg gactggccct catccaccat aacacccacc tctgcttcgt gcacacggtg   1440
ccctgggacc agctctttcg gaacccgcac caagctctgc tccacactgc caaccggcca   1500
gaggacgagt gtgtgggcga gggcctggcc tgccaccagc tgtgcgcccg agggcactgc   1560
tggggtccag ggcccaccca gtgtgtcaac tgcagccagt tccttcgggg ccaggagtgc   1620
gtggaggaat gccgagtact gcaggggctc cccagggagt atgtgaatgc caggcactgt   1680
ttgccgtgcc accctgagtg tcagccccag aatggctcag tgacctgttt tggaccggga   1740
gctgaccagt gtgtggcctg tgcccactat aaggaccctc ccttctcgt ggcccgctgc   1800
cccagcggtg tgaaacctga cctctcctac atgcccatct ggaagtttcc agatgaggag   1860
ggcacatgcc agccttgccc catcaactgc acccactgct gtgtgaacct ggatgacaag   1920
ggctgccccg ccgagcagag agccagccct ctgacgtcca tcatctctgc ggtggttggc   1980
attctgctgg tcgtggtctt gggggtggtc tttgggatcc tcatcaagcg acggcagcag   2040
aagatccgga agtacacgat gtaa                                         2064

SEQ ID NO: 25         moltype = DNA  length = 2016
FEATURE               Location/Qualifiers
source                1..2016
                      mol_type = other DNA
                      organism = Homo sapiens
SEQUENCE: 25
atggagctgg cggccttgtg ccgctggggg ctcctcctcg ccctcttgcc ccccggagcc     60
gcgagcaccc aagtgtgcac cggcacagac atgaagctgc ggctccctgc cagtcccgag    120
acccacctgg acatgctccg ccacctctac cagggctgcc aggtggtgca gggaaacctg    180
gaactcacct acctgcccac caatgccagc ctgtccttcc tgcaggatat ccaggaggtg    240
cagggctacg tgctcatcgc tcacaaccaa gtgaggcagg tcccactgca gaggctgcgg    300
attgtgcgag gcacccagct ctttgaggac aactatgccc tggccgtgct agacaatgga    360
gacccgctga acaataccac ccctgtcaca ggggcctccc caggaggcct gcgggagctg    420
cagcttcgaa gcctcacaga gatcttgaaa ggaggggtct tgatccagcg gaacccccag    480
ctctgctacc aggacacgat tttgtggaag gacatcttcc acaagaacaa ccagctggct    540
ctcacactga tagacaccaa ccgctctcgg gcctgccacc cctgttctcc gatgtgtaag    600
ggctcccgct gctggggaga gagttctgag gattgtcaga gcctgacgtg cactgtctgt    660
gccggtggct gtgcccgctg caaggggcca ctgcccactg actgctgcca tgagcagtgt    720
gctgccggct gcacgggccc caagcactct gactgcctgg cctgcctcca cttcaaccac    780
agtggcatct gtgagctgca ctgcccagcc ctggtcacct acaacacaga cacgtttgag    840
tccatgccca atcccgaggg ccggtataca ttcggcgcca gctgtgtgac tgcctgtccc    900
tacaactacc tttctacgga cgtgggatcc tgcaccctcg tctgcccct gcacaaccaa    960
gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcctccagaa cctgcaagta atccggggac gaattctgca caatggcgcc   1320
tactcgctga ccctgcaagg gctgggcatc agctggctgg ggctgcgctc actgagggaa   1380
ctgggcagtg gactggccct catccaccat aacacccacc tctgcttcgt gcacacggtg   1440
ccctgggacc agctctttcg gaacccgcac caagctctgc tccacactgc caaccggcca   1500
gaggacgagt gtgtgggcga gggcctggcc tgccaccagc tgtgcgcccg agggcactgc   1560
```

```
tggggtccag ggcccaccca gtgtgtcaac tgcagccagt tccttcgggg ccaggagtgc   1620
gtggaggaat gccgagtact gcaggggctc cccaggagt  atgtgaatgc caggcactgt   1680
ttgccgtgcc accctgagtg tcagccccag aatggctcag tgacctgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc catcaactgc acccactccc ctctgacgtc catcatctct   1920
gcggtggttg gcattctgct ggtcgtggtc ttggggtgg  tctttgggat cctcatcaag   1980
cgacggcagc agaagatccg gaagtacacg atgtaa                             2016

SEQ ID NO: 26          moltype = DNA  length = 2064
FEATURE                Location/Qualifiers
misc_feature           1..2064
                       note = Sequence encoding Human (es)E2ectm-delta 16; with
                        substitutionsM198V, Q398R, F425L, H473R, and A622T
source                 1..2064
                       mol_type = other DNA
                       organism = synthetic construct
SEQUENCE: 26
atggagctgg cggccttgtg ccgctggggg ctcctcctcg ccctcttgcc ccccggagcc   60
gcgagcaccc aagtgtgcac cggcacagac atgaagctgc ggctccctgc cagtcccgag   120
acccacctgg acatgctccg ccacctctac cagggctgcc aggtggtgca gggaaacctg   180
gaactcacct acctgcccac caatgccagc ctgtccttcc tgcaggatat ccaggaggtg   240
cagggctacg tgctcatcgc tcacaaccaa gtgaggcagg tcccactgca gaggctgcgg   300
attgtgcgag gcacccagct ctttgaggac aactatgccc tggccgtgct agacaatgga   360
gaccccgctga acaataccac ccctgtcaca ggggcctccc caggaggcct gcgggagctg   420
cagcttcgaa gcctcacaga gatcttgaaa ggaggggtgt tgatccagcg gaaccccgag   480
ctctgctacc aggacacgat tttgtggaag gacatcttcc acaagaacaa ccagctggct   540
ctcacactga tagacaccaa ccgctctcgg gcctgccacc cctgttctcc ggtgtgtaag   600
ggctcccgct gctggggaga gagttctgag gattgtcaga gcctgacgcg cactgtctgt   660
gccggtggct gtgcccgctg caagggggcca ctgcccactg actgctgcca tgagcagtgt   720
gctgccggct gcacgggccc caagcactct gactgcctgg cctgcctcca cttcaaccac   780
agtggcatct gtgagctgca ctgcccagcc ctggtcacct acaacacaga cacgtttgag   840
tccatgccca tcccgaggg  ccggtataca ttcggcgcca gctgtgtgac tgcctgtccc   900
tacaactacc tttctacgga cgtgggatcc tgcaccctgg tctgcccct  gcacaaccaa   960
gaggtgacag cagaggatgg aacacagcgg tgtgagaagc gcagcaagcc ctgtgcccga   1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc ccgctccagc cagagcagct cagagtgttt   1200
gagactctgg aagagatcac aggttaccta tacatctcag catggccgga cagcctgcct   1260
gacctcagcg tcctccagaa cctgcaagta atccggggac gaattctgca caatggcgcc   1320
tactcgctga ccctgcaagg gctgggcatc agctggctgg ggctgcgctc actgagggaa   1380
ctgggcagtg gactggccct catccaccat aacacccgcc tctgcttcgt gcacacggtg   1440
ccctggaccc agctctttcg gaacccgcac caagctctgc tccacactgc caaccggcca   1500
gaggacgagt gtgtggggcga gggcctggcc tgccaccagc tgtgcgcccg agggcactgc   1560
tggggtccag ggcccaccca gtgtgtcaac tgcagccagt tccttcgggg ccaggagtgc   1620
gtggaggaat gccgagtact gcaggggctc cccaggagt  atgtgaatgc caggcactgt   1680
ttgccgtgcc accctgagtg tcagccccag aatggctcag tgacctgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcacatgcc agccttgccc catcaactgc acccactcct gtgtggacct ggatgacaag   1920
ggctgccccg ccgagcagag agccagccct ctgacgtcca tcatctgc  ggtggttggc   1980
attctgctgg tcgtggtctt ggggggtggtc tttgggatcc tcatcaagcg acggcagcag   2040
aagatccgga agtacacgat gtaa                                          2064

SEQ ID NO: 27          moltype = DNA  length = 2064
FEATURE                Location/Qualifiers
source                 1..2064
                       mol_type = other DNA
                       organism = Felis catus
SEQUENCE: 27
atggagctgg cggcctggtg ccgctggggg ctcctcctcg ccctcctgcc ctccggagcc   60
acgggcaccc aagtgtgcac cggcacagac atgaagctgc ggctcccagc cagtcccgag   120
acccacctgg acatgctccg ccacctctac cagggctgtc aagtggtaca gggcaacctg   180
gagctcacct acctgcatgc caatgccagc ctctccttcc tgcaggatat ccaggaggtg   240
caaggctatg tgctcattgc ccacaaccaa gtgaaacagg tcccactgca gaggctacga   300
atcgtgcgag gcacccagct ctttgaggac aactacgccc tggccgtgct ggacaacgga   360
gacccactgg acagtggcac ccctgctaca ggggctgccc taggagggct gcgggagctg   420
cagctccgaa gcctcacaga gatcctgaag ggaggggtc  tcattcagcg gaacccgcag   480
ctctgccacc aggacacgat tctgtggaag gacatcttcc acaagaacaa ccagctggct   540
ctcatgctga tagacaccaa ccgctctcgg gcctgccaac cctgttctcc agcttgtaaa   600
gactcccact ctggggggagc aagttccggg gactgtcaga gcttgactcg aactgtctgt   660
gctggcggct gtgcccgctg caagggcccg cagcccaccg actgctgcca cgagcaatgt   720
gctgctggct gcacgggccc caagcattct gactgcctgg cctgcctcca cttcaaccac   780
agtggcatct gtgagctgca ctgcccagcc ctggtcacct acaacacaga caccttcgaa   840
tccatgccca accctgaggg  ccgttatacc ttcggtgcca gctgtgtgac tgcctgtccc   900
tacaactacc tgtctacgga cgtgggatcc tgcaccctgg tctgcccct  gaacaaccaa   960
gaggtgacag ctgaggatgg aacacagcgg tgtgagaaat gcagcaagcc ctgtgcccga   1020
gtgtgctacg gcctaggcat ggagcacctg cgggaggcga gggcagtcac cagtgccaac   1080
atccaagaat tgtcggctg  caagaagatc tttgggagcc tggcgtttct gccagagagc   1140
```

```
tttgagggggg acccagcctc caacactgcc cccctgcagc ctgagcagct cagagtgttt  1200
gaggctctgg aggagattac aggttacctg tacatctcag cgtggccaga cagcttgcct  1260
aacctcagtg tcttccagaa cctcagagtg atccgggggcc gagttctgca tgacggtgct  1320
tactcgctga cccttcaagg gctgggcatc agctggctgg ggctgcgctc gctgcgggag  1380
ctgggcagtg ggctggccct catccaccgc aactcccgcc tctgcttcgt acacacggtg  1440
ccctgggacc agctcttccg gaacccccac caggccctgc tccacagcgc caaccggcca  1500
gaggacgagt gcgcgggtga gggcctggcc tgctatccgc tgtgtgccca cgggcactgc  1560
tggggtccgg gacccaccca gtgtgtcaac tgcagccagt tccttcgggg ccaggagtgc  1620
gtggaggaat gccgagtatt gcaggggctt ccccgggagt atgtgaagga taggttctgt  1680
ctgccatgcc acccggagtg tcagccccag aatggctcag tgacctgctt gggctcggaa  1740
gctgaccagt gtgtggcctg tgcccactac aaggaccctc cttttctgtgt ggctcgctgc  1800
cccagtgggg tgaaacctga cctctccttc atgcccatct ggaagttcgc agatgaggag  1860
ggcacgtgcc agccatgccc catcaactgc acccactcct gtgcggacct ggacgagaag  1920
ggctgccccg ccgagcagag agccagccct gtgacgtcca tcattgctgc tgtggtgggc  1980
attctgctgg tcgtggttgt ggggctggtc cttggcatcc taatcaagcg aaggcggcag  2040
aagatccgga agtacacgat gtga                                           2064
```

SEQ ID NO: 28          moltype = DNA  length = 2199
FEATURE                Location/Qualifiers
misc_feature          1..2199
                       note = Feline (es)ERBB2ectm; with substitutions c728t,
                       t729g, a1327c,g1328a, a1329g, t1408c, g1553a, a1999g,
                       g2001c
source                 1..2199
                       mol_type = other DNA
                       organism = synthetic construct
SEQUENCE: 28

```
gtacaagaat gaagttgtgg agctgagagt cccctgcgtc gtgccccgag agccgagcag  60
agctcccagg cagccgcccg gcccttcgca gcccggtcca gcccgagcca tggggccgga  120
gccgcagtga gcaccatgga gctggcggcc tggtgccgct gggggctcct cctcgccctc  180
ctgccctccg gagccacggg cacccaagtg tgcaccggca cagacatgaa gctgcgggtc  240
ccagccagtc ccgagaccca cctggacatg ctccgccacc tctaccaggg ctgtcaagtg  300
gtacagggca acctggagct cacctacctg catgccaatg ccagcctctc cttcctgcag  360
gatatccagg aggtgcaagg ctatgtgctc attgcccaca accaagtgaa acaggtccca  420
ctgcagaggc tacgaatcgt gcgaggcacc cagctctttg aggacaacta cgccctggcc  480
gtgctggaca acggagaccc actggacagt ggcaccccctg ctacaggggc tgccctagga  540
gggctgcggg agctgcagct ccgaagcctc acagagatcc tgaagggagg ggtcctcatt  600
cagcggaacc cgcagctctg ccaccaggac acgattctgt ggaaggacat cttccacaag  660
aacaaccagc tggccctcat gctgatagac accaaccgct ctcgggcctg ccaaccctgt  720
tctccagtgt gtaaagactc ccactgctgg ggagcaagtt ccggggactg tcagagcttg  780
actgaaactg tctgtgctgg cggctgtgcc cgctgcaagg gcccgcagcc caccgactgc  840
tgccacgagc aatgtgctgc tggctgcacg ggccccaagc attctgactg cctggcctgc  900
ctccacttca accacagtgg catctgtgag ctgcactgcc cagccctggt cacctacaac  960
acggacacct tcgaatccat gcccaaccct gagggccgtt ataccttcgg tgccagctgt  1020
gtgactgcct gtccctacaa ctacctgtct acggacgtgg gatcctgcac cctggtctgt  1080
cccctgaaca accaagaggt gacagctgag gatggaacac agcggtgtga gaaatgcagc  1140
aagccctgtg cccgagtgtg ctacggccta ggcatggagc acctgcggga ggcgagggca  1200
gtcaccagtg ccaacatcca agaatttgtc ggctgcaaga agatctttgg gagcctggcc  1260
tttctgccag agagctttga gggggaccca gcctccaaca ctgcccccct gcagcctgag  1320
cagctccagg tgtttgaggc tctggaggag attacaggtt acctgtacat ctcagcgtgg  1380
ccagacagct tgcctaacct cagtgtcctc cagaacctga gagtgatccg gggccgagtt  1440
ctgcatgacg gtgcttactc gctgacccct caagggctgg gcatcagctg gctggggctg  1500
cgctcgctgc gggagctggg cagtgggctg gccctcatcc accgcaactc ccacctctgc  1560
ttcgtacaca cggtgccctg ggaccagctc ttccggaacc cccaccaggc cctgctccac  1620
agcgccaacc ggccagagga cgagtgcgcg ggtgagggct tgcctgcta tccgctgtgt  1680
gcccacgggc actgctgggg tccgggaccc acccagtgtg tcaactgcag ccagttcctt  1740
cggggccagg agtgcgtgga ggaatgccga gtattgcagg ggcttccccg ggagtatgtg  1800
aaggataggt tctgtctgcc atgccacccg gagtgtcagc cccagaatgg ctcagtgacc  1860
tgcttgggct cggaagctga ccagtgtgtg gcctgtgccc actacaagga ccctcctttc  1920
tgtgtggctc gctgccccag tggggtgaaa cctgacctct ccttcatgcc catctgaag  1980
ttcgcagatg aggagggcgc ctgccagcca tgccccatca ctgcaccca ctcctgtgcg  2040
gacctggacg agaagggctg ccccgccgag cagagagcca gccctgtgac gtccatcatt  2100
gctgctgtgg tgggcattct gctggtcgtg gttgtgggggc tggtccttgg catcctaatc  2160
aagcgaaggc ggcagaagat ccggaagtac acgatgtaa                          2199
```

SEQ ID NO: 29          moltype = DNA  length = 2151
FEATURE                Location/Qualifiers
source                 1..2151
                       mol_type = other DNA
                       organism = Felis catus
SEQUENCE: 29

```
gtacaagaat gaagttgtgg agctgagagt cccctgcgtc gtgccccgag agccgagcag  60
agctcccagg cagccgcccg gcccttcgca gcccggtcca gcccgagcca tggggccgga  120
gccgcagtga gcaccatgga gctggcggcc tggtgccgct gggggctcct cctcgccctc  180
ctgccctccg gagccacggg cacccaagtg tgcaccggca cagacatgaa gctgcgggtc  240
ccagccagtc ccgagaccca cctggacatg ctccgccacc tctaccaggg ctgtcaagtg  300
gtacagggca acctggagct cacctacctg catgccaatg ccagcctctc cttcctgcag  360
gatatccagg aggtgcaagg ctatgtgctc attgcccaca accaagtgaa acaggtccca  420
ctgcagaggc tacgaatcgt gcgaggcacc cagctctttg aggacaacta cgccctggcc  480
```

-continued

```
gtgctggaca acggagaccc actggacagt ggcacccctg ctacaggggc tgccctagga    540
gggctgcggg agctgcagct ccgaagcctc acagagatcc tgaagggagg ggtcctcatt    600
cagcggaacc cgcagctctg ccaccaggac acgattctgt ggaaggacat cttccacaag    660
aacaaccagc tggccctcat gctgatagac accaaccgct ctcgggcctg ccaaccctgt    720
tctccagtgt gtaaagactc ccactgctgg ggagcaagtt ccggggactg tcagagcttg    780
actcgaactg tctgtgctgg cggctgtgcc cgctgcaagg gcccgcagcc caccgactgc    840
tgccacgagc aatgtgctgc tggctgcacg ggcccaagc attctgactg cctggcctgc     900
ctccacttca accacagtgg catctgtgag ctgcactgcc cagccctggt cacctacaac    960
acggacacct tcgaatccat gcccaaccct gagggccgtt ataccttcgg tgccagctgt   1020
gtgactgcct gtccctacaa ctacctgtct acggacgtgg gatcctgcac cctggtctgt   1080
cccctgaaca accaagaggt gacagctgag gatggaacac agcggtgtga gaaatgcagc   1140
aagccctgtg cccgagtgtg ctacggccta ggcatggagc acctgcggga ggcgagggca   1200
gtcaccagtg ccaacatcca agaatttgtc ggctgcaaga agatctttgg gagcctggcg   1260
tttctgccag agagctttga gggggaccca gcctccaaca ctgccccct gcagcctgag    1320
cagctccagg tgtttgaggc tctggaggag attacaggtt acctgtacat ctcagcgtgg   1380
ccagacagct tgcctaacct cagtgtcctc cagaacctca gagtgatccg gggccgagtt   1440
ctgcatgacg gtgcttactc gctgaccctt caagggctgg gcatcagctg gctggggctg   1500
cgctcgctgc gggagctggg cagtgggctg gccctcatcc accgcaactc ccacctctga   1560
ttcgtacaca cggtgccctg ggaccagctc ttccggaacc cccaccaggc cctgctccac   1620
agcgccaacc ggcagagga cgagtgcgcg ggtgagggcc tggcctgcta tccgctgtgt     1680
gcccacgggc actgctgggg tccgggaccc acccagtgtg tcaactgcag ccagttcctt   1740
cggggccagg agtgcgtgga ggaatgccga gtattgcagg ggcttccccg ggagtatgtg   1800
aaggataggt tctgtctgcc atgccacccg gagtgtcagc cccagaatgg ctcagtgacc   1860
tgcttgggct cggaagctga ccagtgtgtg gcctgtgccc actacaagga ccctcctttc   1920
tgtgtggctc gctgccccag tggggtgaaa cctgacctct ccttcatgcc catctggaag   1980
ttcgcagatg aggagggcgc ctgccagcca tgccccatca actgcaccca ctccctgtg    2040
acgtccatca ttgctgctgt ggtgggcatt ctgctggtcg tggttgtggg gctggtcctt   2100
ggcatcctaa tcaagcgaag gcggcagaag atccggaagt acacgatgta a             2151
```

```
SEQ ID NO: 30            moltype = DNA    length = 2061
FEATURE                  Location/Qualifiers
source                   1..2061
                         mol_type = other DNA
                         organism = Canis lupus
SEQUENCE: 30
atggagctgg cggcctggtg ccgctggggg ctccttctcg ccctcctgcc ctccggagcc     60
gcgggcaccc aagtgtgcac cggcacagac atgaagctcc ggctcccggc cagtcccgag    120
acccacctgg atatgctccg ccacctgtac cagggctgtc aagtggtaca ggggaacctg    180
gagctcactt acctgcctgc caatgccagc ctgtccttcc tgcaggatat ccaggaggtg    240
cagggctatg tgctcattgc tcacagccaa gtgaggcaga tcccactgca gaggctacga    300
attgtgcgag gcacccagct ctttgaggac aactacgccc tggccgtgct ggacaatgga    360
gacccgctgg agggtggcat ccctgcacca ggggcggccc aaggagggct gcgggagctg    420
cagcttcgaa gcctcacaga gatcctgaag ggaggggtct tgattcagcg gagcccgcag    480
ctctgccacc aggacacgat tttatggaag gacgtcttcc ataagaacaa ccagctggcc    540
ctcacgctga tagacaccaa ccgcttttcg gcctgcccgc cctgttctcc agcttgtaaa    600
gacgcccact gctgggggc cagctccggg gactgtcaga gcttgacgcg gactgtctgt     660
gccgggggct gtgccgctg caagggccca caacccaccg actgctgcca cgagcagtgt     720
gctgctggct gcacgggccc caagcactct gactgcctgg cctgccttca cttcaaccac    780
agtggcatct gtgagctgca ctgcccagcc ctggtcacct acaacacgga caccttcgaa    840
tccatgccca accctgaggg ccgatatacc ttcggggcca gctgtgtgac ctcctgtccc    900
tacaactacc tgtctacgga tgtgggatcc tgcaccctgg tctgtcccct gaacaaccaa    960
gaggtgacgg ctgaggatgg gacacagcg tgcgagaaat gcagcaagcc ctgtgcccga   1020
gtgtgctacg gtctgggcat ggagcacctg cgagaggtga gagcggtcac cagtgcgaac   1080
atccaggagt ttgccggctg caagaagatc tttggaagcc tggcattttt gccagagagc   1140
tttgatgggg acccagcctc caacactgcc ccctacagcc ctgagcagct caggagtgttt   1200
gaggctctgg aggagatcac aggttacctg tacatctcag cgtggccaga cagcctgcct   1260
aacctcagtg tcttccagaa cctgcgagta atccggggac gagttctgca tgatggtgcc   1320
tactcgctga ccctgcaagg gctgggcatc agctggctgg ggctgcgctc gctgcgggaa   1380
ctgggcagtg ggctggccct catccaccgc aacgcccgc tttgcttcgt gcacacggtg   1440
ccctgggacc agctcttccg gaaccccac caggccctgc tccatagtgc caaccggcca   1500
gaggaggagt gcgtgggcga gggcctggcc tgctacccct gtgcccatgg cactgctgg    1560
ggtccagggc ccacccagtg cgtcaactgc agccaattcc tccggggcca ggagtgcgtg   1620
gaggaatgcc gagtactgca ggggctgccc cgagagtatg tgaaggacag gtactgtcta   1680
ccgtgccact cagagtgtca gccccagaat ggctcagtga cctgtttcgg atcggaggct   1740
gaccagtgtg tggcctgcgc ccactacaag gaccctccct ctgtgtggc tcgctgcccc   1800
agtggtgtga aacctgacct gtccttcatg cccatctgga agttcgcaga tgaggagggc   1860
acttgccagc cgtgccccat caactgcacc cactcctgtg cggacctgga cgagaaggc    1920
tgtcccgccg agcagagagc cagccctgtg acatccatca ttgccgctgt ggtgggcatt   1980
ctgctggctg tggtcgtggg gctggtcctc ggcatcctga tcaagcgaag gcggcagaag   2040
atccggaagt acactatgtg a                                            2061
```

```
SEQ ID NO: 31            moltype = DNA    length = 2061
FEATURE                  Location/Qualifiers
misc_feature             1..2061
                         note = Canine (es)E2ectm; with substitutions c593t, t594g,
                         a1192c,g1193a, a1194g, t1273c, g1418a, a1861g, t1863c
source                   1..2061
                         mol_type = other DNA
                         organism = synthetic construct
```

```
SEQUENCE: 31
atggagctgg cggcctggtg ccgctggggg ctccttctcg ccctcctgcc ctccggagcc   60
gcgggcaccc aagtgtgcac cggcacagac atgaagctcc ggctcccggc cagtcccgag  120
acccacctgg atatgctccg ccacctgtac cagggctgtc aagtggtaca ggggaacctg  180
gagctcactt acctgcctgc caatgccagc ctgtccttcc tgcaggatat ccaggaggtg  240
cagggctatg tgctcattgc tcacagccaa gtgaggcaga tcccactgca gaggctacga  300
attgtgcgag gcacccagct cttttgaggac aactacgccc tggccgtgct ggacaatgga  360
gacccgctgg agggtggcat ccctgcacca ggggcggccc aaggagggct gcgggagctg  420
cagcttcgaa gcctcacaga gatcctgaag ggaggggtct tgattcagcg gagcccgcag  480
ctctgccacc aggacacgat tttatggaag gacgtcttcc ataagaacaa ccagctggcc  540
ctcacgctga tagacaccaa ccgcttttcg gcctgcccgc cctgttctcc agtgtgtaaa  600
gacgcccact gctggggggc cagctccggg gactgtcaga gcttgacgcg gactgtctgt  660
gccgggggct gtgcccgctg caagggccca caacccaccg actgctgcca cgagcagtgt  720
gctgctggct gcacgggccc caagcactct gactgcctgg cctgccttca cttcaaccac  780
agtggcatct gtgagctgca ctgcccagcc ctggtcacct acaacacgga caccttcgaa  840
tccatgccca accctgaggg ccgatatacc ttcggggcca gctgtgtgac ctcctgtccc  900
tacaactacc tgtctacgga tgtgggatcc tgcaccctgg tctgtcccct gaacaaccaa  960
gaggtgacgg ctgaggaatg gacacagcgg tgcgagaaat gcagcaagcc ctgtgcccga 1020
gtgtgctacg gtctgggcat ggagcacctg cgagaggtga gagcggtcac cagtgcgaac 1080
atccaggagt ttgccggctg caagaagatc tttggaagcc tggcattttt gccagagagc 1140
tttgatgggg acccagcctc caacactgcc cccctacagc ctgagcagct ccaggtgttt 1200
gaggctctgg aggagatcac aggttacctg tacatctcag cgtggccaga cagcctgcct 1260
aacctcagtg tcctccagaa cctgcgagta atccgggggac gagttctgca tgatggtgcc 1320
tactcgctga ccctcgaagg gctgggcatc agctggctgg ggctgcgctc gctgcgggaa 1380
ctgggcagtg ggctggccct catccaccgc aacgcccacc tttgcttcgt gcacacggtg 1440
ccctgggacc agctcttccg gaaccccac caggccctgc tccatagtgc caaccggcca 1500
gaggaggagt gcgtgggcga gggcctggcc tgctacccct gtgcccatgg gcactgctgg 1560
ggtccagggc ccacccagtg cgtcaactgc agccaattcc tccggggcca ggagtgcgtg 1620
gaggaatgcc gagtactgca ggggctgccc cgagagtatg tgaaggacag gtactgtcta 1680
ccgtgccact cagagtgtca gccccagaat ggctcagtga cctgtttcgg atcggaggct 1740
gaccagtgtg tggcctgcgc ccactacaag gaccctccct tctgtgtggc tcgctgcccc 1800
agtggtgtga aacctgacct gtccttcatg cccatctgga agttcgcaga tgaggagggc 1860
gcctgccagc cgtgccccat caactgcacc cactcctgtg cggacctgga cgagaagggc 1920
tgtcccgccg agcagagagc cagccctgtg acatccatca ttgccgctgt ggtgggcatt 1980
ctgctggctg tggtcgtggg gctggtcctc ggcatcctga tcaagcgaag gcggcagaag 2040
atccggaagt acactatgtg a                                           2061

SEQ ID NO: 32          moltype = DNA   length = 2013
FEATURE                Location/Qualifiers
source                 1..2013
                       mol_type = other DNA
                       organism = Canis lupus
SEQUENCE: 32
atggagctgg cggcctggtg ccgctggggg ctccttctcg ccctcctgcc ctccggagcc   60
gcgggcaccc aagtgtgcac cggcacagac atgaagctcc ggctcccggc cagtcccgag  120
acccacctgg atatgctccg ccacctgtac cagggctgtc aagtggtaca ggggaacctg  180
gagctcactt acctgcctgc caatgccagc ctgtccttcc tgcaggatat ccaggaggtg  240
cagggctatg tgctcattgc tcacagccaa gtgaggcaga tcccactgca gaggctacga  300
attgtgcgag gcacccagct ctttgaggac aactacgccc tggccgtgct ggacaatgga  360
gacccgctgg agggtggcat ccctgcacca ggggcggccc aaggagggct gcgggagctg  420
cagcttcgaa gcctcacaga gatcctgaag ggaggggtct tgattcagcg gagcccgcag  480
ctctgccacc aggacacgat tttatggaag gacgtcttcc ataagaacaa ccagctggcc  540
ctcacgctga tagacaccaa ccgcttttcg gcctgcccgc cctgttctcc agtgtgtaaa  600
gacgcccact gctggggggc cagctccggg gactgtcaga gcttgacgcg gactgtctgt  660
gccgggggct gtgcccgctg caagggccca caacccaccg actgctgcca cgagcagtgt  720
gctgctggct gcacgggccc caagcactct gactgcctgg cctgccttca cttcaaccac  780
agtggcatct gtgagctgca ctgcccagcc ctggtcacct acaacacgga caccttcgaa  840
tccatgccca accctgaggg ccgatatacc ttcggggcca gctgtgtgac ctcctgtccc  900
tacaactacc tgtctacgga tgtgggatcc tgcaccctgg tctgtcccct gaacaaccaa  960
gaggtgacgg ctgaggatgg gacacagcgg tgcgagaaat gcagcaagcc ctgtgcccga 1020
gtgtgctacg gtctgggcat ggagcacctg cgagaggtga gagcggtcac cagtgcgaac 1080
atccaggagt ttgccggctg caagaagatc tttggaagcc tggcattttt gccagagagc 1140
tttgatgggg acccagcctc caacactgcc ccccctacagc ctgagcagct ccaggtgttt 1200
gaggctctgg aggagatcac aggttacctg tacatctcag cgtggccaga cagcctgcct 1260
aacctcagtg tcctccagaa cctgcgagta atccgggggac gagttctgca tgatggtgcc 1320
tactcgctga ccctcgaagg gctgggcatc agctggctgg ggctgcgctc gctgcgggaa 1380
ctgggcagtg ggctggccct catccaccgc aacgcccacc tttgcttcgt gcacacggtg 1440
ccctgggacc agctcttccg gaaccccac caggccctgc tccatagtgc caaccggcca 1500
gaggaggagt gcgtgggcga gggcctggcc tgctacccct gtgcccatgg gcactgctgg 1560
ggtccagggc ccacccagtg cgtcaactgc agccaattcc tccggggcca ggagtgcgtg 1620
gaggaatgcc gagtactgca ggggctgccc cgagagtatg tgaaggacag gtactgtcta 1680
ccgtgccact cagagtgtca gccccagaat ggctcagtga cctgtttcgg atcggaggct 1740
gaccagtgtg tggcctgcgc ccactacaag gaccctccct tctgtgtggc tcgctgcccc 1800
agtggtgtga aacctgacct gtccttcatg cccatctgga agttcgcaga tgaggagggc 1860
gcctgccagc cgtgccccat caactgcacc cactccctg tgacatccat cattgccgct 1920
gtggtgggca ttctgctggc tgtggtcgtg gggctggtcc tcggcatcct gatcaagcga 1980
aggcggcaga agatccggaa gtacactatg tga                              2013

SEQ ID NO: 33          moltype = DNA   length = 20
```

-continued

```
FEATURE                 Location/Qualifiers
misc_feature            1..20
                        note = PCR primer (reverse) for human ERBB2-delta16
source                  1..20
                        mol_type = other DNA
                        organism = synthetic construct
SEQUENCE: 33
ggagtgggtg cagttgatgg                                            20

SEQ ID NO: 34           moltype = DNA  length = 20
FEATURE                 Location/Qualifiers
misc_feature            1..20
                        note = PCR primer (forward) for human ERBB2-delta16
source                  1..20
                        mol_type = other DNA
                        organism = synthetic construct
SEQUENCE: 34
cctctgacgt ccatcatctc                                            20

SEQ ID NO: 35           moltype = DNA  length = 20
FEATURE                 Location/Qualifiers
misc_feature            1..20
                        note = PCR primer (reverse) for feline ERBB2-delta16
source                  1..20
                        mol_type = other DNA
                        organism = synthetic construct
SEQUENCE: 35
ggagtgggtg cagttgatgg                                            20

SEQ ID NO: 36           moltype = DNA  length = 19
FEATURE                 Location/Qualifiers
misc_feature            1..19
                        note = PCR primer (forward) for feline ERBB2-delta16
source                  1..19
                        mol_type = other DNA
                        organism = synthetic construct
SEQUENCE: 36
cctgtgacgt ccatcattg                                             19

SEQ ID NO: 37           moltype = DNA  length = 20
FEATURE                 Location/Qualifiers
misc_feature            1..20
                        note = PCR primer (reverse) for canine ERBB2-delta16
source                  1..20
                        mol_type = other DNA
                        organism = synthetic construct
SEQUENCE: 37
ggagtgggtg cagttgatgg                                            20

SEQ ID NO: 38           moltype = DNA  length = 19
FEATURE                 Location/Qualifiers
misc_feature            1..19
                        note = PCR primer (forward) for canineERBB2-delta16
source                  1..19
                        mol_type = other DNA
                        organism = synthetic construct
SEQUENCE: 38
cctgtgacat ccatcattg                                             19

SEQ ID NO: 39           moltype = AA  length = 15
FEATURE                 Location/Qualifiers
REGION                  1..15
                        note = Human HER2 fragment
source                  1..15
                        mol_type = protein
                        organism = synthetic construct
SEQUENCE: 39
LPESFDGDPA SNTAP                                                 15

SEQ ID NO: 40           moltype = AA  length = 15
FEATURE                 Location/Qualifiers
REGION                  1..15
                        note = Human HER2 fragment
source                  1..15
                        mol_type = protein
                        organism = synthetic construct
SEQUENCE: 40
KIFGSLAPLP ESFDG                                                 15
```

-continued

```
SEQ ID NO: 41       moltype = AA  length = 15
FEATURE             Location/Qualifiers
REGION              1..15
                    note = Human HER2 fragment
source              1..15
                    mol_type = protein
                    organism = synthetic construct
SEQUENCE: 41
SLAFLPESFD GDPAS                                         15

SEQ ID NO: 42       moltype = AA  length = 15
FEATURE             Location/Qualifiers
REGION              1..15
                    note = Human HER2 fragment
source              1..15
                    mol_type = protein
                    organism = synthetic construct
SEQUENCE: 42
FDGDPASNTA PLQPE                                         15

SEQ ID NO: 43       moltype = AA  length = 15
FEATURE             Location/Qualifiers
REGION              1..15
                    note = Human HER2 fragment
source              1..15
                    mol_type = protein
                    organism = synthetic construct
SEQUENCE: 43
PASNTAPLQP EQLQV                                         15

SEQ ID NO: 44       moltype = AA  length = 11
FEATURE             Location/Qualifiers
REGION              1..11
                    note = Human HER2 fragment
source              1..11
                    mol_type = protein
                    organism = synthetic construct
SEQUENCE: 44
ESFDGDPASN T                                             11
```